US012678183B2

(12) United States Patent
Wallace et al.

(10) Patent No.: US 12,678,183 B2
(45) Date of Patent: *Jul. 14, 2026

(54) INVERTING THROMBECTOMY APPARATUSES AND METHODS

(71) Applicant: STRYKER CORPORATION, Fremont, CA (US)

(72) Inventors: Michael P. Wallace, Pleasanton, CA (US); Robert J. Garabedian, Mountain View, CA (US); Gavin P. Wallace, Pleasanton, CA (US)

(73) Assignee: STRYKER CORPORATION, Fremont, CA (US)

( * ) Notice: Subject to any disclaimer, the term of this patent is extended or adjusted under 35 U.S.C. 154(b) by 172 days.

This patent is subject to a terminal disclaimer.

(21) Appl. No.: 18/779,381

(22) Filed: Jul. 22, 2024

(65) Prior Publication Data

US 2024/0374273 A1     Nov. 14, 2024

Related U.S. Application Data

(63) Continuation of application No. 17/986,680, filed on Nov. 14, 2022, now Pat. No. 12,042,161, which is a (Continued)

(51) Int. Cl.
*A61B 17/221* (2006.01)
*A61B 17/00* (2006.01)

(52) U.S. Cl.
CPC .. *A61B 17/221* (2013.01); *A61B 2017/00853* (2013.01); *A61B 2017/00867* (2013.01); *A61B 2017/2215* (2013.01)

(58) Field of Classification Search
CPC . A61B 17/22; A61B 17/22031; A61B 17/221; A61B 17/32056;

(Continued)

(56) References Cited

U.S. PATENT DOCUMENTS

| | | | |
|---|---|---|---|
| 3,515,137 A | 6/1970 | Santomieri | |
| 4,222,380 A | 9/1980 | Terayama | |

(Continued)

FOREIGN PATENT DOCUMENTS

| | | |
|---|---|---|
| AU | 2015210338 A1 | 8/2015 |
| CN | 201079423 Y | 7/2008 |

(Continued)

OTHER PUBLICATIONS

Non-Final Office Action dated Feb. 1, 2018 for U.S. Appl. No. 15/496,668.

(Continued)

*Primary Examiner* — Phong Son H Dang
(74) *Attorney, Agent, or Firm* — Seager, Tufte & Wickhem, LLP

(57) ABSTRACT

A mechanical thrombectomy apparatus for removing a clot from a vessel includes an elongate inversion support catheter having a distal end opening, an elongate puller extending within the support catheter, and a knitted tractor tube extending over an outer surface of the support catheter, inverting into the distal end opening of the support catheter, and attached to the elongate puller at a first end within the support catheter, wherein the portion of the knitted tractor tube extending over the support catheter comprises a wire forming a helical spiral of alternating teardrop shaped-links each having a rounded apex, wherein each link is connected to two adjacent links so that the apex of each link is on an outward-facing surface of the tractor tube, wherein the links flare outward from an outer wall of the support catheter when the puller is pulled proximally within the support catheter.

20 Claims, 33 Drawing Sheets

Related U.S. Application Data continuation of application No. 16/731,649, filed on Dec. 31, 2019, now Pat. No. 11,497,512, which is a continuation-in-part of application No. 16/096,031, filed as application No. PCT/US2017/029345 on Apr. 25, 2017, now Pat. No. 10,888,342, said application No. 16/731,649 is a continuation-in-part of application No. PCT/US2018/040937, filed on Jul. 5, 2018.

(60) Provisional application No. 62/529,386, filed on Jul. 6, 2017, provisional application No. 62/393,460, filed on Sep. 12, 2016, provisional application No. 62/345,152, filed on Jun. 3, 2016, provisional application No. 62/327,024, filed on Apr. 25, 2016.

(58) Field of Classification Search
CPC ........... A61B 2017/00853; A61B 2017/00867; A61B 2017/2215
See application file for complete search history.

(56) References Cited

U.S. PATENT DOCUMENTS

| | | | |
|---|---|---|---|
| 4,243,040 A | 1/1981 | Beecher |
| 4,324,262 A | 4/1982 | Hall |
| 4,469,100 A | 9/1984 | Hardwick |
| 4,604,094 A | 8/1986 | Shook |
| 4,646,736 A | 3/1987 | Auth |
| 4,863,440 A | 9/1989 | Chin |
| 4,946,440 A | 8/1990 | Hall |
| 5,329,923 A | 7/1994 | Lundquist |
| 5,364,345 A | 11/1994 | Lowery et al. |
| 5,389,100 A | 2/1995 | Bacich et al. |
| 5,662,703 A | 9/1997 | Yurek et al. |
| 5,971,938 A | 10/1999 | Hart et al. |
| 6,156,055 A | 12/2000 | Ravenscroft |
| 6,221,006 B1 | 4/2001 | Dubrul et al. |
| 6,238,412 B1 | 5/2001 | Dubrul et al. |
| 6,245,078 B1 | 6/2001 | Ouchi |
| 6,258,115 B1 | 7/2001 | Dubrul |
| 6,544,278 B1 | 4/2003 | Vrba et al. |
| 6,569,181 B1 | 5/2003 | Burns |
| 6,620,179 B2 | 9/2003 | Boock et al. |
| 6,635,068 B1 | 10/2003 | Dubrul et al. |
| 6,635,070 B2 | 10/2003 | Leeflang et al. |
| 6,830,561 B2 | 12/2004 | Jansen et al. |
| 6,846,029 B1 | 1/2005 | Ragner et al. |
| 6,942,682 B2 | 9/2005 | Vrba et al. |
| 7,621,870 B2 | 11/2009 | Berrada et al. |
| 7,780,696 B2 | 8/2010 | Daniel et al. |
| 8,057,496 B2 | 11/2011 | Fischer, Jr. |
| 8,070,769 B2 | 12/2011 | Broome |
| 8,092,486 B2 | 1/2012 | Berrada et al. |
| 8,657,867 B2 | 2/2014 | Dorn et al. |
| 8,721,714 B2 | 5/2014 | Kelley |
| 8,784,442 B2 | 7/2014 | Jones et al. |
| 8,795,305 B2 | 8/2014 | Martin et al. |
| 8,956,384 B2 | 2/2015 | Berrada et al. |
| 9,028,401 B1 | 5/2015 | Bacich et al. |
| 9,125,683 B2 | 9/2015 | Farhangnia et al. |
| 9,126,016 B2 | 9/2015 | Fulton |
| 9,155,552 B2 | 10/2015 | Ulm, III |
| 9,173,668 B2 | 11/2015 | Ulm, III |
| 9,186,487 B2 | 11/2015 | Dubrul et al. |
| 9,259,237 B2 | 2/2016 | Quick et al. |
| 9,351,747 B2 | 5/2016 | Kugler et al. |
| 9,358,037 B2 | 6/2016 | Farhangnia et al. |
| 9,463,035 B1 | 10/2016 | Greenhalgh et al. |
| 9,643,035 B2 | 5/2017 | Mastenbroek |
| 9,717,514 B2 | 8/2017 | Martin et al. |
| 9,848,975 B2 | 12/2017 | Hauser |
| 9,849,014 B2 | 12/2017 | Kusleika |
| 9,962,178 B2 | 5/2018 | Greenhalgh et al. |
| 10,010,335 B2 | 7/2018 | Greenhalgh et al. |
| 10,016,266 B2 | 7/2018 | Hauser |
| 10,028,759 B2 | 7/2018 | Wallace et al. |
| 10,130,385 B2 | 11/2018 | Farhangnia et al. |
| 10,271,864 B2 | 4/2019 | Greenhalgh et al. |
| 10,327,883 B2 | 6/2019 | Yachia et al. |
| 2002/0032455 A1 | 3/2002 | Boock et al. |
| 2002/0173819 A1 | 11/2002 | Leeflang et al. |
| 2003/0083693 A1 | 5/2003 | Daniel et al. |
| 2003/0135258 A1 | 7/2003 | Andreas et al. |
| 2003/0153873 A1 | 8/2003 | Luther et al. |
| 2003/0168068 A1 | 9/2003 | Poole et al. |
| 2003/0176884 A1 | 9/2003 | Berrada et al. |
| 2003/0208224 A1 | 11/2003 | Broome et al. |
| 2004/0098033 A1 | 5/2004 | Leeflang et al. |
| 2004/0199202 A1 | 10/2004 | Dubrul et al. |
| 2005/0085826 A1 | 4/2005 | Nair et al. |
| 2005/0085849 A1 | 4/2005 | Sepetka et al. |
| 2005/0119668 A1 | 6/2005 | Teague et al. |
| 2005/0177132 A1 | 8/2005 | Lentz et al. |
| 2005/0187570 A1 | 8/2005 | Nguyen et al. |
| 2005/0245876 A1 | 11/2005 | Khosravi et al. |
| 2005/0283166 A1 | 12/2005 | Greenhalgh |
| 2005/0283186 A1 | 12/2005 | Berrada et al. |
| 2006/0047286 A1 | 3/2006 | West |
| 2006/0089533 A1 | 4/2006 | Ziegler et al. |
| 2006/0100662 A1 | 5/2006 | Daniel et al. |
| 2006/0173525 A1 | 8/2006 | Behl et al. |
| 2006/0195137 A1 | 8/2006 | Sepetka et al. |
| 2006/0200221 A1 | 9/2006 | Malewicz |
| 2006/0276874 A1 | 12/2006 | Wilson et al. |
| 2006/0293696 A1 | 12/2006 | Fahey et al. |
| 2007/0112374 A1 | 5/2007 | Paul, Jr. et al. |
| 2007/0123798 A1 | 5/2007 | Rahamimov |
| 2007/0149996 A1 | 6/2007 | Coughlin |
| 2007/0213765 A1 | 9/2007 | Adams et al. |
| 2008/0183136 A1 | 7/2008 | Lenker et al. |
| 2009/0076417 A1 | 3/2009 | Jones |
| 2010/0030256 A1 | 2/2010 | Dubrul et al. |
| 2010/0042136 A1 | 2/2010 | Berrada et al. |
| 2010/0087844 A1 | 4/2010 | Fischer, Jr. |
| 2010/0137846 A1 | 6/2010 | Desai et al. |
| 2010/0190156 A1 | 7/2010 | Van Wordragen et al. |
| 2010/0249815 A1 | 9/2010 | Jantzen et al. |
| 2011/0034987 A1 | 2/2011 | Kennedy |
| 2011/0118817 A1 | 5/2011 | Gunderson |
| 2011/0160763 A1 | 6/2011 | Ferrera et al. |
| 2011/0265681 A1 | 11/2011 | Allen et al. |
| 2011/0288529 A1 | 11/2011 | Fulton |
| 2011/0288572 A1 | 11/2011 | Martin |
| 2012/0059309 A1 | 3/2012 | Di Palma |
| 2012/0083824 A1 | 4/2012 | Berrada et al. |
| 2012/0083868 A1 | 4/2012 | Shrivastava et al. |
| 2012/0165859 A1 | 6/2012 | Eckhouse et al. |
| 2012/0271105 A1 | 10/2012 | Nakamura et al. |
| 2013/0046332 A1 | 2/2013 | Jones et al. |
| 2013/0096571 A1 | 4/2013 | Massicotte et al. |
| 2013/0116721 A1 | 5/2013 | Takagi et al. |
| 2013/0226196 A1 | 8/2013 | Smith |
| 2013/0317589 A1 | 11/2013 | Martin et al. |
| 2013/0345739 A1 | 12/2013 | Brady et al. |
| 2014/0005712 A1 | 1/2014 | Martin |
| 2014/0005717 A1 | 1/2014 | Martin et al. |
| 2014/0046133 A1 | 2/2014 | Nakamura et al. |
| 2014/0155980 A1 | 6/2014 | Turjman et al. |
| 2014/0257253 A1 | 9/2014 | Jemison |
| 2014/0276403 A1 | 9/2014 | Follmer et al. |
| 2014/0330286 A1 | 11/2014 | Wallace |
| 2014/0336691 A1 | 11/2014 | Jones et al. |
| 2014/0343593 A1 | 11/2014 | Chin et al. |
| 2014/0364896 A1 | 12/2014 | Consigny |
| 2014/0371779 A1 | 12/2014 | Vale et al. |
| 2015/0005781 A1 | 1/2015 | Lund-Clausen et al. |
| 2015/0005792 A1 | 1/2015 | Ahn |
| 2015/0018859 A1 | 1/2015 | Quick et al. |
| 2015/0018860 A1 | 1/2015 | Quick et al. |
| 2015/0088190 A1 | 3/2015 | Jensen |
| 2015/0112376 A1 | 4/2015 | Molaei et al. |
| 2015/0164523 A1 | 6/2015 | Brady et al. |
| 2015/0164666 A1 | 6/2015 | Johnson et al. |
| 2015/0190155 A1 | 7/2015 | Ulm, III |

(56) References Cited

U.S. PATENT DOCUMENTS

| | | |
|---|---|---|
| 2015/0190156 A1 | 7/2015 | Ulm, III |
| 2015/0196380 A1 | 7/2015 | Berrada et al. |
| 2015/0351775 A1 | 12/2015 | Fulton, III |
| 2016/0022293 A1 | 1/2016 | Dubrul et al. |
| 2016/0058458 A1 | 3/2016 | Hansen et al. |
| 2016/0058540 A1 | 3/2016 | Don Michael |
| 2016/0074627 A1 | 3/2016 | Cottone |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0206371 A1 | 7/2016 | Elgaard et al. |
| 2016/0228134 A1 | 8/2016 | Martin et al. |
| 2016/0242799 A1 | 8/2016 | Bonneau |
| 2016/0256179 A1 | 9/2016 | Walish et al. |
| 2017/0042571 A1 | 2/2017 | Levi |
| 2017/0086864 A1 | 3/2017 | Greenhalgh et al. |
| 2017/0100142 A1 | 4/2017 | Look et al. |
| 2017/0105743 A1 | 4/2017 | Vale et al. |
| 2017/0112513 A1 | 4/2017 | Marchand et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0348014 A1 | 12/2017 | Wallace et al. |
| 2018/0042624 A1 | 2/2018 | Greenhalgh et al. |
| 2018/0042626 A1 | 2/2018 | Greenhalgh et al. |
| 2018/0070968 A1 | 3/2018 | Wallace et al. |
| 2018/0236205 A1 | 8/2018 | Krautkremer et al. |
| 2019/0033614 A1 | 1/2019 | Jung et al. |
| 2019/0046219 A1 | 2/2019 | Marchand et al. |
| 2019/0117244 A1 | 4/2019 | Wallace et al. |
| 2019/0133622 A1 | 5/2019 | Wallace et al. |
| 2019/0133623 A1 | 5/2019 | Wallace et al. |
| 2019/0133624 A1 | 5/2019 | Wallace et al. |
| 2019/0133625 A1 | 5/2019 | Wallace et al. |
| 2019/0133626 A1 | 5/2019 | Wallace et al. |
| 2019/0133627 A1 | 5/2019 | Wallace et al. |
| 2019/0336148 A1 | 11/2019 | Greenhalgh et al. |

FOREIGN PATENT DOCUMENTS

| | | |
|---|---|---|
| CN | 102186427 A | 9/2011 |
| CN | 102988096 A | 3/2013 |
| CN | 103764049 A | 4/2014 |
| CN | 104068910 A | 10/2014 |
| CN | 104582608 A | 4/2015 |
| CN | 108348319 A | 7/2018 |
| CN | 111281482 A | 6/2020 |
| EP | 1254634 A1 | 11/2002 |
| GB | 1588072 A | 4/1981 |
| GB | 2498349 A | 7/2013 |
| JP | 2003038500 A | 2/2003 |
| JP | 2003135604 A | 5/2003 |
| JP | 201641275 A | 3/2016 |
| WO | 0032118 A1 | 6/2000 |
| WO | 0202162 A2 | 1/2002 |
| WO | 2005096963 A2 | 10/2005 |
| WO | 2008088371 A2 | 7/2008 |
| WO | 2009086482 A1 | 7/2009 |
| WO | 2012009675 A1 | 1/2012 |
| WO | 2012049652 A1 | 4/2012 |
| WO | 2012162437 A1 | 11/2012 |
| WO | 2015189354 A1 | 12/2015 |
| WO | 2017058280 A1 | 4/2017 |
| WO | 2017189535 A2 | 11/2017 |
| WO | 2017189550 A1 | 11/2017 |
| WO | 2017189591 A1 | 11/2017 |
| WO | 2017189615 A1 | 11/2017 |
| WO | 2017210487 A1 | 12/2017 |
| WO | 2018049317 A1 | 3/2018 |
| WO | 2019010318 A1 | 1/2019 |
| WO | 2019094456 A1 | 5/2019 |
| WO | 2019222117 A1 | 11/2019 |

OTHER PUBLICATIONS

Response to Restriction for U.S. Appl. No. 15/496,668, filed Feb. 21, 2018.

International Search Report and Written Opinion dated Feb. 28, 2018 for PCT/US2017/029345, American Stryker Corporation 26 pages.

Notice of Allowance dated Mar. 22, 2018 for U.S. Appl. No. 15/496,668.

Notice of Allowance dated Apr. 19, 2018 for U.S. Appl. No. 15/496,570.

Notice of Allowance dated Apr. 19, 2018 for U.S. Appl. No. 15/496,786.

Non-Final Office Action dated Sep. 5, 2018 for U.S. Appl. No. 15/291,015.

Extended European Search Report dated Aug. 22, 2018 for European Patent Application No. 16852212.6.

Extended European Search Report dated Oct. 5, 2018 for European Patent Application No. 18174891.4.

Invitation to Pay Additional Fees for International Patent Application No. PCT/US2018/070937 dated Sep. 26, 2018.

Response to Non-Final Office Action for U.S. Appl. No. 15/291,015, filed Sep. 5, 2018.

International Search Report and Written Opinion dated Nov. 14, 2018 for PCT/US2018/040937, Applicant Stryker Corporation 16 pages.

Notice of Allowance dated Dec. 11, 2018 for U.S. Appl. No. 15/291,015.

Invitation to Pay Additional Fees for International Application No. PCT/US2018/059607 dated Jan. 31, 2019.

Japanese Office Action dated Mar. 19, 2019 for Japanese Application No. 2018-535810 (with English Language translation).

International Search Report and Written Opinion dated Mar. 28, 2019 for International Application No. PCT/US2018059607.

Notice of Allowance dated Apr. 10, 2019 for U.S. Appl. No. 15/611,546.

Response to Extended European Search Report for EP Patent Application No. 16852212.6 dated Mar. 15, 2019.

European Patent Office Communication Rule 161(1) and 162 dated Feb. 5, 2019 for EP Patent Application No. 17729703.3.

European Patent Office Communication Rule 161(1) and 162 EPC for EP Patent Application No. 17737084.8 dated Dec. 18, 2018.

European Patent Office Communication Rule 161(1) and 162 for EP Patent Application No. 17722277.5 dated Dec. 13, 2018.

European Patent Office Communication Rule 161(1) and 162 dated Dec. 13, 2018 for EP Patent Application No. 17722290.8.

European Patent Office Communication Rule 161(1) and 162 dated Dec. 13, 2018 for EP Patent Application No. 17721036.6.

Response to Extended European Search Report for EP Patent Application No. 18174891.4 dated May 28, 2019.

Restriction Requirement dated Jun. 28, 2019 for U.S. Appl. No. 15/700,685.

International Search Report and Written Opinion dated May 6, 2016 for PCT/US2016/017982.

Response to European Patent Office Communication Rule 161(1) and 162 EPC filed Jun. 11, 2019 for EP Patent Application No. 177372084.8.

Response to European Patent Office Communication Rule 161(1) and 162 filed Jun. 4, 2019 for EP Patent Application No. 17722277.5.

Response to European Patent Office Communication Rule 161(1) and 162 filed Jun. 4, 2019 for EP Patent Application No. 17722290.8.

Response to European Patent Office Communication Rule 161(1) and 162 filed Jun. 11, 2019 for EP Patent Application No. 17721036.6.

European Patent Office Communication Rule161(1) and 162 dated Apr. 23, 2019 for EP Patent Application No. 17772186.7.

Response to Non-Final Office Action filed Nov. 8, 2017 for U.S. Appl. No. 15/496,570.

Response to Non-Final Office Action filed Feb. 1, 2018 for U.S. Appl. No. 15/496,786.

(56) References Cited

OTHER PUBLICATIONS

Restriction Requirement dated Apr. 11, 2019 for U.S. Appl. No. 15/497,092.
Response to Restriction Requirement filed Jun. 11, 2019 for U.S. Appl. No. 15/497,092.
Ex Parte Quayle Office Action mailed Jul. 16, 2019 for U.S. Appl. No. 15/497,092.
Response to Rule 161(1) and 162 EPC filed on Jul. 23, 2019 for EP Application No. 17729703.3.
PCT International Search Report and Written Opinion for International Patent Application No. PCT/US2019/032601, Applicant Stryker Corporation, dated Jul. 23, 2019 (12 pages).
Response to Restriction Requirement filed Jul. 25, 2019 for U.S. Appl. No. 15/700,685.
Response to Ex Parte Quayle Office Action filed Jul. 25, 2019 for U.S. Appl. No. 15/497,092.
Office Action dated Jun. 5, 2019 for Chinese Application No. 2019053101871820, including partial English language translation provided by the foreign associate.
Wikipedia; Embolectomy; retrieved from the internet: https://en.wikipedia.org/wiki/Emboloectomy; 4 pages; retrieved/printed: Mar. 24, 2016.
O'Sullivan; "Thrombolysis versus thrombectomy in acute deep vein thrombosis," Cardiology; vol. 3, Issue 5, pp. 589-596; Oct. 2011.
Capture Vascular Systems; (company website); retrieved from the internet: http://capturevascular.com; 3 pages; retrieved/printed: Mar. 24, 2016.
Edwards Lifesciences; Fogarty® Occlusion Catheters (product brochure); retrieved from the internet: http://web.archive.org/web/20150228193218/http://www.edwards.com/products/vascular/atraumaticocclusion/pages/occlusioncatheter.aspx; © 2011; 2 pgs; retrieved/printed: Mar. 24, 2011.
Boston Scientific; Fetch(TM) 2 Aspiration Catheter (product information); retrieved from the internet: http://www.bostonscientific.com/en-US/products/thrombectomy-systems/fetch2-aspiration-catheter.html: 5 pages; retrieved/printed : Mar. 24, 2016.
Penumbra, Inc.; Indigo® System (product information); retrieved from the internet: http://www.penumbrainc.com/peripheralpercutaneous-thromboembolectomy/indigo-system; 2 pages; retrieved/printed: Mar. 24, 2016.
Youtube; Merci Retrieval System X Series Animation; uploaded Mar. 16, 2009 (product information); retrieved from the internet: https://youtube.com/watch?v - MGX7deuFkhc; 3 pages; retrieved/printed: Mar. 24, 2016.
Covidien; Solitaire(TM) AS Neurovascular Remodeling Device (product information); retrieved from the internet: http://www.ev3.net/neuro/intl/remodeling-devices/solitaire-ab.htm; © 2015; 2 pages; retrieved/printed: Mar. 24, 2016.
Notice of Allowance for U.S. Appl. No. 15/043,996, dated Jun. 9, 2016.
Ex Parte Quayle Office Action mailed Aug. 2, 2019 for U.S. Appl. No. 15/497,092.
Non Final Office Action dated Aug. 23, 2019 for U.S. Appl. No. 15/700,685.
Non-Final Office Action dated Sep. 3, 2019 for U.S. Appl. No. 15/794,939.
Rule 71(3) Allowance for EP Patent Application No. 18174891.4 dated Jul. 30, 2019.
Response to Ex Parte Quayle Office Action filed Sep. 17, 2019 for U.S. Appl. No. 15/497,092.
Office Action Response filed on Sep. 26, 2019 for Chinese Patent Application No. 2016800567527, no translation received.
Non-Final Office Action dated Oct. 4, 2019 for U.S. Appl. No. 15/795,097.
Response to Restriction filed Oct. 4, 2019 for U.S. Appl. No. 15/795,097.
Notice of Allowance dated Sep. 27, 2019 for U.S. Appl. No. 15/497,092.
Extended European Search Report dated Oct. 8, 2019 for European Patent Application No. 19191925.7.

Office Action dated Oct. 7, 2019 for European Patent Application No. 17729703.3.
Office Action dated Oct. 7, 2019 for European Patent Application No. 17737084.8.
Response to European Patent Office Communication Rule161(1) and 162 filed Oct. 17, 2019 for EP Patent Application No. 17772186.7.
Invitation to Pay Additional Fees for International Patent Application No. PCT/US2019/050467 dated Oct. 25, 2019.
International Search Report and Written Opinion for International Patent Application No. PCT/US2019/050140 dated Oct. 25, 2019.
Notice of Allowance dated Oct. 24, 2019 for U.S. Appl. No. 15/611,546.
Response to Non Final Office Action filed Nov. 8, 2019 for U.S. Appl. No. 15/700,685.
Notice of Allowance dated Nov. 6, 2019 for U.S. Appl. No. 15/795,097.
Rule 71(3) Allowance for EP Patent Application No. 17721063.6 dated Oct. 23, 2019.
Rule 71(3) Allowance for EP Patent Application No. 17722290.8 dated Nov. 11, 2019.
Notice of Allowance dated Nov. 21, 2019 for U.S. Appl. No. 15/700,685.
Amendment Response dated Dec. 3, 2019 for U.S. Appl. No. 15/794,939.
PCT International Search Report and Written Opinion for International Patent Application No. PCT/US2019/050467, Applicant Stryker Corporation, dated Dec. 18, 2019 (17 pages).
Non-Final Office Action dated Dec. 27, 2019 for U.S. Appl. No. 16/594,256.
Final Office Action dated Mar. 2, 2020 for U.S. Appl. No. 15/794,939.
Notice of Allowance for U.S. Appl. No. 15/794,939 dated Mar. 31, 2020.
Amendment Response dated Mar. 27, 2020 for U.S. Appl. No. 16/594,256.
Non-Final Office Action for U.S. Appl. No. 16/096,031 dated May 8, 2020.
Non-Final Office Action for U.S. Appl. No. 16/183,162 dated May 13, 2020.
Non-Final Office Action for U.S. Appl. No. 16/169,334 dated May 8, 2020.
Non-Final Office Action for U.S. Appl. No. 16/183,171 dated May 13, 2020.
Foreign OA for Japanese Patent Application No. 2018-535810 dated Feb. 7, 2020.
Foreign Communication Under Rule 71(3) for EP Patent Application No. 18807524.6 dated Jul. 1, 2022.
Foreign Communication Pursuant to Article 94(3) for EP Patent Application No. 17772186.7 dated Jun. 17, 2022.
Extended European Search Report for EP Patent Application No. 22162955.3 dated Sep. 5, 2022.
Foreign Notice of Rejection for JP Patent Application No. 2020-093260 dated Aug. 2, 2022.
Foreign Response for EP Patent Application No. 21192438.6 dated Jul. 18, 2022.
Foreign Response for EP Patent Application No. 2021-72088 dated Jul. 4, 2022.
Notice of Rejection for JP Patent Application No. 2020-523723 dated Aug. 8, 2022 with English translation.
Amendment Response to NFOA for U.S. Appl. No. 16/707,045 dated Jul. 11, 2022.
Final Office Action for U.S. Appl. No. 16/707,045 dated Jul. 22, 2022.
Notice of Allowance for U.S. Appl. No. 16/790,744 dated Jun. 17, 2022.
Foreign OA for CN Patent Application No. 201880046302.9 dated Aug. 25, 2022 (with English translation).
Foreign OA for JP Patent Application No. 2021-125123 dated Aug. 23, 2022.
Foreign Notice of Reasons of Rejection for JP Patent Application No. 2019-513286 dated Jul. 26, 2021 (with English translation).
Foreign Exam Report for EP Patent Application No. 19773654.9 dated Aug. 24, 2021.

(56)        References Cited

OTHER PUBLICATIONS

Foreign OA for JP Patent No. 2020-0932260 dated Apr. 20, 2021.
Non-Final Office Action for U.S. Appl. No. 16/566,393 dated May 11, 2021.
Amendment Response to NFOA for U.S. Appl. No. 16/566,393 dated Aug. 11, 2021.
Non Final Office Action for U.S. Appl. No. 16/594,259 dated Aug. 31, 2021.
Amendment Response to Non-Final Office Action for U.S. Appl. No. 16/183,171 dated Jul. 30, 2020.
Amendment Response to Non-Final Office Action for U.S. Appl. No. 16/183,162 dated Jul. 30, 2020.
Applicant Interview Summary for U.S. Appl. No. 16/096,031 dated Jul. 30, 2020.
Applicant Interview Summary for U.S. Appl. No. 16/169,334 dated Jul. 30, 2020.
Applicant Interview Summary for U.S. Appl. No. 16/183,133 dated Aug. 24, 2020.
Non-Final Office Action for U.S. Appl. No. 16/183,149 dated Aug. 18, 2020.
Extended European Search Report for EP Patent Application No. 20185092.2 dated Sep. 11, 2020.
EP Examination Report for EP Patent Application No. 18745794.0 dated Jul. 20, 2020.
Amendment Response to NFOA for U.S. Appl. No. 16/183,149 dated Sep. 25, 2020.
Notice of Allowance for U.S. Appl. No. 16/183,149 dated Oct. 9, 2020.
Foreign OA for CN Patent Application No. 2017800393642, dated Dec. 1, 2020.
Foreign OA for CN Patent Application No. 2017800393676, dated Dec. 2, 2020.
Foreign OA for CN Patent Application No. 2017800396566, dated Dec. 3, 2020.
Foreign OA for CN Patent Application No. 2017800343357, dated Jan. 6, 2021.
Foreign Response for EP Patent Application No. 18807524.6, dated Dec. 21, 2020.
PCT International Search Report and Written Opinion for International Application No. PCT/US2020/014854, dated Oct. 5, 2020 (13 pages).
PCT International Search Report and Written Opinion for International Application No. PCT/US2020/018655, dated Dec. 16, 2020 (22 pages).
PCT International Search Report and Written Opinion for International Application No. PCT/US2020/017684, dated Nov. 30, 2020 (19 pages).
Foreign OA for JP Patent Application No. 2019-507078 dated Feb. 3, 2021.
Foreign OA for JP Patent Application No. 2019-507075 dated Feb. 1, 2021.
Notice of Allowance for U.S. Appl. No. 16/397,089 dated Feb. 18, 2021.

Foreign OA for JP Patent Application No. 2018-562633 dated Mar. 4, 2021.
Foreign Response for EP Patent Application No. 21211363.3 dated Mar. 17, 2022.
Foreign Exam Report for IN Patent Application No. 202147016629 dated Mar. 2, 2022.
Foreign OA for IN Patent Application No. 202147016649 dated Mar. 28, 2022.
Non-Final Office Action for U.S. Appl. No. 16/707,045 dated Apr. 11, 2022.
Foreign OA for CN Patent Application No. 2017800670344 dated Mar. 21, 2022 with English Translation.
Foreign OA for JP Patent Application No. 2021-072088 dated Apr. 5, 2022 with English translation.
Foreign OA for EP Patent Application No. 19726855.0 dated May 18, 2022.
Foreign OA for CN Patent Application No. 201780067034.4 dated Sep. 3, 2021 (with English translation).
Foreign Search Report for CN Patent Application No. 201780067034.4 dated Aug. 30, 2021 (with English translation).
Response to OA for EP Patent Application No. 19773654.9 dated Dec. 22, 2021 with Amended Claims and Description.
Extended European Search Report for EP Patent Application No. 21192438.6 dated Nov. 23, 2021.
Foreign Notice of Rejection for JP Patent Application No. 2020-093260 dated Dec. 21, 2021.
Non-Final Office Action for U.S. Appl. No. 15/496,570 dated Aug. 9, 2017.
PCT International Search Report and Written Opinion for International Application No. PCT/US2017/029440, Applicant Stryker Corporation, dated Jul. 7, 2017.
PCT Invitation to Pay Additional Fees for International Application No. PCT/US2017/029366, Applicant Stryker Corporation, dated Jul. 7, 2017.
PCT International Search Report and Written Opinion for International Application No. PCT/US2017/029472, Applicant Stryker Corporation, dated Jul. 7, 2017.
PCT International Search Report and Written Opinion for International Application No. PCT/US2017/0355543, Applicant Stryker Corporation, dated Aug. 14, 2017.
PCT International Search Report and Written Opinion for International Application No. PCT/US2017/029366, Applicant Stryker Corporation, dated Aug. 29, 2017.
PCT Invitation to Pay Additional Fees for International Application No. PCT/US2017/029345, Applicant Stryker Corporation dated Oct. 17, 2017.
Non-Final Office Action for U.S. Appl. No. 15/496,786 dated Nov. 1, 2017.
PCT International Search Report and Written Opinion for International Application No. PCT/US2017/050933, Applicant Stryker Corporation, forms PCT/ISA/210,220, and 237, dated Nov. 10, 2017 (16 pages).
Response to Non-Final Office Action for U.S. Appl. No. 14/496,786, filed Feb. 1, 2018.

207
puller (pull wire)

205
guide catheter
pulled back 201
catheter (resists
buckling up to at
least >= 200 g)

203
inverted knitted
tractor tube 211
lubricious liner
wrapping around
catheter tip 207
puller (pull wire)

205
guide catheter
pulled back 201
catheter (resists
buckling up to at
least >= 200 g)

203
Inverted knitted
tractor tube 211
lubricious liner
wrapping around
catheter tip

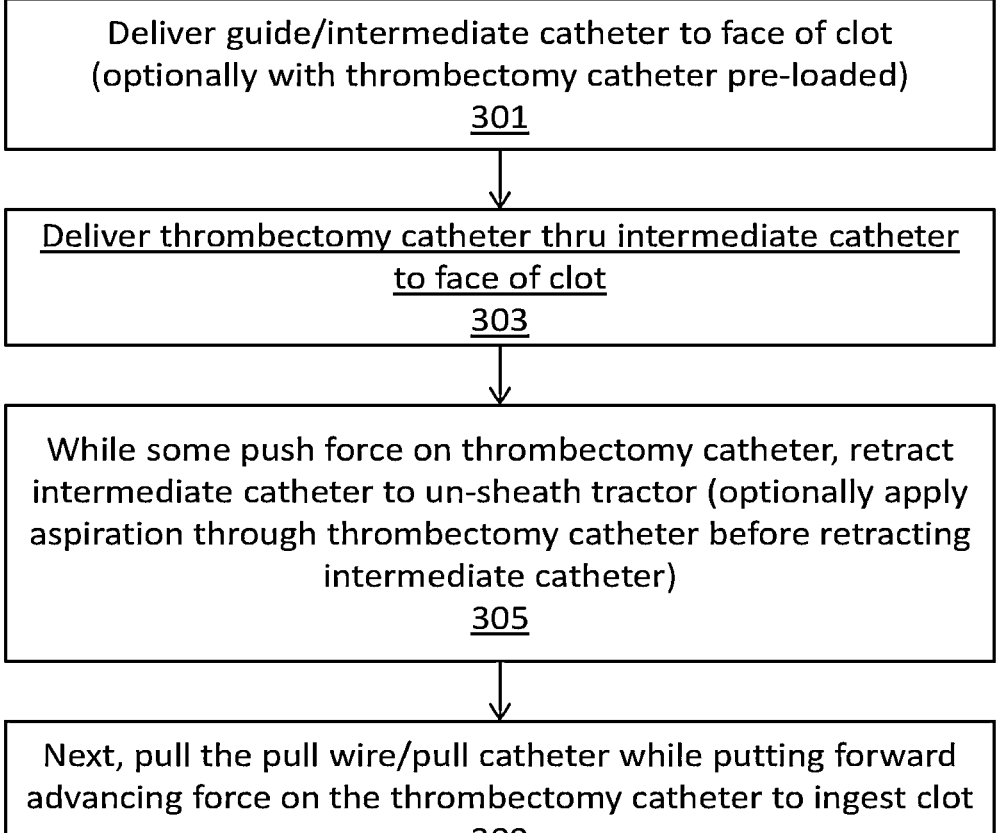

Deliver guide/intermediate catheter to face of clot
(optionally with thrombectomy catheter pre-loaded)
301

Deliver thrombectomy catheter thru intermediate catheter
to face of clot
303

While some push force on thrombectomy catheter, retract
intermediate catheter to un-sheath tractor (optionally apply
aspiration through thrombectomy catheter before retracting
intermediate catheter)
305

Next, pull the pull wire/pull catheter while putting forward
advancing force on the thrombectomy catheter to ingest clot
309

FIG. 3

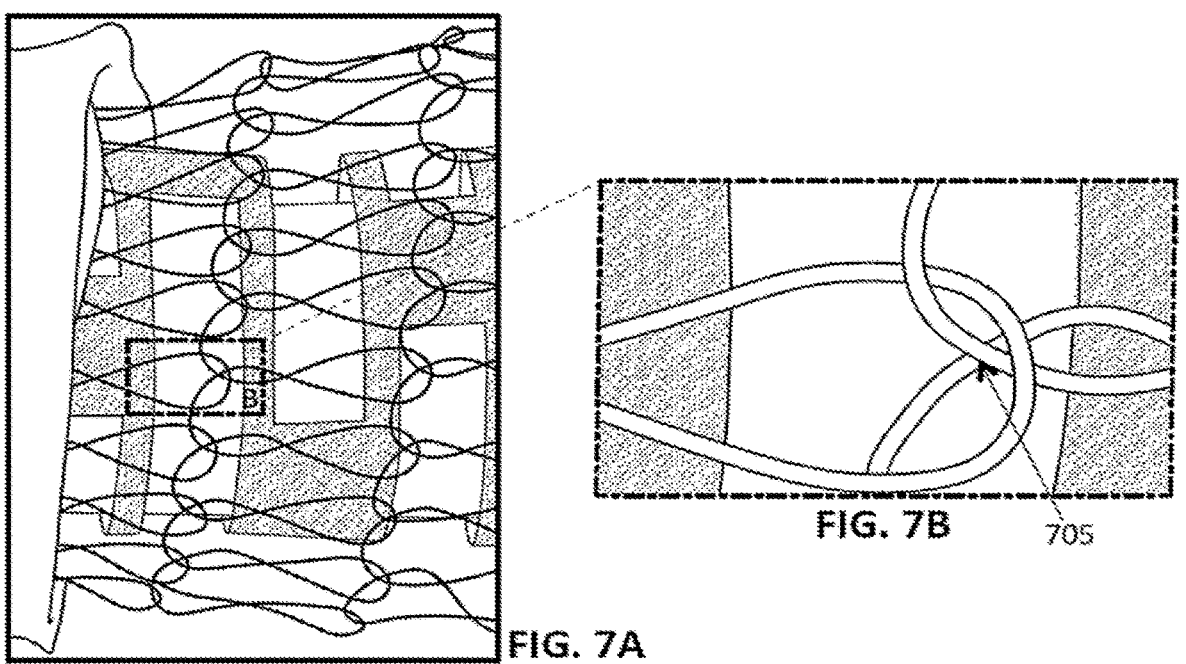
FIG. 7A
FIG. 7B                705
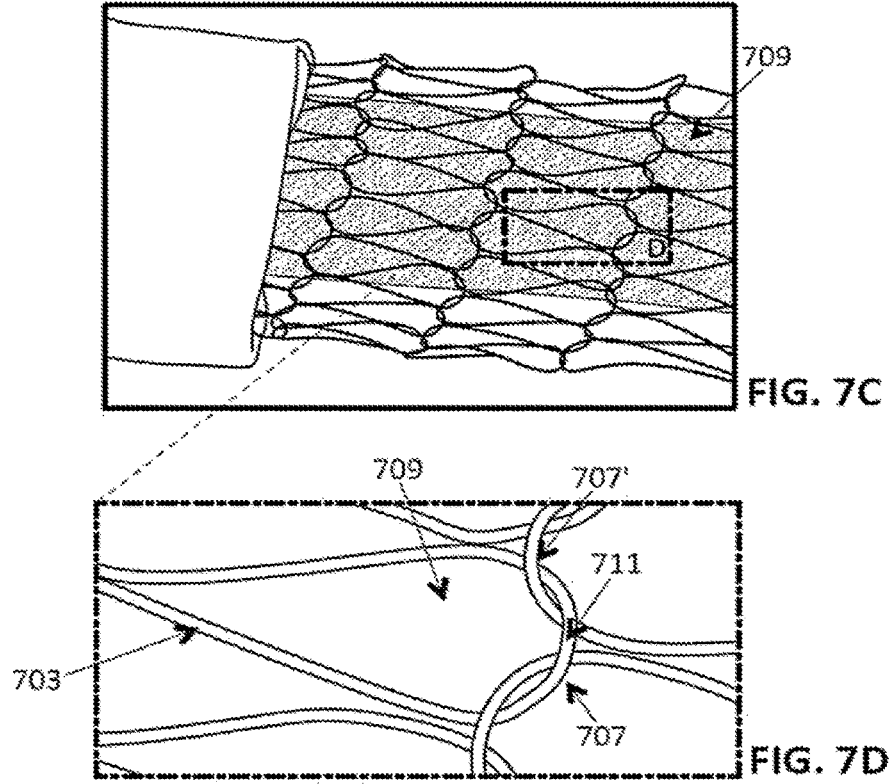
709
FIG. 7C
709          707'
711
703
707
FIG. 7D

713

721

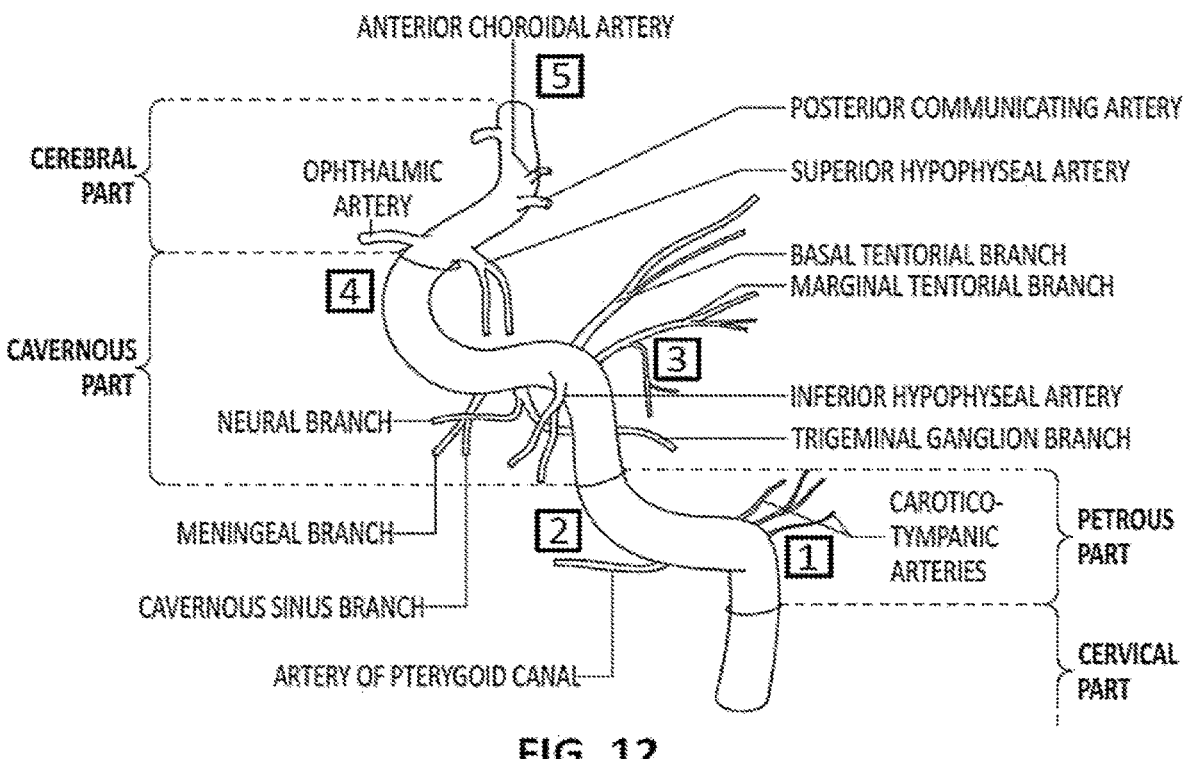
FIG. 12
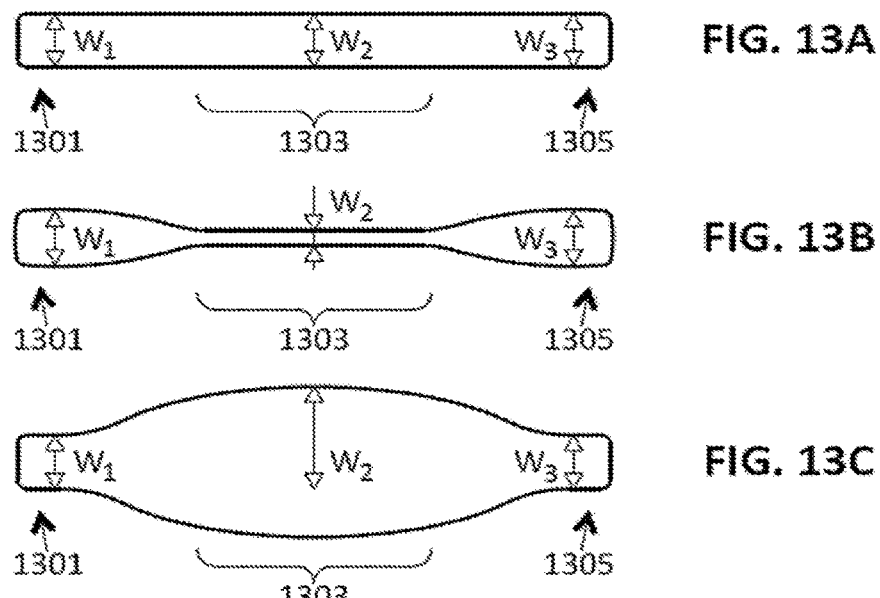
FIG. 13A
FIG. 13B
FIG. 13C

LASER CUT PATTERN W/85A
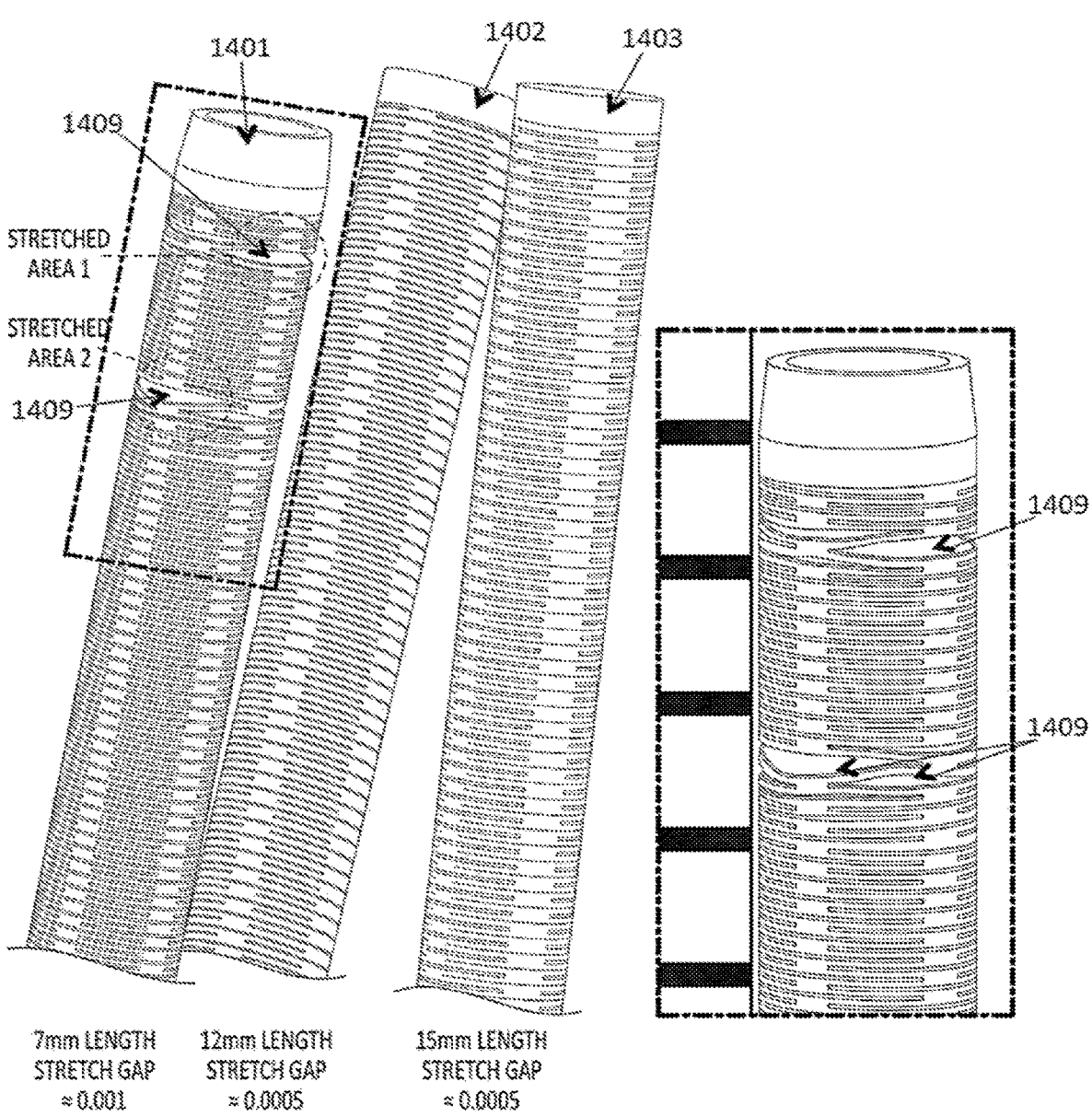
7mm LENGTH
STRETCH GAP
≈ 0.001
12mm LENGTH
STRETCH GAP
≈ 0.0005
15mm LENGTH
STRETCH GAP
≈ 0.0005
FIG. 14A      FIG. 14B

| HYPOTUBE DESIGN | | | | | | | | | |
|---|---|---|---|---|---|---|---|---|---|

| TUBING MATERIAL: NITINOL | | | | TUBING SIZE: .057x.052 | | | | | |
|---|---|---|---|---|---|---|---|---|---|
| CUTS PER ROTATION: 2.5 | | | | CUT ANGLE: 121 | | | UNCUT ANGLE: 23 | | |

| ZONE | 1 | 2 | 3 | 4 | 5 | 6 | 7 | 8 | 9 |
|---|---|---|---|---|---|---|---|---|---|
| PITCH | 0 | 0.003 | 0.0035 | 0.004 | 0.0045 | 0.005 | 0.008 | 0.01 | 0.013 |
| LENGTH | 0.025 | 2 | 8 | 4 | 4 | 6 | 3 | 2 | 26 |

DESIGN W/ 80A
(WHERE THE DISTAL 5MM IS STRETCHED 8MM + TWO DEFECTS)

DEFECTS
1509

Ø 4mm

BCM 002x003
55D STRIKE
1.5cm 40D
15 cm 55D, 400grm

UNDER ≈ 300g
TENSION

"X" — RANGES FROM 1 – 50mm
— PREFERED 2 – 10mm OR 2 – 5mm

OPEN             CLOSED
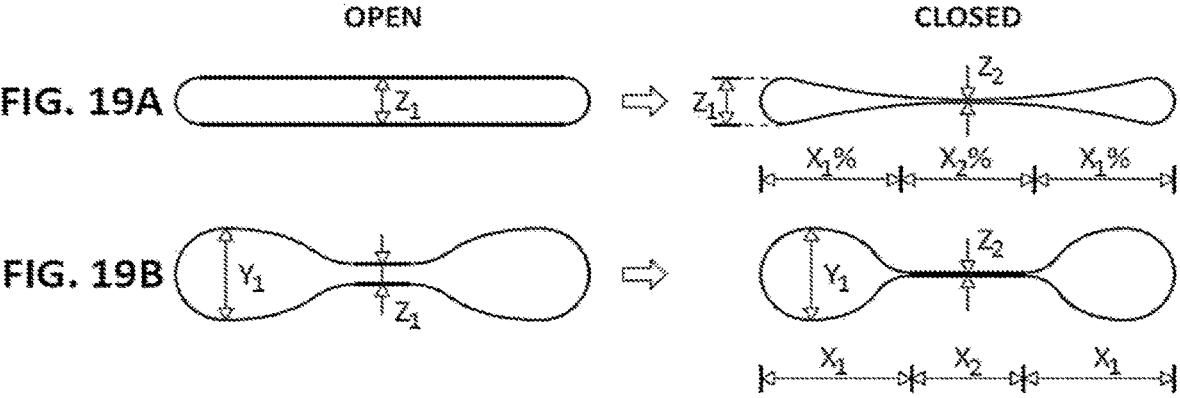
FIG. 19A
FIG. 19B
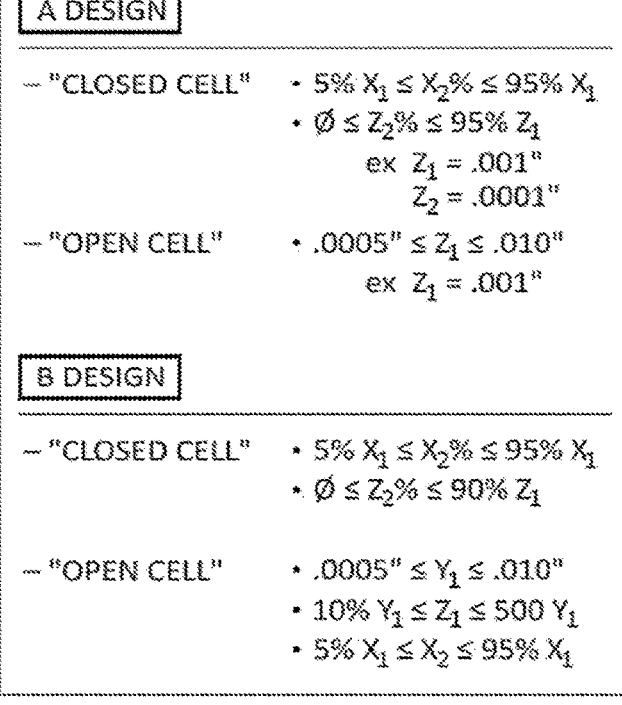
A DESIGN
— "CLOSED CELL"    • $5\% X_1 \leq X_2\% \leq 95\% X_1$
                     • $\emptyset \leq Z_2\% \leq 95\% Z_1$
                        ex $Z_1 = .001"$
                            $Z_2 = .0001"$
— "OPEN CELL"    • $.0005" \leq Z_1 \leq .010"$
                     ex $Z_1 = .001"$
B DESIGN
— "CLOSED CELL"    • $5\% X_1 \leq X_2\% \leq 95\% X_1$
                       • $\emptyset \leq Z_2\% \leq 90\% Z_1$
— "OPEN CELL"    • $.0005" \leq Y_1 \leq .010"$
                     • $10\% Y_1 \leq Z_1 \leq 500 Y_1$
                     • $5\% X_1 \leq X_2 \leq 95\% X_1$
FIG. 19C
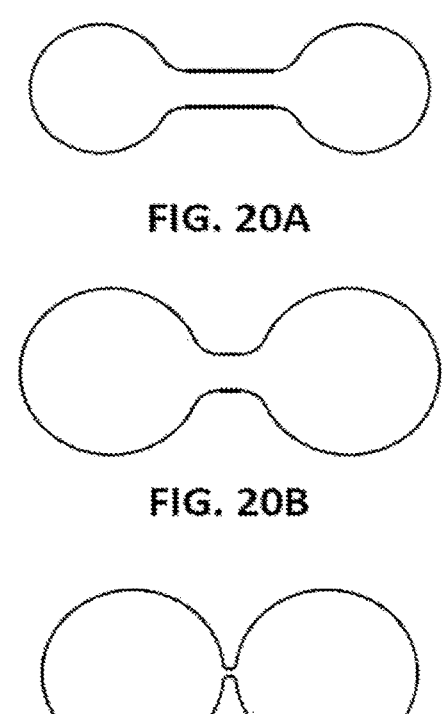
FIG. 20A
FIG. 20B
FIG. 20C

2101

2103

2103'''

2103

2103''

2103'

2201

2203

2301

2303

2303''''
2303
2303''
2303'

2501

2503

2503″

2503′

2503

Crushed Spiral          Crushed Brick          Open Brick (5mm)          NiTi Ring to
                        (2mm)                                            Emulate Pt marker Ø 4mm

TRADITIONAL CATHETER
BUCKLES & FAILS

880 CATHETER
NO BUCKLING

100g

500g

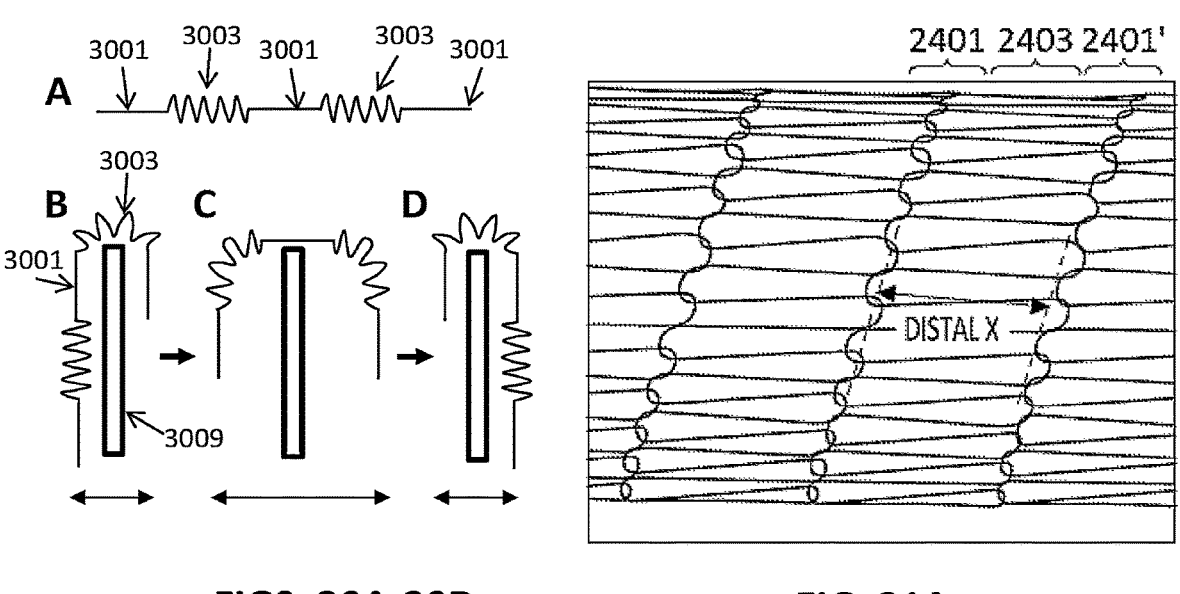
FIGS. 30A-30D          FIG. 31A
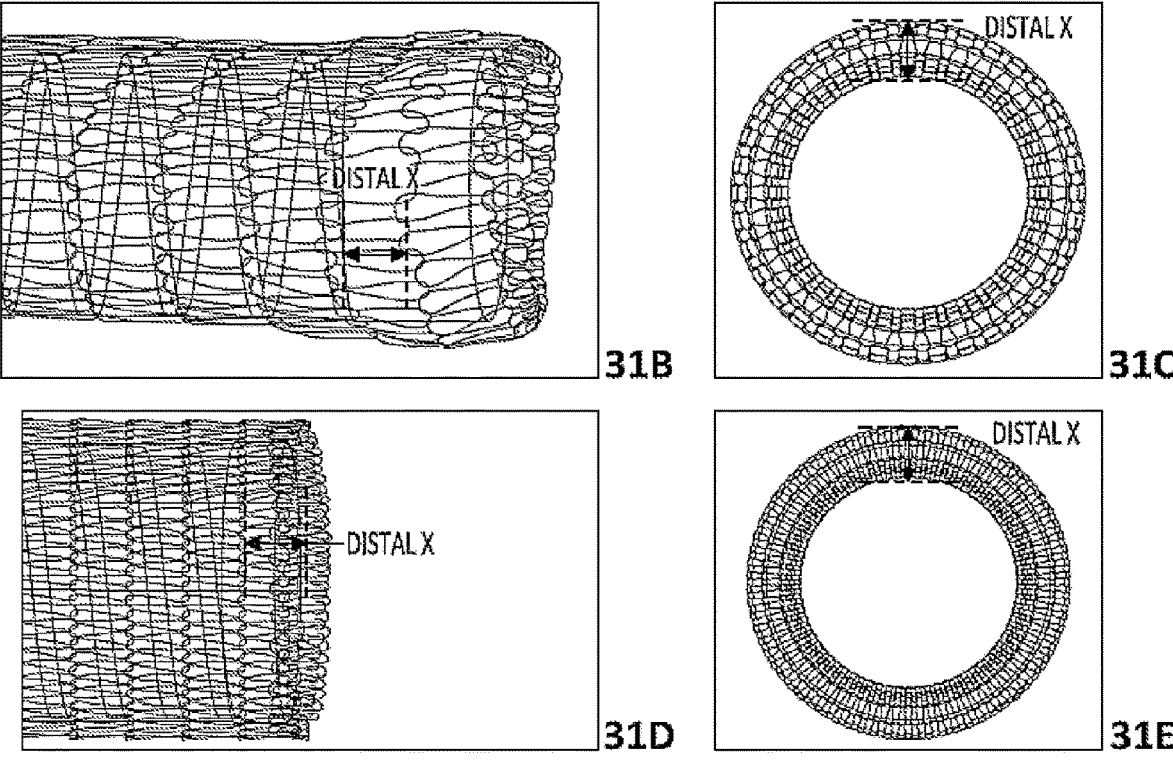
FIGS. 31B-31E

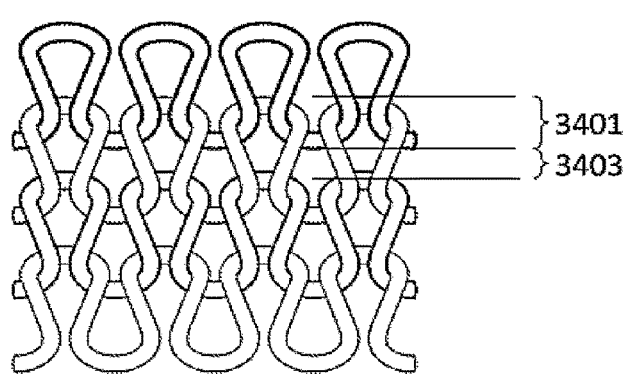
} 3401
} 3403
FIG. 34
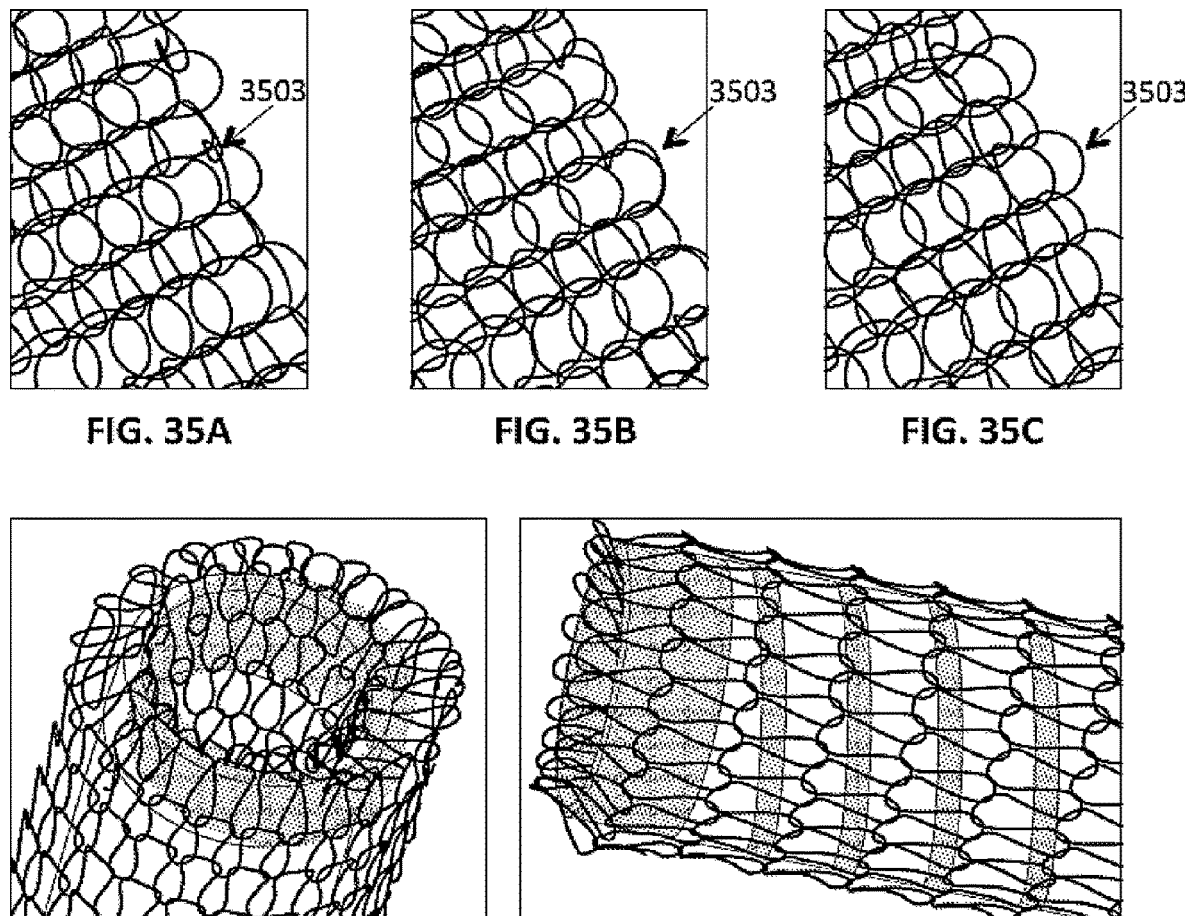
FIG. 35A          FIG. 35B          FIG. 35C
FIG. 36A                FIG. 36B

3703

3703

3703

INVERTING THROMBECTOMY APPARATUSES AND METHODS

CROSS REFERENCE TO RELATED APPLICATIONS

This patent application is a continuation of U.S. application Ser. No. 17/986,680, filed Nov. 14, 2022, which claims priority to U.S. application Ser. No. 16/731,649, filed Dec. 31, 2019 and issued as U.S. Pat. No. 11,497,512, which is a continuation-in-part of PCT Application No. PCT/US2018/040937, filed Jul. 5, 2018, which claims priority to U.S. Provisional Application No. 62/529,386, filed Jul. 6, 2017. This patent application is also a Continuation-in-part of U.S. patent application Ser. No. 16/096,031, filed Oct. 24, 2018, which is a U.S. national phase entry of PCT Application No. PCT/US2017/029345, filed Apr. 25, 2017, which claims priority to each of U.S. Provisional Application Nos. 62/327,024, filed Apr. 25, 2016, 62/345,152, filed Jun. 3, 2016, and 62/393,460, filed Sep. 12, 2016.

INCORPORATION BY REFERENCE

All patents and patent applications mentioned in this specification, are herein incorporated by reference in their entirety to the same extent as if each individual publication or patent application was specifically and individually indicated to be incorporated by reference.

FIELD

The apparatuses and methods disclosed and described herein relate to mechanical removal of objects from within a body lumen, such as a blood vessel. In particular, disclosed and described herein are mechanical thrombectomy apparatuses and methods of using same.

BACKGROUND

Many vascular problems stem from insufficient blood flow through blood vessels. One causes of insufficient or irregular blood flow is a blockage within a blood vessel referred to as a blood clot, or thrombus. Thrombi can occur for many reasons, including after a trauma such as surgery, or due to other causes. For example, a large percentage of the more than 1.2 million heart attacks in the United States are caused by blood clots (thrombi) which form within a coronary artery. It is often desirable to remove tissue from the body in a minimally invasive manner as possible, so as not to damage other tissues. For example, removal of tissue, such as blood clots, from within a patient's vasculature may improve patient conditions and quality of life.

When a thrombus forms, it may effectively stop the flow of blood through the zone of formation. If the thrombus extends across the interior diameter of an artery, it may cut off the flow of blood through the artery. If one of the coronary arteries is 100% thrombosed, the flow of blood is stopped in that artery, resulting in a shortage of oxygen carrying red blood cells. e.g., to supply the muscle (myocardium) of the heart wall. Such a thrombosis is unnecessary to prevent loss of blood but can be undesirably triggered within an artery by damage to the arterial wall from atherosclerotic disease. Thus, the underlying disease of atherosclerosis may not cause acute oxygen deficiency (ischemia) but can trigger acute ischemia via induced thrombosis. Similarly, thrombosis of one of the carotid arteries can lead to stroke because of insufficient oxygen supply to vital nerve centers in the cranium. Oxygen deficiency reduces or prohibits muscular activity, can cause chest pain (angina pectoris), and can lead to death of myocardium which permanently disables the heart to some extent. If the myocardial cell death is extensive, the heart will be unable to pump sufficient blood to supply the body's life sustaining needs. The extent of ischemia is affected by many factors, including the existence of collateral blood vessels and flow which can provide the necessary oxygen.

Clinical data indicates that clot removal may be beneficial or even necessary to improve outcomes. For example, in the peripheral vasculature, interventions and procedures can reduce the need for an amputation by as much as 80 percent. The ultimate goal of any modality to treat these conditions of the arterial or venous system is to remove the blockage or restore patency, quickly, safely, and cost effectively. This may be achieved by thrombus dissolution, fragmentation, thrombus aspiration or a combination of these methods.

Depending on the size, location and extent of a clot, it may be particularly advantageous to employ a mechanical thrombectomy device to remove the clot in a manner that is both safe and effective. Described herein are mechanical thrombectomy apparatuses (devices, systems and kit) and methods of using and making such apparatuses that may address the needs and problems discussed above.

SUMMARY OF THE DISCLOSURE

Disclosed and described herein are mechanical thrombectomy apparatuses (devices, systems, etc.) and methods of using and making them. In particular, described herein are mechanical thrombectomy apparatuses having improved rolling/inverting which may be particularly well adapted for removing large and hard clots, and/or difficult to grasp clots, from within a vessel. The disclosed and described apparatuses may include a low-friction (or friction-reducing) sleeve, one or more adaptations (e.g., chamfers, etc.) in the elongate inversion support catheter for pulling in larger clots, and knitted tractor tubes having woven links that are optimized for grabbing and compressing large clots without jamming. Also disclosed and described herein are mechanical thrombectomy apparatuses that may be reusable. In particular, disclosed and described herein are mechanical thrombectomy apparatuses that include an elongate inversions support catheter over which the tractor (also referred to herein as a tractor tube, or an inverting tube) may be pulled to invert; these inversion support catheters may be configured so that they have a high degree of flexibility, but also a very high column strength.

For example, in some variations, the mechanical thrombectomy apparatuses disclosed and described herein are inverting tractor thrombectomy apparatuses that includes a tractor tube (e.g., tractor tube, inverting tube, etc.) comprising a flexible tube of material that inverts over itself as it rolls over a distal end opening of an elongate inversion support. In some variations this tractor tube may be knitted, and may be configured (e.g., sized, oriented, etc) to roll smoothly over the distal end opening of the elongate inversion support catheter.

The elongate inversion support typically comprises a catheter having a distal end opening into which the tractor inverts. The flexible tractor inverts and rolls back into itself and may be drawn into the elongate inversion support in a conveyor-like motion; the outward-facing region rolls around to become an inward-facing region, e.g., within the lumen of the elongate inversion support. The rolling motion may thus draw a clot or other object within a vessel into the elongate inversion support.

A knitted tractor tube may be configured to roll into the distal end opening of the elongate inversion support catheter without jamming by being oriented in an inverted knit, so that the adjacent rows of links are connected with the loops interlocking so that when the tube is inverted into itself, the loops are free to swing outward from the tube and are not held in place. For example, the loops of the knit are configured so that they pass under/over then over/under two loops of the adjacent rows. This arrangement may be configured as an "inverted knit" as most knitting machines will produce a tube that is woven in an over/under than under/over pattern.

For example, disclosed and described herein are mechanical thrombectomy apparatuses for removing a clot from a vessel, the apparatus may include: an elongate inversion support catheter having a distal end and a distal end opening; an elongate puller extending within the elongate inversion support catheter; and a knitted tractor tube extending over an outer surface of the elongate inversion support catheter, inverting into the distal end opening of the elongate inversion support catheter, and attached to the elongate puller at a first end within the elongate inversion support catheter, wherein the portion of the knitted tractor tube extending over the outer surface of the elongate inversion support catheter comprises a wire (e.g. a single wire or multiple wires) forming a helical spiral of alternating (e.g., alternating extending proximally to distally and distally to proximally) teardrop-shaped links each having a rounded apex, wherein each link is connected to two adjacent links so that the apex of each link is on an outward-facing surface of the tractor tube, wherein the links flare outward from an outer wall of the elongate inversion support catheter when the puller is pulled proximally within the elongate inversion support catheter.

Any of these apparatuses may include a lubricious liner sleeve extending from within the elongate inversion support catheter and over the distal end opening of the elongate inversion support catheter. The pull force required to roll the knitted tractor tube over the distal end of the elongate inversion support catheter and into the elongate inversion support catheter may be less than about 250 g of force (e.g., less than about 225 g of force, less than about 215 g of force, less than about 200 g of force, less than about 190 g of force, less than about 175 g of force, less than about 150 g of force, less than about 125 g of force, less than about 100 g of force, etc.). e.g. by pulling the puller proximally to pull the tractor tube proximally into the inversion support catheter so that it rolls over and against the distal end opening of the inversion support catheter.

The lubricious liner may be, for example, a PTFE liner wrapping around the open distal end of the elongate inversion support catheter.

The knitted tractor tube may be formed of an alloy of nickel titanium.

In any of the apparatuses disclosed and described herein may be configured to easily roll over the distal end of the inversion support catheter while still extending outward to grab and pull the clot. For example, the links may have a length of L, and a grab width of W when flaring outward from the outer wall of the elongate inversion support catheter when the puller is pulled proximally, wherein W is between 30-90% of L (e.g., between 45% and 85%, of L, between 50% and 81%, etc). The distal open end of the elongate inversion support catheter may be tapered, instead or in addition to using a lubricious sleeve.

The knitted tractor tube may include a second end (e.g., the proximal end that is pulled distally) that is unattached and free to slide over the outer surface of the elongate inversion support catheter. The second end may include a stop that is configured to prevent the second end from inverting over the distal end of the elongate inversion support catheter.

For example, disclosed and described herein are mechanical thrombectomy apparatuses for removing a clot from a vessel, the apparatus comprising: an elongate inversion support catheter having a distal end and a tapered or rounded distal end opening; an elongate puller extending within the elongate inversion support catheter; and a knitted tractor tube extending over an outer surface of the elongate inversion support catheter, inverting into the distal end opening of the elongate inversion support catheter, and attached to the elongate puller at a first end within the elongate inversion support catheter, wherein the portion of the knitted tractor tube extending over the outer surface of the elongate inversion support catheter comprises a wire forming a helical spiral of alternating teardrop shaped-links each having a rounded apex, wherein each link is connected to two adjacent links so that the apex of each link is on an outward-facing surface of the tractor tube, wherein the links flare outward from an outer wall of the elongate inversion support catheter when the puller is pulled proximally within the elongate inversion support catheter, further wherein the links have a length of L, and a grab width of W when flaring outward from the outer wall of the elongate inversion support catheter when the puller is pulled proximally, wherein W is between 30-90% of L.

Also disclosed and described herein are methods of removing a clot from a vessel using an apparatus (e.g., device or system) such as those described above. For example, a method of removing a clot from a vessel may include: positioning the distal-facing end of the apparatus adjacent to the clot, and pulling the first end of a knitted tractor tube proximally (e.g., by pulling proximally on a puller attached to the tractor tube), so that the portion of the knitted tractor tube extending over the outer surface of the elongate inversion support catheter that forms a helical spiral of alternating teardrop-shaped links each having a rounded apex, wherein each link is connected to two adjacent links so that the apex of each link is on an outward-facing surface of the tractor tube, roll over the distal end of the device and invert so that the links flare outward from an outer wall of the elongate inversion support catheter when the puller is pulled proximally. The teardrop shaped arms may roll by seesawing over the open distal end of the inversion support catheter and swing outward with a lever arm force may grasp the clot and pull it into the device.

Also disclosed and described herein are mechanical thrombectomy apparatuses for removing a clot from a vessel that include an elongate slotted inversion support catheter having a distal end and a distal end opening, wherein the elongate inversion support catheter comprises a spiral pattern having a plurality of slots arranged approximately transversely to a long axis of the elongate slotted inversion support catheter, wherein the slots have an open diameter of about 0.001 inches or less and wherein there are between 2 and 4 slots per circumferential turn of the spiral pattern; and a tractor tube extending over an outer surface of the elongate inversion support catheter, inverting into the distal end opening of the elongate inversion support catheter; wherein the tractor tube is configured to invert over the distal end opening of the elongate inversion support catheter when pulled proximally into the elongate inversion support catheter.

In any of these apparatuses a second region of the elongate slotted inversion support catheter may be included and may comprise a second spiral pattern having a second plurality of slots arranged approximately transversely to the long axis of the elongate slotted inversion support catheter, wherein the second plurality of slots have an open diameter of about 0.001 inches or more and wherein there are between 2 and 4 slots per circumferential turn of the spiral pattern. The second region may be adjacent to the first region and may be distally of the first region. Alternatively, the second region may be proximal to the first region.

Any of these apparatuses may include a puller that extends within the elongate inversion support catheter to which a first end of the tractor tube is attached.

In any of the apparatuses disclosed and described herein, there may be between 2 and 3 slots per circumferential turn (e.g., on average 2.5 slots). The spiral pattern may be helically arranged around the circumference of the elongate slotted inversion support catheter. The slotted inversion support catheter may be heat set into a compressed configuration so that the slots form closed cells in a relaxed configuration. The slots may extend between about 50 and 98% of each circumferential turn of the spiral pattern. In some variations, at least 1 mm of the distal end of the slotted inversion support catheter comprises the spiral pattern.

The spiral pattern may be configured so that at least 80% of a length of the slots contact and are supported by an opposite side of the slots when the elongate slotted inversion support catheter is longitudinally compressed. E.g., at least 85%, at least 90%, at least 95%, etc.). The slots may be rectangular. The elongate slotted inversion support catheter has a catheter compression yield force of greater than about 1000 g. The elongate slotted inversion support catheter may be one or both of: a nickel titanium alloy and stainless steel.

For example, a mechanical thrombectomy apparatus for removing a clot from a vessel may include: an elongate slotted inversion support catheter having a distal end and a distal end opening, a first region of the elongate inversion support catheter comprising a plurality of slots arranged approximately transversely to a long axis of the elongate slotted inversion support catheter, wherein the slots have an open diameter of about 0.001 inches or less and wherein there are between 2 and 4 slots per circumferential turn about the long axis; a second region of the elongate slotted inversion support catheter comprises a second plurality of slots arranged approximately transversely to the long axis of the elongate slotted inversion support catheter, wherein the second plurality of slots have an open diameter of about 0.001 inches or more and wherein there are between 2 and 4 slots per circumferential turn about the long axis; a tractor tube extending over an outer surface of the elongate inversion support catheter, inverting into the distal end opening of the elongate inversion support catheter; and a puller within the elongate slotted inversion support catheter, wherein a first end of the tractor tube is attached to the puller; wherein the tractor tube is configured to invert over the distal end opening of the elongate inversion support catheter when pulled proximally into the elongate inversion support catheter.

Also disclosed and described herein are methods of removing a clot from a vessel using any of these apparatuses, including an apparatus having an elongate slotted inversion support catheter having a distal end and a distal end opening, a first region of the elongate inversion support catheter comprising a plurality of slots arranged approximately transversely to a long axis of the elongate slotted inversion support catheter, wherein the slots have an open diameter of about 0.001 inches or less and wherein there are between 2 and 4 slots per circumferential turn about the long axis; a second region of the elongate slotted inversion support catheter comprises a second plurality of slots arranged approximately transversely to the long axis of the elongate slotted inversion support catheter, wherein the second plurality of slots have an open diameter of about 0.001 inches or more and wherein there are between 2 and 4 slots per circumferential turn about the long axis; a tractor tube extending over an outer surface of the elongate inversion support catheter. The method may include guiding the elongate slotted inversion support catheter through the patient's tortious vasculature by bending the second region more than the first region, e.g., by pushing it over a guidewire, etc.

BRIEF DESCRIPTION OF THE DRAWINGS

The various features and aspects of the inventions disclosed and described herein are set forth with particularity in the claims that follow. A better understanding of the features and advantages of the disclosed and described apparatuses and methods will be obtained by reference to the following detailed description when read with the accompanying drawings, of which:

FIG. 1A shows an example of an elongate inversion support catheter portion of an apparatus. At least the distal end of the elongate inversion support is configured as a catheter. FIG. 1B shows an enlarged view of a partial section of a distal end (opening) of the catheter of the elongate inversion support of FIG. 1A, showing the aperture formed by the distal end opening; FIG. 1C shows an example of a flexible tractor tube attached over a puller (the puller in this example is configured as a catheter). The tractor is shown in a first configuration. In some variations, the flexible tractor tube may be biased open, e.g., by heat setting, to have an outer diameter that is greater than the inner diameter of the catheter of the elongate inversion support, as shown in FIG. 1D. FIG. 1D shows the same distal tractor region of FIG. 1C with the expandable first end region expanded. This first configuration may be compressed down into the elongate inversion support and the distal end inverted over the catheter portion of the elongate inversion support, as shown in FIG. TE. In FIG. 1E, the assembled mechanical thrombectomy apparatus includes an elongate inversion support catheter having a distal end and a distal end opening; the elongate puller extends within the elongate inversion support catheter and a flexible tractor tube is connected at one end to the elongate puller. The flexible tractor tube and puller may be extended through the elongate inversion support catheter, including extended out of the distal end (e.g., by pulling the elongate inversion support catheter proximally and/or by pushing the elongate puller distally). The flexible tractor tube may initially be held in a collapsed first configuration (as shown in FIG. 1E) for positioning within a vessel; it may be deployed and expanded, as shown in FIG. 1F, with the elongate inversion support catheter positioned between the flexible tractor tube and the elongate puller. The flexible tractor tube may be biased so that in the second configuration (inverted over the distal end of the catheter), the tractor has a 'relaxed' outer diameter that is greater than the outer diameter of the catheter of the elongate inversion support.

FIGS. 1G and 1H illustrate the use of an apparatus such as the one shown in FIGS. 1E and 1F to remove a clot by drawing the flexible tractor tube proximally and/or advancing the catheter distally towards the clot so that the expandable first end region inverts as it is drawn into the distal end of the catheter, pulling the clot into the catheter.

In FIG. 1I, the tractor is shown attached to the distal end of a tapered or narrow puller; the distal end region is tapered, and includes a radiopaque marker at or near the attachment site to the tractor; the tractor may be knitted, braided, woven, etc. Thus, in some variations the distal end region of the puller may have a greater flexibility than the proximal end of the puller. The puller may be hollow (e.g., a catheter or hypotube) or solid (e.g., like a wire).

In FIG. 2A, the apparatus includes a lubricious liner that is inverted over the distal end opening of the elongate inversion support catheter. FIG. 3 is a flowchart illustrating the method shown in FIG. 2A.

FIG. 3 is a schematic illustrating a method of operating a mechanical thrombectomy apparatus such as the one shown in FIG. 2A.

In FIG. 5, the loops forming the knit are interlocked, but may swing outward as the knit is rolled over the distal end opening of the elongate inversion support catheter, which may knead and/or masticate the clot, aiding in pulling it into the elongate inversion support catheter.

FIGS. 7A and 7B show an example of a knit tractor tube that undesirably includes regions where adjacent links of the knit include triple crossover points, e.g., as shown in greater detail in FIG. 7B. Typically, when the diameter of the knitted tractor tube is greater than the outer diameter of the elongate inversion support catheter such that the adjacent links form triple cross-over points, as shown in FIG. 7B, the resulting tractor tube may roll less smoothly (and/or may jam) over the distal end opening of the elongate inversion support catheter. In contrast. FIGS. 7C and 7C shows an example of a knitted tractor tube having only double overlaps, which may more desirably roll over the elongate inversion support catheter. In FIG. 7D, an enlarged view of the links of the woven tractor tube is shown.

FIG. 7F is an enlarged view of FIG. 7E.

In FIG. 9A, the apparatus includes a distal tractor stop/grip portion that prevents the tractor tube from inverting fully into the elongate inversion support catheter. Once the clot is pulled into the elongate inversion support catheter as shown in FIG. 9B, the apparatus may be removed from the body, and the clot ejected, e.g., by sliding the tractor tube along the outer diameter of the elongate inversion support catheter, as shown in FIG. 9C. The apparatus may then be re-used.

FIG. 10A show an example in which the elongate puller is adapted to include a nose region at the distal end, including a bumper. The distal nose region/bumper may extend out from the elongate inversion support catheter until the target location, near the clot, has been reached, and then retracted proximally to roll the tractor tube into the elongate inversion support catheter. FIG. 1B is another example in which the puller (e.g. pull wire or pull catheter) is slidable within a collar coupled to the tractor tube, but further includes an engagement region at or near the distal end of the puller that engages the collar and allows the puller to pull the tractor tube proximally in the elongate inversion support catheter to roll the tractor tube into the elongate inversion support catheter. FIG. 10C is another example in which the puller is a pull wire having a collar region near the distal end through which a guidewire may pass.

FIG. 11A shows a puller (which may be solid or cannulated) having a distal tip region that includes a plurality of flanges or edges extending therefrom. In FIG. 11A the distal tip includes a plurality of cup-like members extending from therefrom. FIG. 11B shows another example of a puller in which the distal end includes a plurality of projections extending proximally. In FIG. 11B, the projections may be fringe or fibers extending from the outer surface of the distal end of the puller, which may be tapered or cylindrical.

In FIG. 11D, the stepped profile includes a plurality of (e.g., 5) different sized cones connected and arranged from larger (proximal) to smaller (distal). The cones may be separate or solid and fused together.

FIG. 12 is an example of an internal carotid artery, which has a tortious vascular path. This path may be divided up in to sub-regions, and a model of this path may be used to examine tracking of any of the apparatuses disclosed and described herein.

FIGS. 13A to 13C illustrate exemplary rectangular slots hat maybe formed in any of the inversion support catheters described herein. FIG. 13A shows slot that is in a neutral configuration, prior to heat setting in a collapsed or expanded configuration. In FIG. 13A, the slot has a width at the ends ($w_1$) that is approximately the same as the width in a middle region between the ends ($w_2$). In FIG. 13B, the slot has been compressed (e.g, by applying a longitudinal compression force on the catheter into which the slot is cut and heat setting in the compressed state) so that the width of the middle region ($w_2$) is less than the width of the end regions, which are not compressible ($w_1$). FIG. 13C shows a first open configuration, in which the slot has been pulled (e.g. by pulling a catheter in which the slot is formed in the longitudinal direction) to formed an open configuration, in which the middle region has a diameter ($w_2$) that is greater than the diameter of the end regions ($w_1$).

FIG. 14A shows three examples of inversion support catheters having a slotted pattern of cuts. FIG. 14B is an enlarged view of one of the inversion support catheters of FIG. 14A.

FIG. 17D, shown for comparison, is the slotted inversion support catheter shown and described in FIG. 16A-16F, which did not substantially kink or shorten under 400 g of compression.

FIG. 19A illustrates an example of an approximately rectangular slot in an open-cell (left) and closed-cell (right) configuration. FIG. 19B illustrates an example of a lobed slot (e.g., centrally tapered, hourglass-shaped, barbell-shaped) slot in an open-cell and closed-cell configuration. In FIG. 19B, even the closed-cell configuration remains open at the ends, as shown FIG. 19C provides exemplary dimensions of the slots shown in FIGS. 19A and 19B.

FIGS. 20A-20C illustrate examples of bi-lobed slots (e.g., centrally tapered, hourglass-shaped, barbell-shaped) similar to that shown in FIG. 19B.

FIG. 21A shows the repeating cut-out pattern that may be applied to a catheter (e.g., nitinol catheter tube). FIG. 21B shows a side view of the slotted catheter. FIG. 21C shows a perspective view of the slotted catheter.

FIG. 22A shows the repeating cut-out pattern that may be applied to a catheter (e.g., nitinol catheter tube). FIG. 22B shows a side view of the slotted catheter. FIG. 22C shows a perspective view of the slotted catheter.

FIG. 23A shows the repeating cut-out pattern that may be applied to a catheter (e.g., nitinol catheter tube). FIG. 23B shows a side view of the slotted catheter. FIG. 23C shows a perspective view of the slotted catheter.

FIG. 24A shows an alternating spiral/brick pattern. FIG. 24B shows an alternating spiral/dog bone pattern. FIG. 24C show a pattern of spiral/brick/spiral/dog bone/spiral, which may also alternate.

FIG. 25A shows the cut (slot) pattern including a notched, "bump" region that is spaced so as to align with a series of notched bumps in the loan axis of the catheter, when cut in the spiral pattern, as illustrated in FIGS. 25B and 25C. In FIG. 25B a side view of the catheter is shown. FIG. 25C shows a side perspective view of the catheter of FIGS. 25A-25C. Although three longitudinal lines of aligned bumps are shown circumferentially spaced in FIGS. 25B-25C; any number of aligned bumps (e.g., greater than 2, between 1 and 60, etc.) etc.) may be formed by the spiral cut.

FIG. 30A schematically illustrates a portion of a tractor having regions of alternating stiffness. FIGS. 30B-30D illustrate the seesawing motion of a tractor having regions of alternating stiffness.

FIG. 31A is an example of a knitted tractor having regions of alternating stiffness extending in a corkscrewing/helical pattern along the length of the tractor.

FIGS. 31B-31C show side and end views, respectively of an apparatus having a knitted tractor, similar to that shown in FIG. 31A.

FIGS. 31D and 31E show side and end views, respectively of an apparatus having a knitted tractor.

FIG. 34 is a schematic of a knitted tractor. [ ] FIGS. 35A-35C illustrate movement of the loops of a knitted tractor having loops of a nickel titanium filament forming regions having alternating stiffness (arranged down the long axis of the tractor).

FIGS. 36A-36B illustrate end perspective and side perspective views, respectively, or an apparatus having a knitted tractor.

DETAILED DESCRIPTION

In general, disclosed and described herein are mechanical thrombectomy apparatuses having an inverting flexible tractor tube that is configured to invert over an elongate inversion support catheter. One end of the tractor tube may be coupled to a puller (e.g., pull wire, pull catheter, etc.). In particular, disclosed and described herein are apparatuses including one or more adaptations to prevent jamming and/or roll smoothly, particularly when pulling a large and/or hard clot.

In general, a mechanical thrombectomy apparatus for removing a clot from a vessel may be a system, assembly or device including an elongate inversion support catheter having a distal end and a distal annulus (distal end opening), and a flexible tractor assembly including a flexible tractor tube coupled to an elongate puller. The flexible tractor tube is configured to roll and invert over the distal end opening of the elongate inverting support catheter.

In many of the examples disclosed and described herein, the tractor assembly is configured to extend within the elongate inversion support catheter when deployed. Any of these apparatuses may switch between a delivery configuration, e.g., in which the entire tractor assembly may be held within the elongate inversion support catheter prior to deployment, and a deployed configuration, e.g., in which the elongate inversion support catheter is positioned between the flexible tractor tube and the elongate pusher to support the flexible tractor tube as it is pulled into the elongate inversion support catheter distal end opening to roll and invert into the elongate inversion support catheter. In particular, the methods and apparatuses may be configured so that the transition between the delivery configuration and the deployed configuration is robust. For example, as will be described in greater detail herein, any of the apparatuses and methods disclosed and described herein may include an annular bias that enhances the ability of the elongate inversion support catheter to be inserted between the flexible tractor tube and the elongate puller.

Figures 1A, 1B, 1C, 1D:
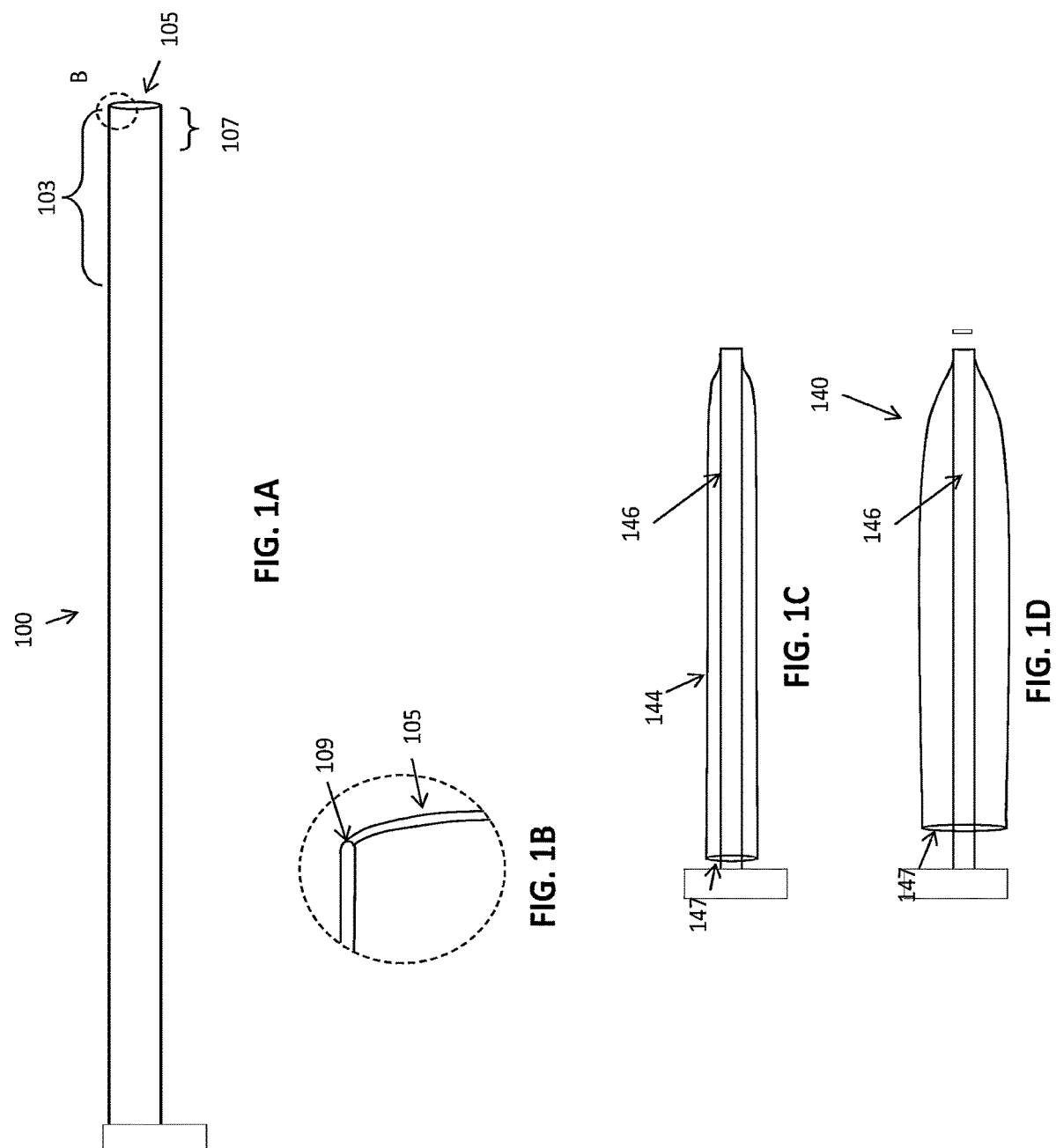
FIGS. 1A-1H illustrate an example of an apparatus for mechanically removing an object such as a clot form a body region.

FIGS. 1A to 1I illustrate various components of a mechanical thrombectomy apparatus that may include any of the features disclosed and described herein. For example, FIG. 1A shows a catheter (e.g., an elongate inversion support catheter) that may form part of the apparatuses disclosed and described herein. In this example, the elongate inversion support catheter includes a catheter body 100 having a distal end region 103 that includes a distal end opening 105. The distal end region may have an increasing softness (measured by durometer, e.g., shore durometer) except that the very distal-most end region (distal end 105, including the distal end opening) may be substantially less soft than the region immediately proximate to it. Thus, although the distal tip region of the catheter (e.g., the distal most x linear dimensions, where x is 10 cm, 7 cm, 5 cm, 4 cm, 3 cm, 2 cm, 1 cm, 9 mm, 8 mm, 7 mm, 6 mm, 5 mm, 4 mm, 3 mm) has an increasing softness/decreasing harness extending from the proximal to distal ends, the very distal end region 107 (e.g., measured as distal most z linear dimensions, where z is 1 cm, 9 mm, 8 mm, 7 mm, 6 mm, 5 mm, 4 mm, 3 mm, 2 mm, 1 mm, 0.8 mm, 0.5 mm, 0.3 mm, 0.2 mm, etc., and z is always at least three times less than x) has a hardness that is greater than the hardness of the region immediately proximal to it, and may be as hard or harder than the proximal-most region of the distal tip region.

In FIG. 1A, the elongate inversion support catheter is an elongate hollow catheter having a column strength that is sufficient to prevent buckling when the catheter is pulled over the distal annulus (distal end opening). Thus, the elongate inversion support may be configured so that it does not collapse (e.g., buckle) when 500 g or less of compressive force is applied (e.g., at least about 700 g, 600 g, 500 g, 400 g, 300 g, etc. of compressive force) for neurovascular applications. For peripheral vascular applications the elongate inversion support may be selected or configured to withstand at least 1500 g of compressive force (e.g., at least about 2000 g, 1900 g, 1800 g, 1700 g, 1600 g, 1500 g, 1400 g, etc. of compressive force). In general, any of the apparatuses disclosed and described herein may include an elongate inversion support catheter that is not a full-length catheter, but may include a portion of a catheter, typically at the distal end, connected to a rod, wire, hypotube, or the like. In FIG. 1A the catheter 100 of the elongate inversion support catheter may be any appropriate type of catheter or portion of a catheter, including microcatheters appropriate for neurovascular use.

In some variations the distal end 105 of the elongate inversion support is adapted so that the tractor may slide or roll and invert over the distal end of the catheter without being caught (binding, jamming) or without substantial friction. For example, in some variations the distal tip (end) may be curved or radiused 109 as shown in FIG. 1B, particularly on the outer surface (e.g., the transition from outer diameter to inner diameter).

FIG. 1C shows an example of a flexible tractor tube 144 coupled to an elongate puller 146, forming a pullable tractor assembly 140. In this example, the tractor tube is shown integrated with the puller and extending back over the puller, forming the assembly. The opposite end of the flexible tractor tube 147 is open and free (e.g., not connected to the puller or catheter). As will be described in greater detail below, this open, free, end may be adapted to be expanded and held open, e.g., by shape setting back on itself and/or by including an annular bias, to enhance deployment and positioning of the catheter between the flexible tractor tube and the puller. In FIG. 1C, the tractor tube is formed of material (e.g., wove, knitted, braided, etc.) that is flexible and elongate. The tractor is shown extended from the puller in a first configuration. It may be particularly beneficial if the relaxed outer diameter of the flexible tractor in this first configuration has a greater outer diameter than the outer diameter of the catheter of the elongate inversion support into which the tractor will be positioned prior to inverting. The flexible and tubular tractor 144 may be sufficiently soft and flexible (e.g., having a low collapse strength) so as to easily roll and fold over the distal aperture of the elongate inversion support. The puller 146 may typically be a less-expandable (or non-expandable) structure (tube, puller, etc.). For example, the tractor 144 may be configured, e.g., by shape-setting (heat setting, etc.), to expand in the relaxed first configuration to a radial diameter that is between 1.1 and 10 times (e.g., between 1.1× and 5×, between 1.1× and 4×, etc.) the diameter of the inner diameter of the catheter of the elongate inversion support when unconstrained. In FIG. 1D, the tractor tube has a larger expanded diameter than the variation shown in FIG. 1C n a relaxed configuration. In any of these variations, the expandable tractor may be biased to expand open. The tractor may be formed of a mesh, braided, woven, knitted, or sheet of material and is generally adapted to grasp the object to be removed (e.g., blood clot).

In FIGS. 1C and 1D the tractor and puller have two portions, a tractor tube 144 and a less expandable (or non-expandable) proximal portion comprising the elongate puller 146. The puller may be a separate region, such as a wire, catheter or hypotube, which is connected to an end region of the tractor (e.g., a flexible mesh, woven, braided, etc.), e.g., the distal end or near the distal end. The inverting region of the tractor, where it rolls and inverts over the distal end opening of the catheter may be referred to as the distal-facing region of the tractor, which may actively grab clot when rolling.

Figures 1E, 1F, 1G, 1H:
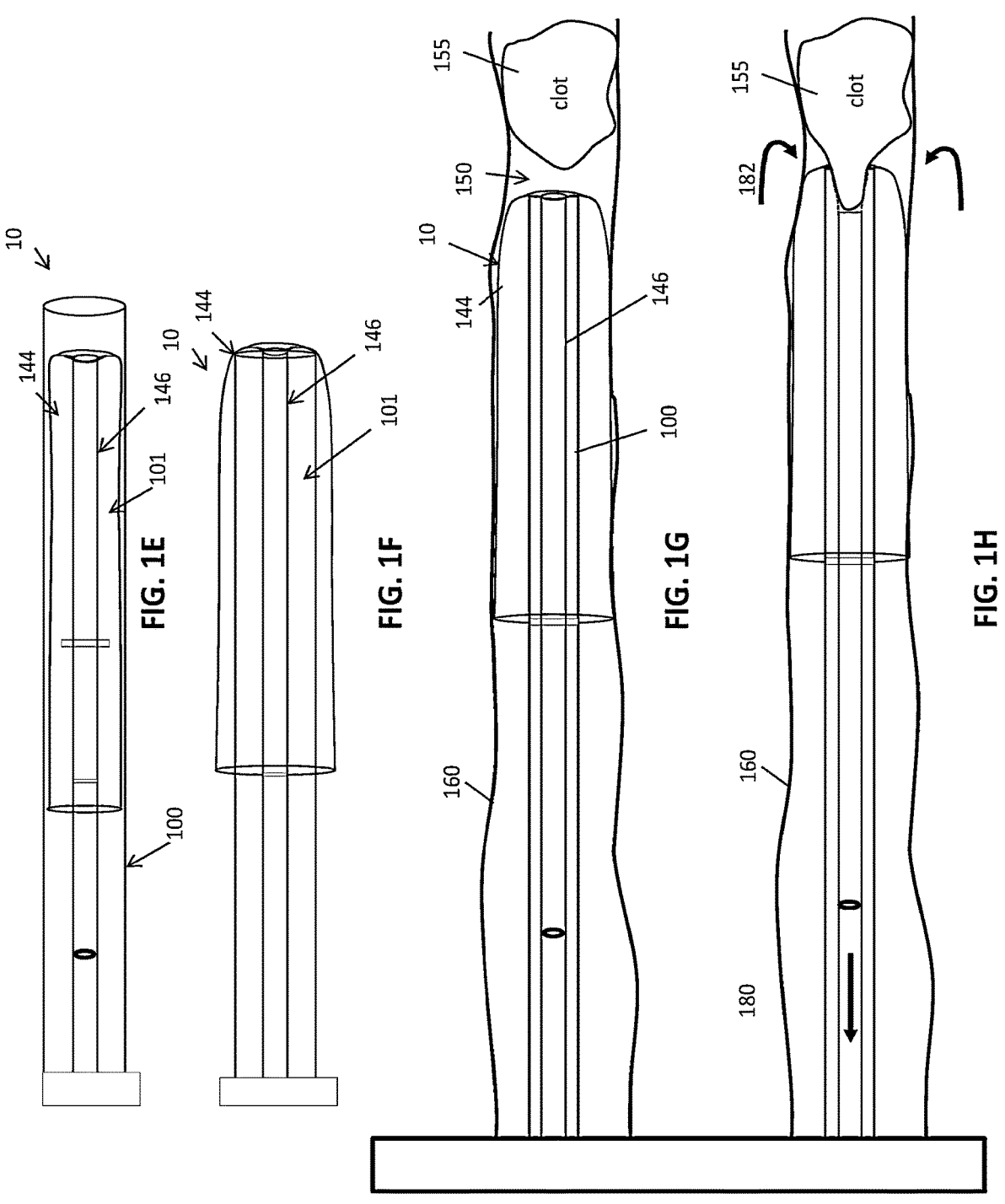

In FIG. 1E, the tractor assembly (flexible tractor tube 144 and puller 146 of FIG. 1D) are shown within an elongate inversion support catheter 100. The tractor is collapsed down 101, e.g., onto the puller, and may be held collapsed within the elongate inversion support catheter. Thus, FIG. 1E shows the pre-deployment (e.g., delivery) configuration. The tractor assembly may be axially movable (slidable) within the catheter so that it can be positioned within the catheter and within the vessel.

FIG. 1F shows a fully deployed apparatus. In FIG. 1F, the tractor tube is in an unconstrained or deployed configuration, and the elongate inversion support catheter is positioned between the tractor tube and the puller so that the tractor tube can be pulled proximally by pulling on the puller and rolling the tractor tube into the elongate inversion support catheter so that it inverts. In FIG. 1F, the tractor in this deployed configuration (e.g., the portion that is inverted over the distal end of the catheter) has an outer diameter that is greater than the outer diameter of the catheter of the elongate inversion support. Thus, the tractor 144 may be biased so that it has a relaxed expanded configuration with a diameter that is greater than the outer diameter (OD) of the elongate inversion support catheter; in addition, as will be described in relation to FIGS. 1G and 1H, below, the tractor tube may also be configured (e.g., by heat setting, etc.) so that when the tractor tube is inverted and pulled into the elongate inversion support catheter, the outer diameter of the inverted tractor tube has an outer diameter that is greater than 0.5× (e.g., greater than 0.6×, greater than 0.7×, greater than 0.75×, greater than 0.8×, greater than 0.9×, greater than 1×, etc.) the inner diameter (ID) of the elongate inversion support catheter. This combination of an un-inverted diameter of the tractor tube of greater than the diameter of the OD of the elongate inversion support catheter and an inverted diameter of the tractor tube of greater than 0.7× the ID of the elongate inversion support catheter is surprisingly helpful for preventing jamming of the apparatus, both when deploying the apparatus and when rolling the tractor over the distal end opening of the elongate inversion support catheter to grab a clot. The tractor may be expandable and may be coupled to the puller as shown. In some variations the flexible tractor and the puller may comprise the same material but the tractor may be more flexible and/or expandable, or may be connected to elongate puller (e.g., a push/pull wire or catheter).

Figure 1I:
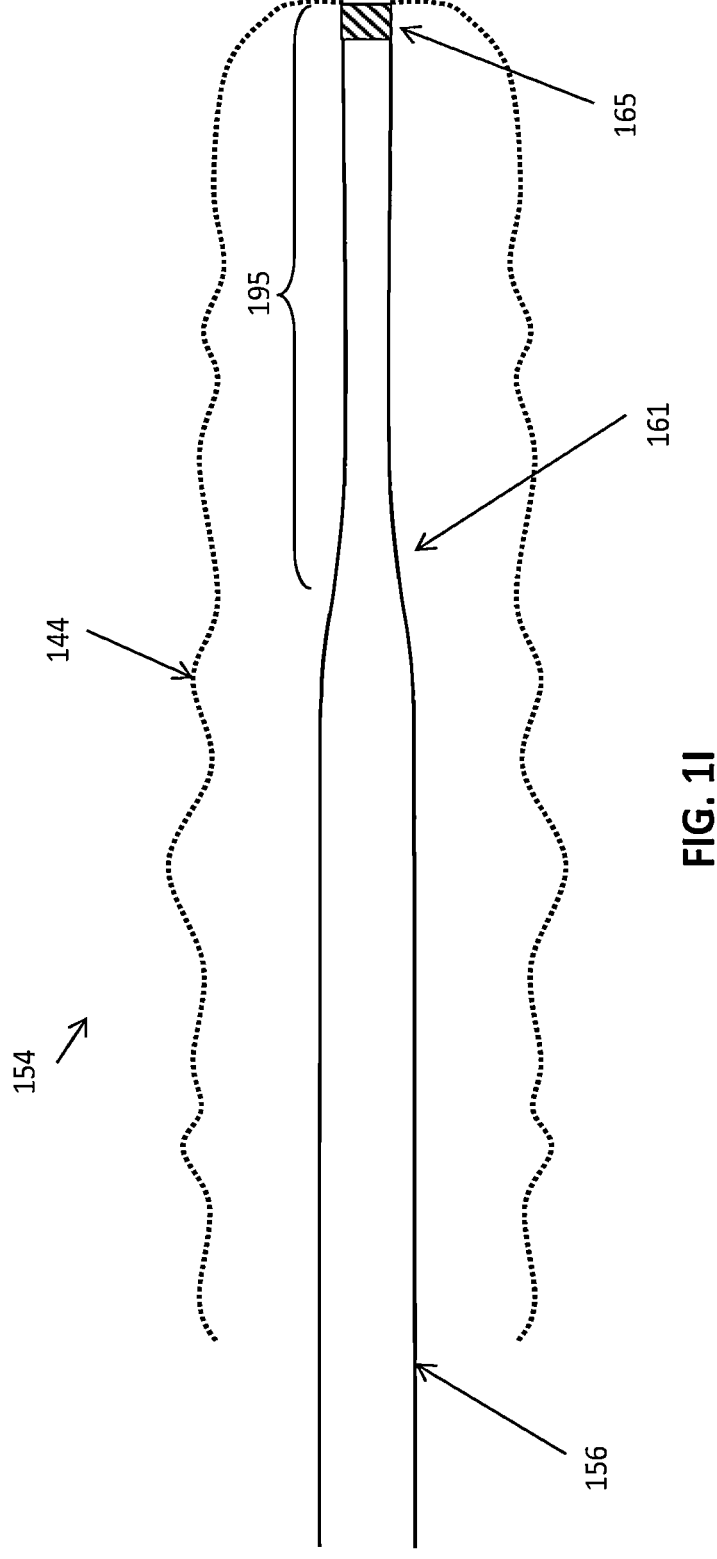
FIG. 1I illustrates an alternative variation of a tractor and puller.

FIGS. 1G and 1H illustrate the removal of a clot using an apparatus such as the apparatus components of FIGS. 1A and 1E. The apparatus 10 is shown in a deployed state. In this example the thrombectomy apparatus 10 is configured as a thrombectomy apparatus including an elongate inversion support catheter 100 and a flexible tractor tube 144 that extends over the distal end region of the catheter and doubles-over itself at the distal end of the catheter to invert so that the external tractor end region is continuous with an inner, less-expandable (in this example, less-expandable includes non-expandable) second distal end region 146 (puller) that extends proximally within the catheter and forms an inner lumen that may pass a guidewire. The pusher/puller member that may be a rod or other member that is continuous with the distal end region of the tractor. In FIG. 1G the apparatus is shown positioned and deployed within the vessel 160 near a clot 155. The clot may be drawn into the catheter by pulling the tractor 140 proximally into the catheter 101, as indicated by the arrow 180 showing pulling of the inner portion of the flexible tractor (e.g., using a handle, not shown) resulting in rolling the tractor over the end opening of the catheter and into the catheter distal end and inverting the expandable distal end region so that it is pulled into the catheter, shown by arrows 182. The end of the tractor outside of the catheter may be "loose" relative to the outer wall of the catheter. FIG. 1I illustrates another example of a tractor assembly 154 including a tractor tube 144 that is coupled to a puller 156. The puller in this example is tapered (having tapering region 161) and may therefore have a different flexibility of the distal end region than the proximal end region. For example, the proximal end region may be less flexible than the narrower-diameter distal end region 195 to which the tractor is coupled. The assembly includes a radiopaque marker 165. The tractor may be attached to the puller by any appropriate means. For example, the tractor may be crimped, glued, fused, or otherwise attached to the puller, typically permanently.

In general, the mechanical thrombectomy apparatuses disclosed and described herein may be highly flexible, both before actuating and during operation. For example, the flexible tractor may not increase the stiffness/flexibility of the catheter of the elongate inversion support, and particularly the distal end region of the catheter too much, to avoid impacting maneuverability, particularly within tortious vessels of the neuro-vasculature. Disclosed and described herein are flexible tractor tube portions that increase the stiffness of the last y cm (e.g., distal most 20 cm, 18 cm, 15 cm, 12 cm, 10 cm, 9 cm, 8 cm, 7 cm, 6 cm, 5 cm, 4 cm, 3 cm, 2 cm, 1 cm, etc.) of the catheter less than a predetermined percentage (e.g., less than 10%, 12%, 15%, 18%, 20%, 25%, 30%, etc.). For example, disclosed and described herein are flexible tractor tube portions that pass through the catheter and double back over the distal end of the catheter but increase the stiffness of a distal 5 cm of the catheter by less than 15% of the stiffness of the distal 5 cm of the catheter without the flexible tube extending therethrough and doubling back over the distal end of the catheter.

The tractors may be woven, braided and/or knitted materials. For woven and braided materials, which may include a plurality of fibers that are woven or braided to form the inverting tube, these structures may be tuned to prevent jamming and/or to reduce the force necessary to pull the tractor and invert over the catheter tip. For example, the mechanical atherectomy apparatus may include a braid-type tractor that can roll freely around the tip of catheter even in a tortuous anatomy and when grabbing clot by tuning one or more of the braid structure; minimizing the braid angle; including a hydrophilic coating on the distal aspect of the catheter outer diameter (OD) or the inner diameter (ID) of the braid (e.g., tractor); including a radiused wall on the catheter; and/or increasing the stiffness of the distal tip region relative to adjacent proximal regions. Alternatively, it may be advantages to have a hydrophilic coating on 1, 3, 5, 10, or 15 cm of the distal ID or the entire catheter ID. This may even enhance aspiration of the clot without a tractor element.

As mentioned, the tractor (e.g., braided, woven, knitted, etc.) may be configured to collapse down into the inner diameter (ID) of the catheter as little as possible. For example, the tractor may collapse to an ID that is greater than, equal to, or within 90%, 85% 75%, 70%, 65%, 60%, or 50% of the catheter inner diameter (ID)/Catheter Tip OD, since, when the tractor is being pulled around catheter tip it may create axial tension on the tractor (e.g., braid, knit, etc.) that can inadvertently cause the tractor to jam on the catheter tip. When tractor is pulled around catheter tip, the tractor is being pulled in the axial orientation creating axial tension on tractor structure as the tractor is being pulled through the catheter ID. By having the tractor elements jam at an ID greater than or equal to 90%, 85%, 75%, 70%, 65%, 60%, or 50% of the catheter ID (or in some variations, GD), when being axially tensioned, the tractor is less likely to grab/synch down onto the catheter tip, helping the braid roll around the catheter tip with less axial force applied by the user. If less axial force is required by the user to pull the tractor structure around the tip then the catheter tip is less likely to buckle or deflect when retracting the tractor. It may be advantageous to minimize the chance the catheter tip will buckle. The tractor can be tuned to "jam" at a specific ID by controlling any of the following variables and in any combination: selecting a specific number of braid ends, selecting the size/diameter of the braid ends; selecting the braid material (e.g., multifilament or monofilament); heat setting the bias on the braid (e.g., braid diameter); and selecting a braid pattern, e.g., 1×2, 1×1 or any other pattern.

The braid angle may be minimized to prevent locking up of the rolling of the tractor over the catheter end opening. Typically, the lower the braid angle (e.g., 45 degrees or less, 40 degrees or less, 35 degrees or less, 30 degrees or less, 25 degrees or less, 20 degrees or less, etc.) the less likely it is to have the braid cross over points catch on the catheter tip.

In any of the variations disclosed and described herein, the catheter and/or a surface of the tractor may be coated to enhance rolling over the distal end region of the catheter. It may be helpful to have a hydrophilic coating on the distal aspect of the catheter OD or the ID of the tractor so the tractor can more easily side over the catheters distal end and around the tip of the catheter when pulled through the inside of the catheter.

The radius wall of the catheter tip may be chosen/set to within a range that allows sliding. For example, it may be helpful for the tip of the catheter to have the largest radius possible but at least 0.0025" radius wall on the catheter, ideally approximately 0.005" radius wall.

The stiffness of the distal of the catheter may be sufficiently stiff to prevent collapse as the tractor is pulled; it may also be lubricious (e.g., by a coating or material property). The distal most section of the catheter tip (e.g., the last 5 mm) may be fabricated of a material which is stiff enough and lubricious enough so the distal tip of the catheter does not collapse or buckle inward ward when the braid structure is rolling around the catheter tip. Thus, the distal tip may have a stiffness that is greater than the more proximal region at the distal end of the catheter.

It may be helpful or desirable to have pores in the tractor. A lack of gaps or small pore size may limit the ability of the braid to grab clot. Alternatively, or additionally, it may be desirable to form a braid structure with texture. One example is to braid two or more different diameter braid ends into the same structure: the difference in braid end diameters will help form a texture to the braid structures outer surface, aiding the grabbing of the clot when rolling the braid-dozer around the catheter tip.

As an alternative (or in addition) the tractor may be configured to lock so it does not compress in diameter during axial load by adding a coating, laminate or adhesive to the braid at a desired diameter. Adding a thin coating, laminate or adhesive can inhibit the braid elements from sliding with respect to each other, thereby locking the braid to a specific diameter. The coating can be applied while leaving the majority of the pores and pore area substantially open. Examples of thin coatings include urethanes and silicones with and without hydrophilic coatings and hydrophilic coatings with no tie layer.

Reducing the sliding friction of tractor to outer catheter wall, improving tractor to tip rolling, and/or enhancing tractor to inner catheter sliding may also be achieved by including a sliding skin or sleeve. For example, a thin (e.g., ultrathin) sleeve may be used. The sleeve would be made from low friction polymer (e.g., PET, PE, PP, PTFE, ePTFE, pebax, urethanes) by braiding, knitting, weaving, extrusion, melt blown, melt spinning, etc. The sleeve could be made from laser slotted tubing, chemical etching, micro machining. The sleeve could be also coated with a lubricious coating such as a hydrophilic coating. Lubricious coatings can be located on the outside and/or inside surfaces. The sleeve may be placed between the dozer element and the catheter wall and attached to the puller element. The sleeve may be less than 0.002" thick, ideally, less than 0.001" wall thickness. The sleeve may decouple the tractor clot grabbing system from the catheter wall, tip rolling and inner catheter dragging friction. The sleeve could be totally free from the tractor, connected to the tractor in discrete locations or connected fully to the tractor. This may allow the tractor to be designed to grab clot (larger wires: 0.001" to 0.002" for neuro, and 0.002" to 0,007" for other applications) and the skin to minimized in thickness and structure to reduce friction and skin bending stiffness.

In any of the apparatuses disclosed and described herein, the catheter (e.g., the inversion support catheter) may be covered with a jacket along all or a part of its length. This jacket may be highly elastic, and may include a single layer or multiple layers. The jacket may be have a single durometer (e.g. stiffness) or multiple durometers along its length; for example the jacket durometer may be less stiff near the distal end of the catheter. The jacket may be formed of any appropriate material, including urethane (e.g., Teflon 20A to 93A, e.g., 80-85A). PEBAX (e.g., 25A to 72D), silicone, nylon, etc. In an of these variations the jacket may be continuous or formed along with a sleeve such as described above, that transitions from the inside of the catheter and around this distal end opening and along the outer surface of the catheter. The jacket may be integrally formed and/or fused to the sleeve. The sleeve may also be referred to as a liner. As mentioned, the sleeve may be a lubricious material, such as PTFE, FEP, HDPE, Polypropylene, and/or other polymers, particularly those with modifier such as siloxane modifiers. The jacket may be bonded to the sleep/liner (e.g., through the cut frame of the catheter, such as a slotted catheter).

In some variations, the tractor region may be formed of with a mixed or hybrid structure, combining one or more of interwoven or knitted braid polymer filaments with metallic filaments. The mixed structure (hybrid structure) may leverage both metallic elements interwoven with low friction polymer elements. The metallic filaments may create stiffness elements that may grip/grab a clot. The polymer filaments may aid in grabbing clot but may provide surface friction reduction to the outer catheter wall, the catheter tip and the inner catheter wall once around the tip.

Any of the apparatuses disclosed and described herein may include a tractor having a hydrophilic/lubricous coating on the inside surface, e.g., for braided/knitted tractors, on the inside surface (contacting the outer and inner diameter of the catheter) of the braid/knit, which is in contact with the outside of the catheter. Examples of lubricous coatings include hydrophilic coatings (e.g., hydrogels) and hydrophobic coatings (e.g., fluorine coating such as PTFE & FEP, parylene, silicone, siloxane (silicone additive) added to various polymers including pebax to make any material more lubricious, Polyethylene, polypropylene, FEP)

As mentioned above, any of these apparatuses may include a distal tip that is less rigid (e.g., 'softer') than the more proximal regions of the distal tip. This may be achieved by having a structural supporting member reinforcing the distal tip, or by modifying the material forming the distal tip.

Any of the tractors disclosed and described herein may include a marker or makers (e.g., radiopaque markers, such as gold, Pt, etc.).

Any of the apparatuses disclosed and described herein may include a lubricious sleeve within the distal end of the elongate inversion support catheter to enhance rolling of the tractor tube, and particularly a knitted tractor tube into the distal end of the elongate inversion support catheter. For example, FIG. 1A illustrates a first example of a mechanical thrombectomy apparatus including a lubricious liner 211 that wraps over the distal end of the elongate inversion support catheter 201. In this example, the inverted knitted tractor tube 203 rolls over the distal end of the elongate inversion support catheter and is attached at one end to a puller 207 (shown as a pull wire in this example). Pulling proximally on the puller rolls the tractor tube into the elongate inversion support catheter's distal end opening and pulls the clot 219 into the elongate inversion support catheter. The apparatus may include or may be operated with a guide catheter 205, so that the inner elongate inversion support catheter may be extended distally out of the guide catheter. In sore variations, the guide catheter may be used to releasably secure the outer portion of the tractor tube 203 against the outer surface (outer diameter) of the elongate inversion support catheter 201 and may be retracted fully (as shown in FIG. 2A) or partially (as shown in FIG. 2B) when operating the apparatus to grab an d/or remove a clot 219.

Figure 2A:
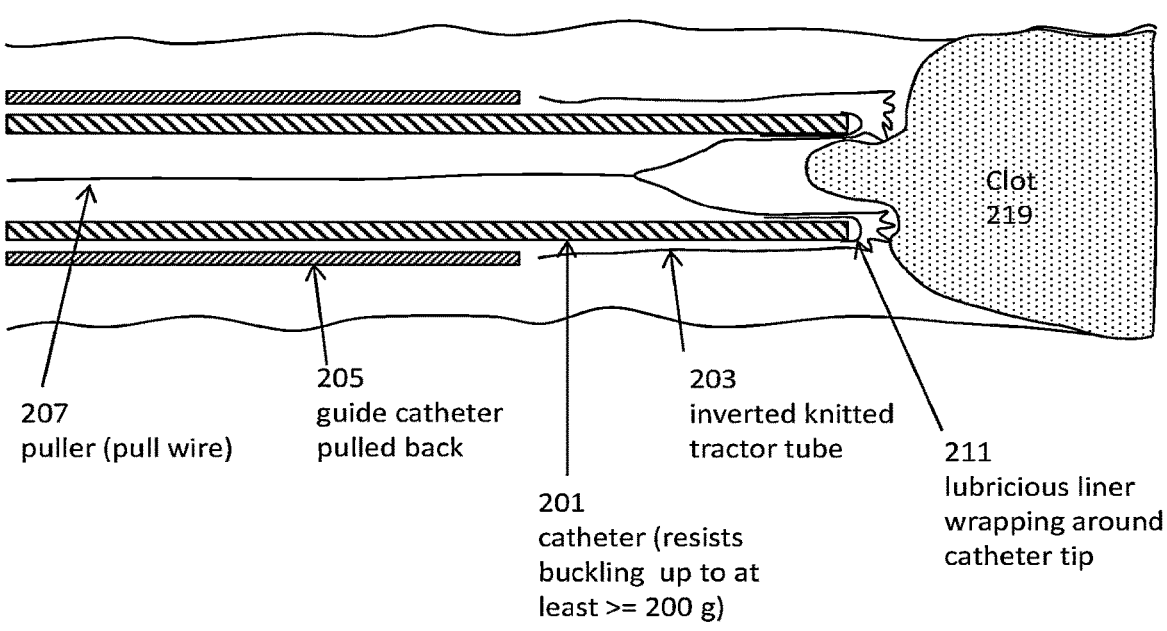
FIG. 2A illustrates a first mechanical thrombectomy apparatus and method of using it to remove a clot.

FIG. 3 schematically illustrates a method of removing a clot using an apparatus including a lubricious sleeve inverting over the distal end of the elongate inversion support catheter, similar to that shown in FIG. 2A. In FIG. 3, the method may include generally delivering a guide (or "intermediate") catheter to the face of a clot 301. This step may be optionally performed with the mechanical thrombectomy apparatus (e.g., the elongate inversion support catheter and tractor tube pre-loaded, e.g., near the distal end of the delivery catheter). Thereafter, the thrombectomy catheter may be delivered thru guide (intermediate) catheter 303 so that the elongate inversion support catheter is near the face of the clot. Once in position, the tractor may be deployed; for example, while applying some push force on the elongate inversion support catheter, the guide (intermediate) catheter may be retracted to un-sheath the tractor tube 305. This may result in the arrangement shown in FIG. 2A, for example. Optionally, aspiration may be applied through the elongate inversion support catheter (and/or the puller in variations of the puller having an inner lumen) before retracting the guide (intermediate) catheter. Aspiration may therefore be optionally through elongate inversion support catheter (and/or the intermediate catheter). Thereafter, the puller connected at one end to the tractor tube may be pulled proximally, preferably while putting forward an advancing force on the elongate inversion support catheter, to grab and remove the clot from the vessel 309.

Figure 2B:
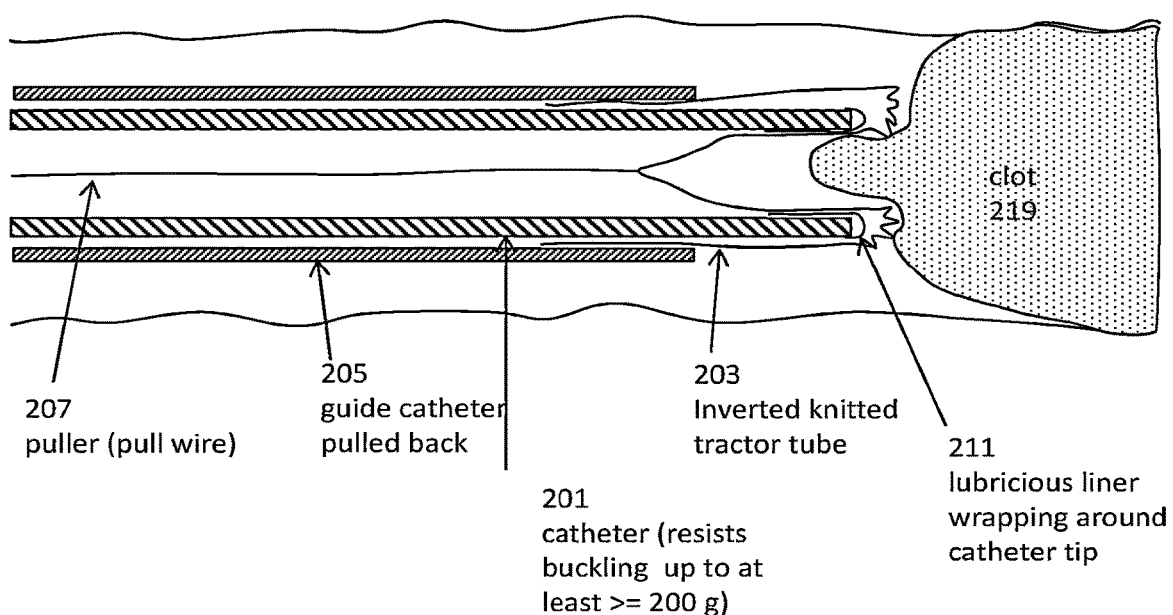
FIG. 2B is the mechanical thrombectomy apparatus of FIG. 2A, and an alternative method of using it to remove a clot. In this example, the outer catheter ("intermediate catheter") is only partially withdrawn so that the distal end of the tractor tube (shown as a knit tractor tube) is still held in place against the outer wall of the elongate inversion support catheter portion by the intermediate catheter.

Alternatively, as shown in FIG. 2B, the guide (intermediate) catheter 205 may be only partially withdrawn over the elongate inversion support catheter 201 so the distal end of the knitted tractor tube 203 is still contained inside the intermediate catheter. This configuration may provide additional support for the elongate inversion support catheter when engulfing the clot with the knit tractor tube, so it is less likely to buckle or snake when it is exposed to the related compressive loads.

This configuration may also, because of the additional outside support of the intermediate catheter, allow the user to more easily advance the elongate inversion support catheter forward in the vessel as the trailing edge of the clot is engulfed. The intermediate catheter can cover 10%, 20%, 30%, 40%, 50%, 60%, 70%, 80%, 90%, etc., of the tractor length on the outside of the catheter. Or the intermediate catheter can be positioned less than 1 cm, 2 cm, 3 cm, 4 cm, 5 cm, 10 cm, etc. back from the distal tip of the elongate inversion support catheter.

The lubricious liner wrapping around the elongate inversion support catheter tip may be any appropriate liner. The liner typically wraps from an outer surface of the elongate inversion support catheter over to an inner surface of the elongate inversion support catheter. This nay be in addition to or instead of a coating and/or shaped distal end region of the elongate inversion support catheter.

Figure 6A:
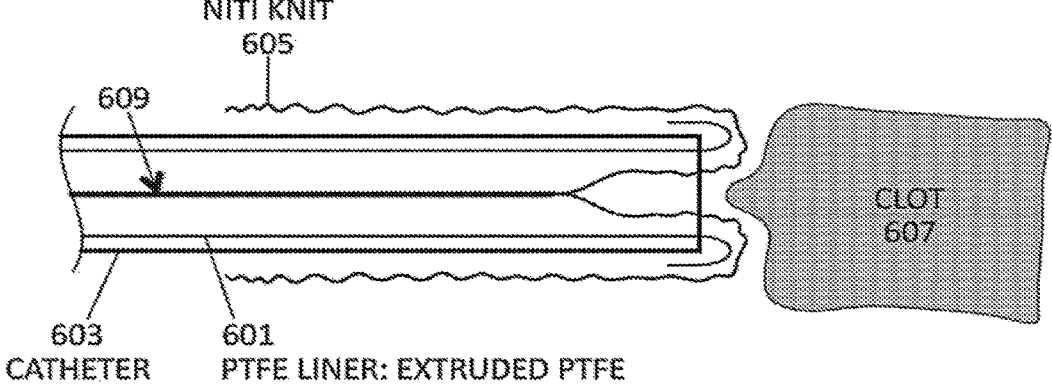
FIG. 6A illustrates an elongate inversion support catheter of a mechanical atherectomy apparatus including a low-friction liner (e.g., a PTFE liner) extended around the catheter tip to reduce pull friction.
Figure 6B:
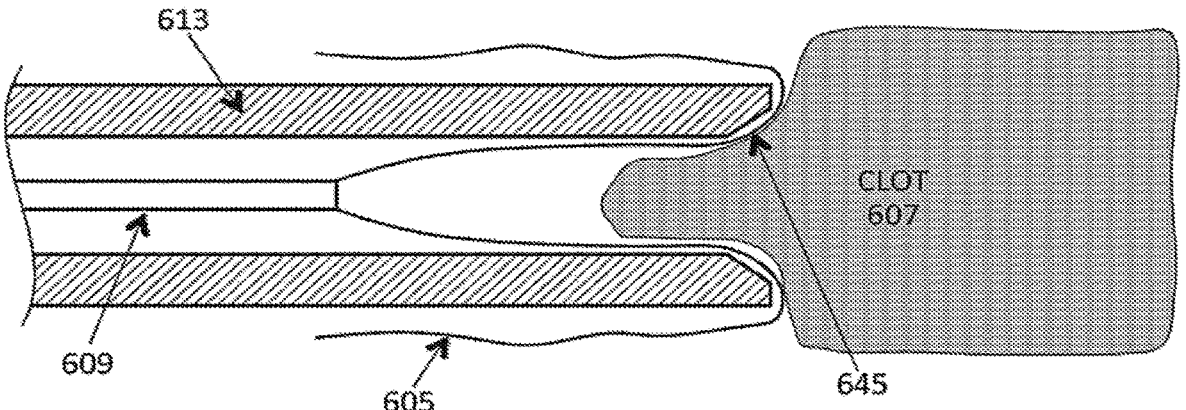
FIG. 6B illustrates a modified tip for an elongate inversion support catheter, having a chamfer on the inner radius of the catheter to reduce pulling forces.

FIGS. 6A and 6B illustrate another example of a lubricious liner. For example, in FIG. 6A the lubricious liner 601 is a PTFE liner wrapping around the open distal end of the elongate inversion support catheter 603. A tractor tube (a nickel titanium knitted tractor 605) is shown inverting into the end and over the PTFE liner 601. One end of the tractor tube is connected to a puller 609 and may be drawn proximally to pull in a clot 607.

Alternatively, or additionally, the elongate inversion support catheter may be shaped to reduce the pull force need to invert the tractor tube into the elongate inversion support catheter. For example, FIG. 6B shows an elongate inversion support catheter 613 distal end opening may be shaped (e.g., chamfered 645) to reduce the pull force/friction.

In general, larger (e.g., clots having a diameter greater than 2× the diameter of the elongate inversion support catheter) and/or hard clots may be more difficult to compress and pull into a mechanical thrombectomy apparatus. Surprisingly, the apparatuses and methods disclosed and described herein may be used to draw even larger and hard clots into the apparatus.

Figure 4A:
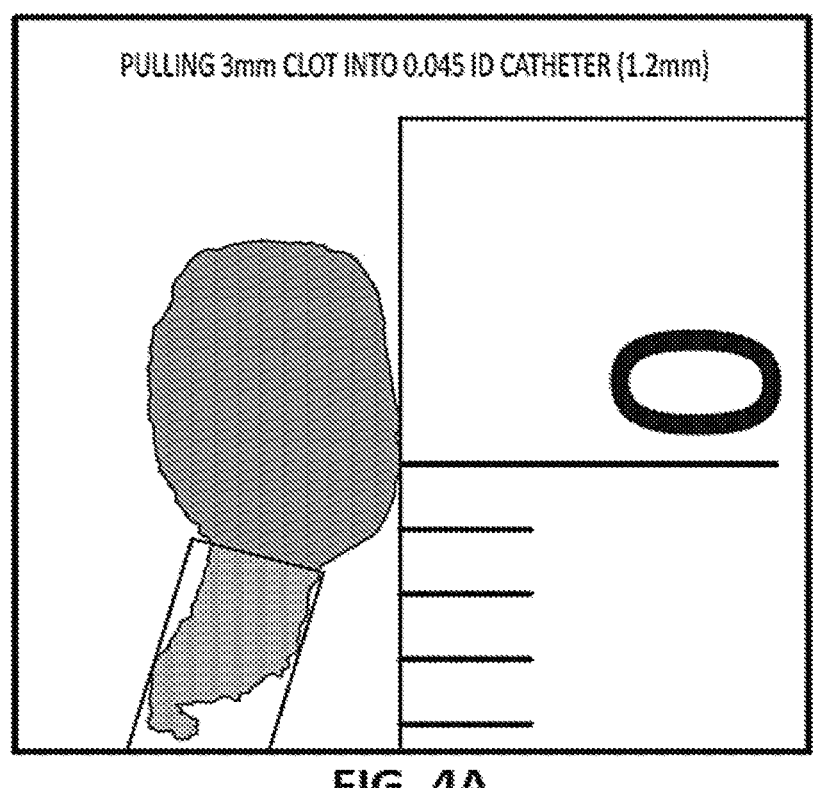
FIG. 4A is an example of a large (e.g., 3 mm) and hard clot into a smaller ID catheter (e.g. 0.045 ID catheter of 1.2 mm opening diameter).
Figure 4B:
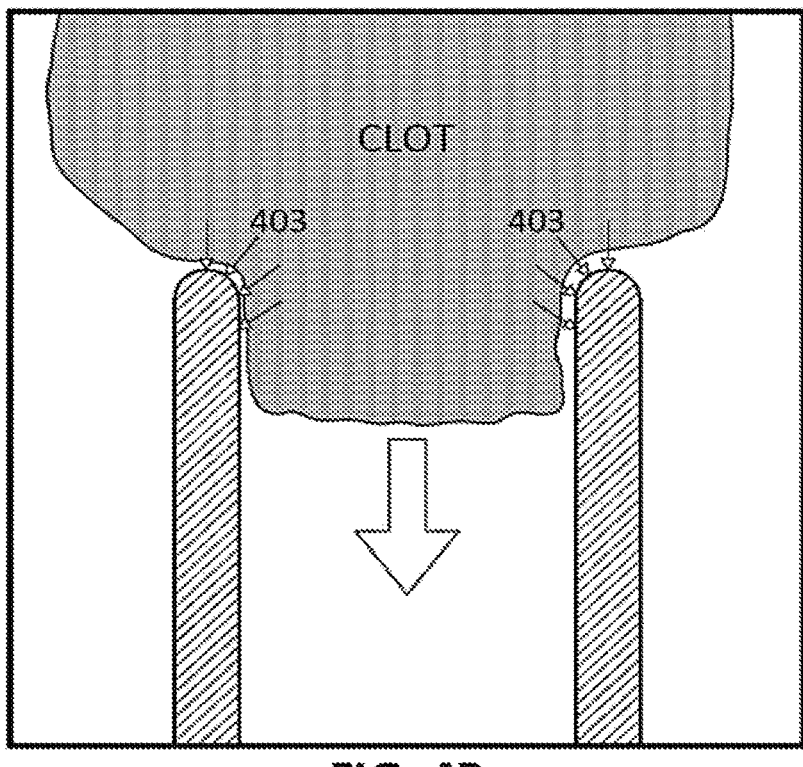
FIG. 4B illustrates the normal forces on the inner and distal ends of the elongate inversion support catheter wall. The use of a low-friction material, such as a Teflon sleeve, extending around the distal end opening of the elongate inversion support catheter portion may prevent jamming and aid in compacting the hard clot.

A hard clot typically may take a significant compressive load in order to compress the clot and engulf it in a smaller ID elongate inversion support catheter. As mentioned, hard clot may require a significant compressive load to compress the clot, generating a relatively high normal force to the distal & inner end of the catheter wall. The low friction surface (including sleeves) disclosed and described herein may help reduce the load to pull in clot to less than 300 g of force, when measured from the pull force required to pull the tractor grabbing the clot into the elongate inversion support catheter (e.g., less than or equal to 300 g, less than or equal to 250 g, less than or equal to 200 g, etc.). FIGS. 4A and 4B illustrate the compression of a large-diameter (compared to the diameter of the elongate inversion support catheter) clot into an apparatus as disclosed and described herein. FIG. 4A shows a 3 mm clot being pulled into a 0.045 ID catheter (having a diameter of 1.22 mm). In FIG. 4B, the arrows 403 show normal forces generated at the inner opening edge of the elongate inversion support catheter.

Figure 5:
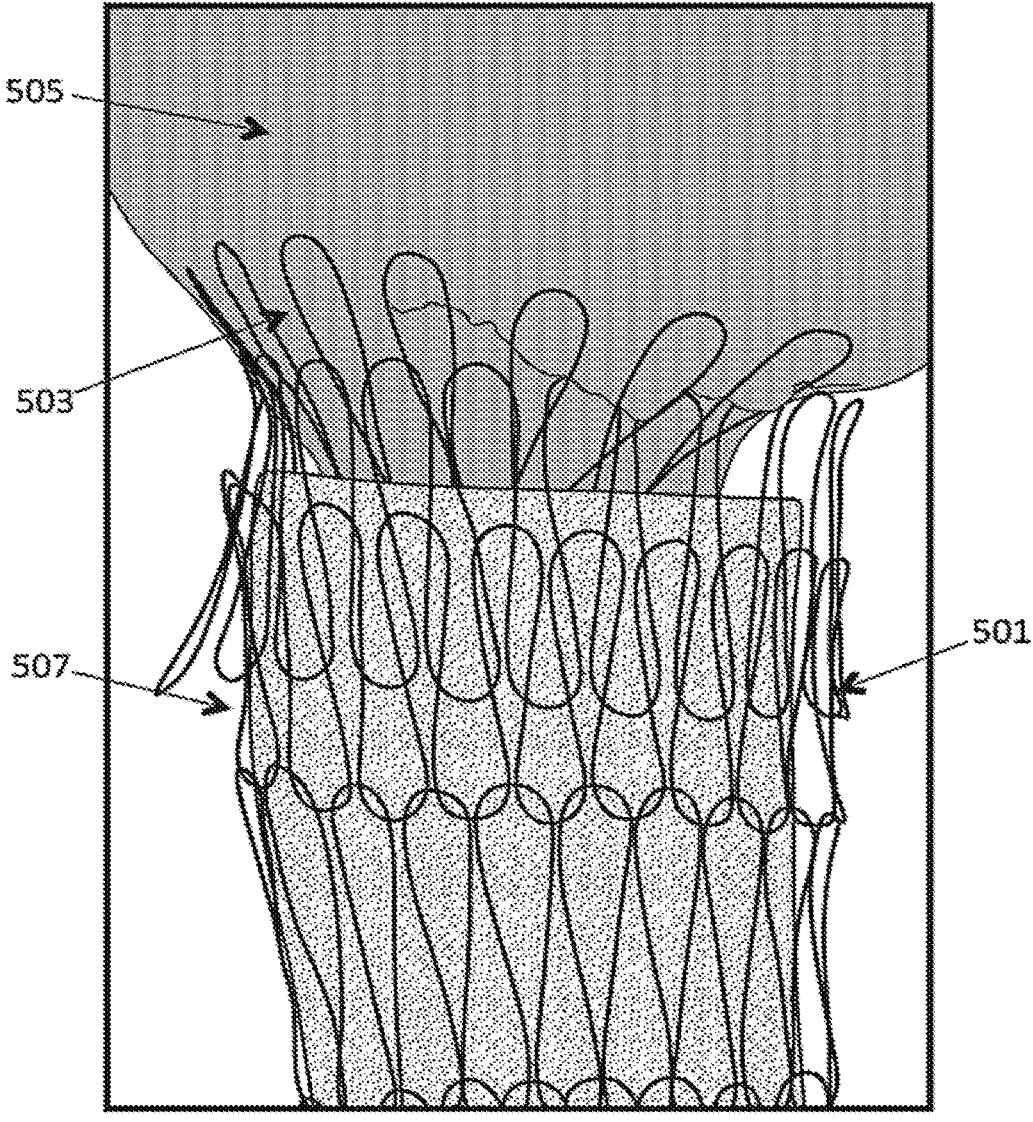
FIG. 5 illustrates a knit tractor tube that may also aid in pulling a large-diameter clot into an elongate inversion support catheter.

As mentioned above, any of the apparatuses disclosed and described herein may preferably include knitted tractor tubes. The orientation (e.g., "inside out") as well as the shape-set of the knit may be selected to prevent jamming, reduce the pull force necessary to invert the tractor into the elongate inversion support catheter, and may help knead, compress, and/or drive the clot into the opening of the elongate inversion support catheter. For example, FIG. 5 illustrates an example of a knitted tractor 501 being pulled to invert into an elongate inversion support catheter 507. The knit is formed by knitting single strand of wire (though multiple strands of one or more filaments, weaves, braids, etc. may be used) to form a plurality of rows of loops 503 that are interconnected. The loops may be pulled and inverted into the distal end opening of the elongate inversion support catheter so that, when in the inverted knit configuration, they flare outward and push the clot 505 into the elongate inversion support catheter. In FIG. 5 the clot is a large-diameter clot (>2× the diameter of the elongate inversion support catheter) and the knit tractor is shown flaring out to whip in front of the elongate inversion support catheter tip to knead the clot into catheter.

Figures 7E, 7F:
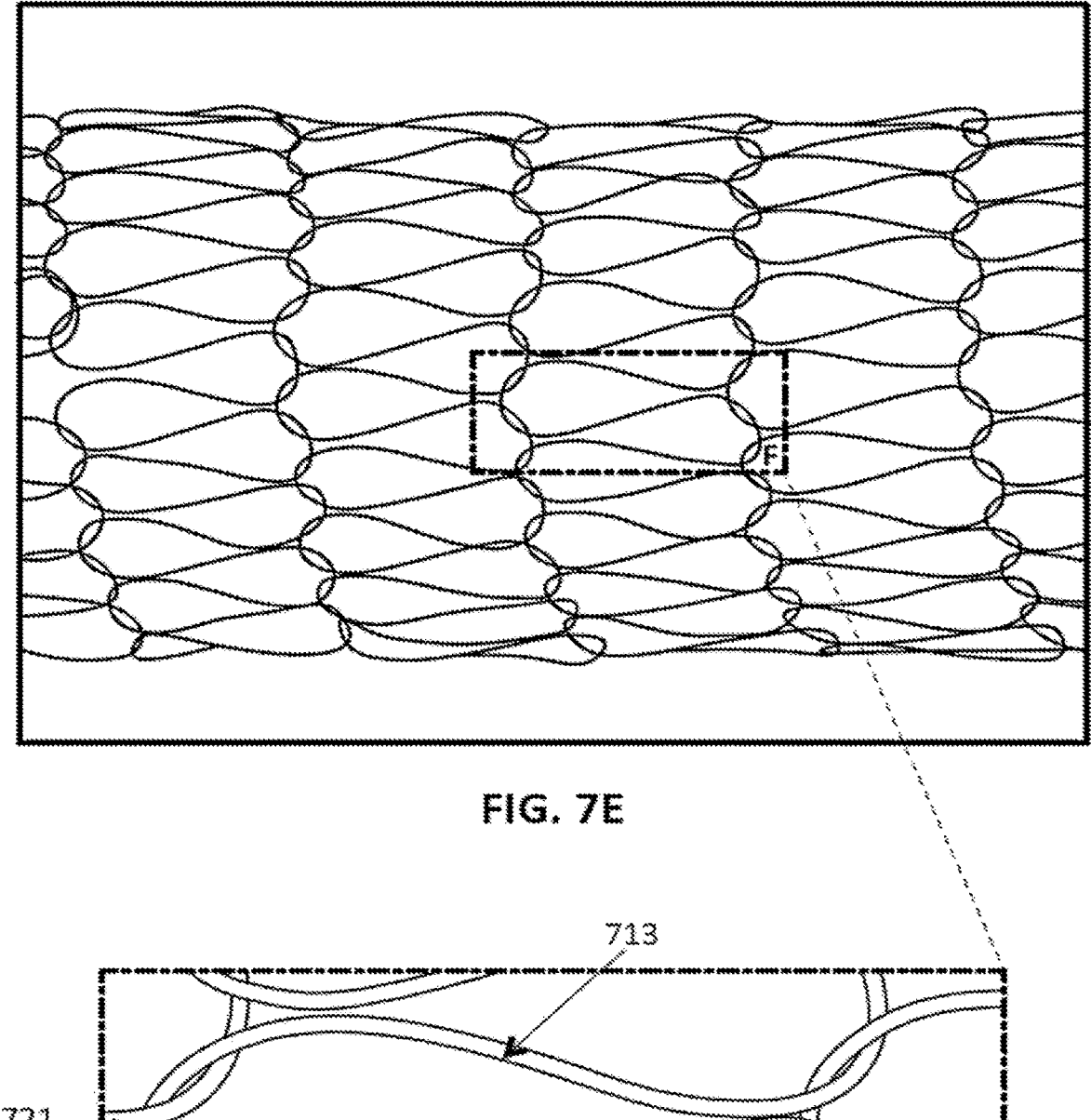
FIGS. 7E and 7F illustrates a non-inverted knitted tube that is less desirable, as it may jam or prevent smooth rolling, despite having links that are the same dimension (and formed of the same materials) as the inverted knit shown in FIGS. 7C and 7D.

FIGS. 7A-7F illustrate an example of knitted tractor tubes. FIG. 7A (and the enlarged view 7B) illustrate a first variation of a knitted tractor tube having a knit pattern that is less optimal, as the diameter of the knitted tractor tube is sufficiently large so that there are triple crossover points between the wire (e.g., strand, fiber, filament, etc.) forming the knit. Such "triple overlap" regions 705 may result in a thickness or OD of the tractor tube that is undesirably large. Thus, it may be better to size and/or shape set the knitted tractor tube to prevent or minimize these triple overlap regions in the links forming the knit (e.g., having less than 10% triple overlaps, <9%, <8%, <7%, <6%, <5%, <4%, etc.). FIG. 7C (and the enlarged region shown in FIG. 7D) illustrate a more optimized variation of a knitted tractor tube showing only double overlaps 707.

As mentioned above, it is also desirable to use a knitted tractor tube pattern in which the orientation of the knit is inverted (as compared to most commercially available knitted tubes), so that the links, when the tractor tube is inverted over the distal end opening of an elongate inversion support catheter and pulled into the elongate inversion support catheter, the links flair outward. Thus, the orientation of the knit may be configured so that the apex (tip) of the loops in each row are on the outside face of the elongate inversion support catheter over which the tractor tube is inverting, compared to the adjacent pair of links that each link loop is connected to. This inverted knit configuration is shown in FIGS. 7C and 7D. For example, in FIG. 70 the link 703 is formed of a filament (e.g., nitinol, polymeric material, etc.) that is knitted into a pattern of adjacent links that are interconnected (e.g, as the double crossover points 707, 707'). The knitted tractor tube is shown over an elongate inversion support catheter 709, so that the outward-facing surface of the knitted tractor tube includes all of the apexes 711 of each link. These links are therefore arranged to pass under then over a first adjacent link, then over and under a second adjacent link, as shown in FIG. 7D, leaving the apex region on the outward-facing side of this "inverted" knit configuration. In contrast, FIG. 7E (and enlarged view 7F) show a non-inverted knit configuration, in which each link 713 includes an apex 721 that is instead underneath (on the side facing the elongate inversion support catheter, not shown). Each loop is this example is formed of a filament that is woven in an over-under and then under-over pattern relative to adjacent links of the knit. The non-inverted knitted tube shown in FIGS. 7E and 7F is constrained when inverting over an elongate inversion support catheter, so that it cannot swing outward relative to the distal end of the elongate inversion support catheter, by the adjacent links. As a result, the pulling force of the tractor tube is surprisingly higher, and the clot-grabbing of the tractor may also be greatly reduced.

Figure 8A:
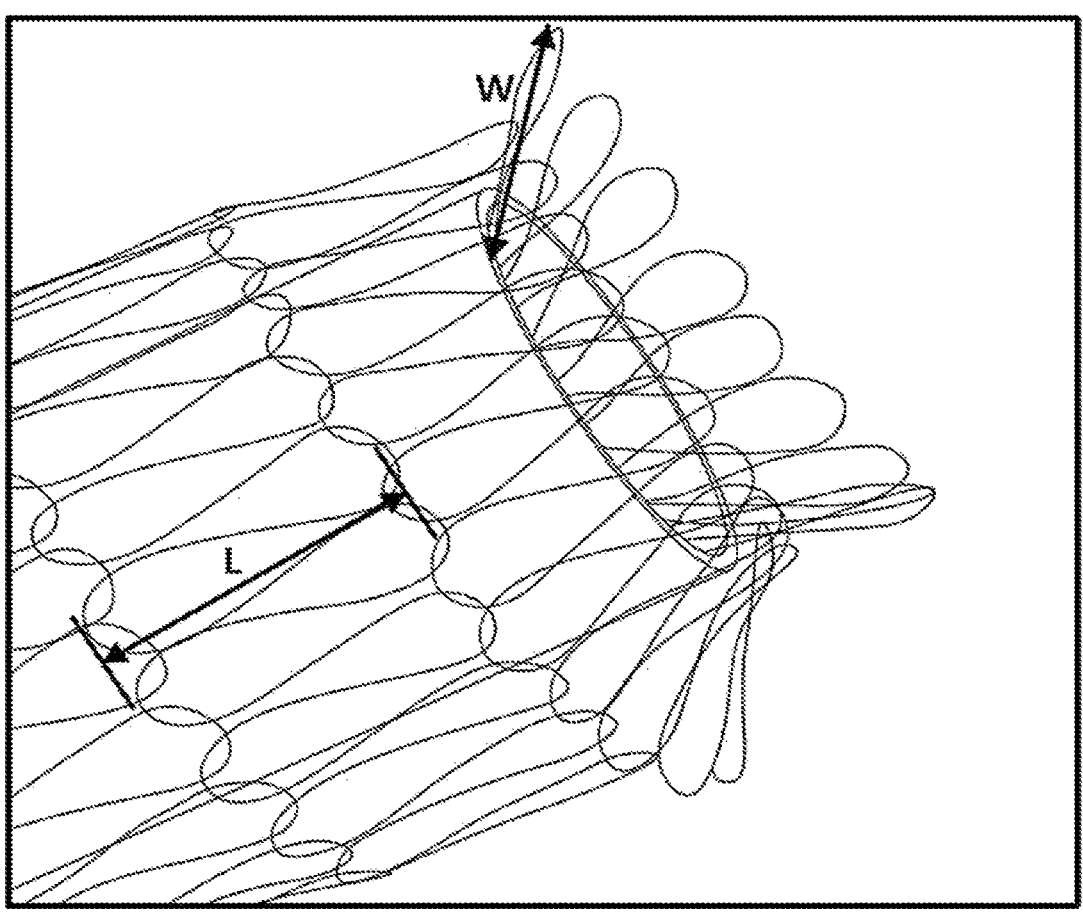
FIG. 8A is a side view of a distal end of a elongate inversion support catheter with a knitted tractor tube rolling into the distal end opening, illustrating tuning of the length, L of the woven links to achieve a desired grab width, W, e.g., between 30-90% of L, for grabbing a clot with a woven tractor as described herein.
Figure 8B:
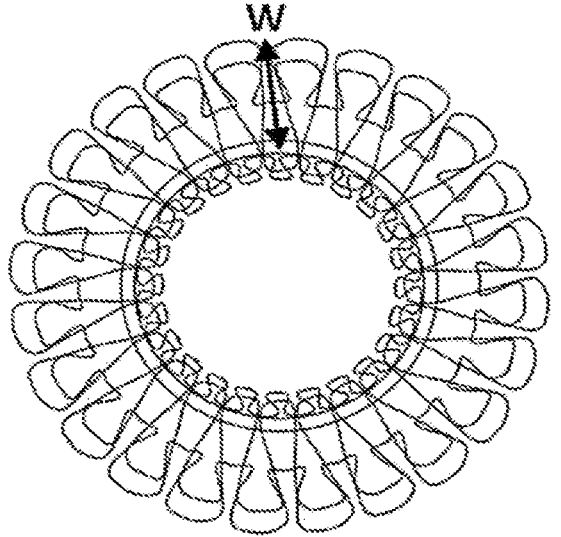
FIG. 8B is an end-on view of the apparatus of FIG. 8A.

FIG. 8A shows an example of an inverted knit tractor tube rolling over the distal end opening of an elongate inversion support catheter. In any of these variations, the knitted pattern may be optimized so that the stich length (L) may be tuned to get a desired grab width (W) increase that is greater than elongate inversion support catheter outer diameter (OD). This larger grab width may aid in grabbing a clot with the apparatus. In FIG. 8A, the length of each knitted link (L) is shown, as is the width (W) that the link ends outwards when inverting into the itself and the elongate inversion support catheter. Typically, it has been found to be desirable to have a width (W) of between about 30-90% of length (L). The exact dimension of the width (W) may depend on the tension in the knit used to pull in the clot (e.g. the great the tension, the smaller the W dimension), and the flexibility of the filaments used in the knit structure (e.g., the softer the filament used to form the knit, the smaller the W). The knit can be tuned through both the design and the processing so when it is tensioned at loads between 100-500 grams (g), the structure may have a limited elongation (e.g., <15%, <12%, <10%, etc. 0). When the knit structure is in this non-compliant/semi-compliant form the OD & ID of the knitted tractor tube may also be stable (e.g., having a <20%, less than 15%, less than 12%, less than 10%, etc. diameter change) under loads between 100-500 g. In this non-complaint/semi compliant form, the knit OD may be greater than the thrombectomy catheter, but less than the vessel OD. In other variations, the knit OD may be greater than the catheter OD, and the knit is rolled around and less than 5%, %10%, 20%, 30%, 40%, 50%, 60%, 70%, 80% of the same catheter OD.

Figure 9A:
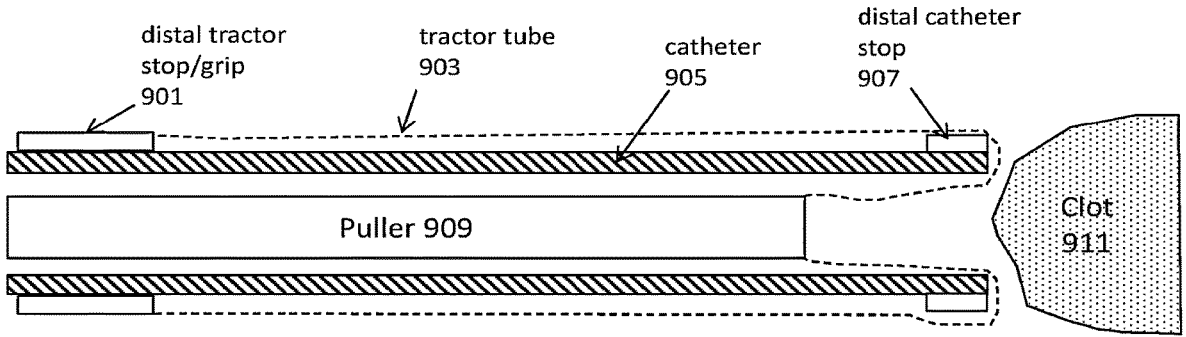
FIGS. 9A-9C illustrate an example of a mechanical thrombectomy apparatus that is configured as a reusable apparatus.
Figure 9B:
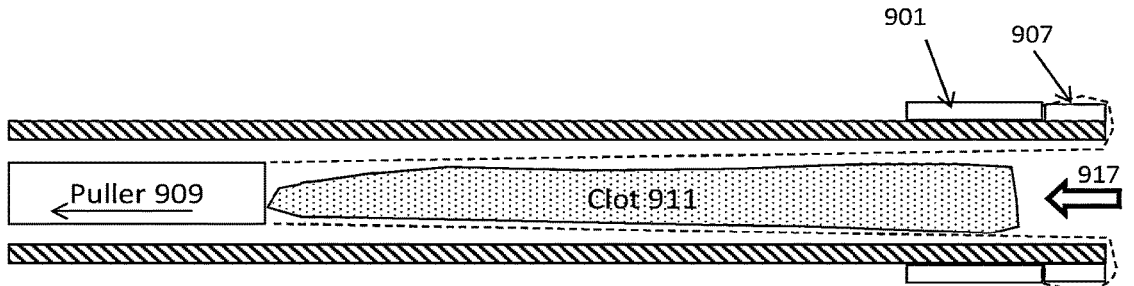
Figure 9C:
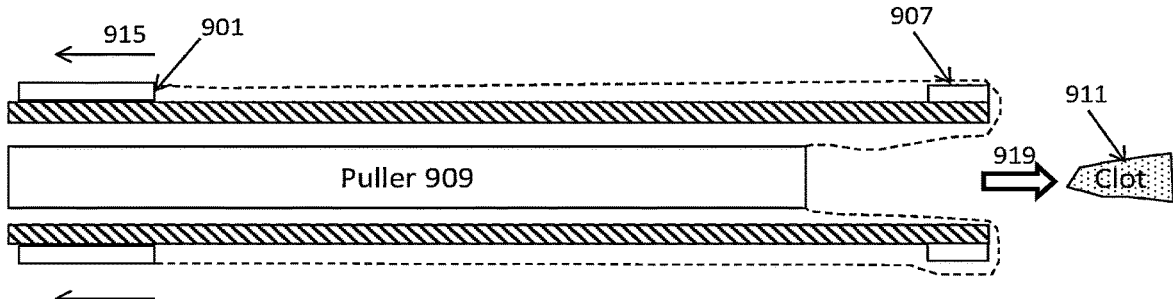

Also disclosed and described herein are reusable mechanical thrombectomy apparatuses. For example, FIGS. 9A-9C illustrate one reusable mechanical thrombectomy apparatus and method of use. In FIG. 9A, the apparatus includes a tractor tube (shown here as a knitted tractor tube 903). One end of the tractor tube is coupled to a puller 909 within the inner diameter of the elongate inversion support catheter 905. The puller in this example is configured as a hollow tube, which may allow passing of a guidewire and/or vacuum. The other end of the tractor is coupled to a distal tractor stop forming a finger grip 901 that is configured to slide over the outer surface of the elongate inversion support catheter. The finger grip may be sized for ease in grabbing manually and sliding proximally to "reload" the apparatus, as described below.

In FIG. 9A, the apparatus may be positioned near the clot 911, and the puller drawn proximally to invert and roll the tractor tube 903 into the elongate inversion support catheter 905, while advancing distally, and thereby pull the clot 911 into the elongate inversion support catheter (shown by arrow 917). Once grabbed, either fully or partially, as shown in FIG. 9B, the apparatus may be withdrawn from the vessel, the clot may be removed, as shown in FIG. 9C, by pulling the outer portion of the tractor tube proximally. The tractor tube is prevented from completely inverting into the elongate inversion support catheter by a distal stop 907 on the elongate inversion support catheter. For example, in FIG. 9C, the outer portion of the tractor tube may be manually pulled proximally 915 by sliding the distal tractor stop/grip 901 proximally, ejecting the compressed clot 911 from inside the apparatus. The device may then be rinsed and re-used to remove additional clot(s).

Figure 10A:
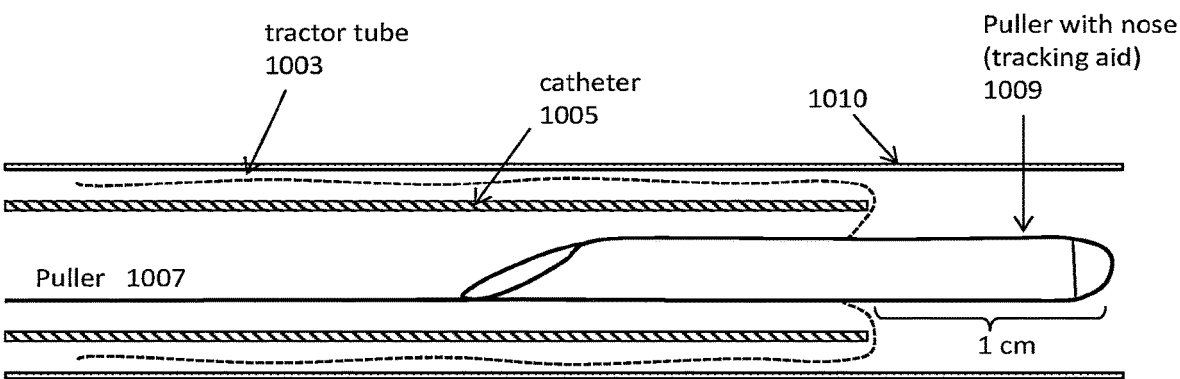
FIGS. 10A-10C illustrate variations of mechanical thrombectomy that may have improved tracking, e.g., within a vessel (e.g., lumen) and/or within the lumen of a catheter, such as an intermediate catheter.

Any of the apparatuses disclosed and described herein may be adapted to enhance tracking with an intermediate catheter and/or a lumen of a vessel. To assist the mechanical thrombectomy apparatus in tracking inside an intermediate catheter or tracking directly inside a native vessel (e.g., in which the puller, tractor tube and elongate inversion support catheter must track inside the distal end of an intermediate catheter), it may be beneficial to allow the puller to extend distally relative to the elongate inversion support catheter without disrupting the tractor tube. For example, FIG. 10A illustrates one example of a mechanical thrombectomy apparatus including a tractor tube 1003, elongate inversion support catheter 1005 and puller 1007, which is shown within an intermediate catheter 1010. In this variation, the distal end of the puller is configured to include a bumper region 1009 that can extend distally out past the distal end of the elongate inversion support catheter 1005. This nose element ("bumper") 1009 may be a constant stiffness or variable stiffness structure. For example, the distal end may be the softest section and the section most proximal to the distal end of the catheter may be less soft, and/or possible tuned to be of similar stiffness to the distal end of the elongate inversion support catheter. The tractor tube may be coupled proximal to the distal end, which may extend, e.g., approximately 1 cm, as shown.

In this example, the distal nose of the pull wire may be solid or cannulated (as shown). A cannulated nose may allow for guidewire access and also for aspiration through the intermediate catheter to allow vacuum forces to reach any clot or any other targeted element located in the body or vessel.

Figure 10B:
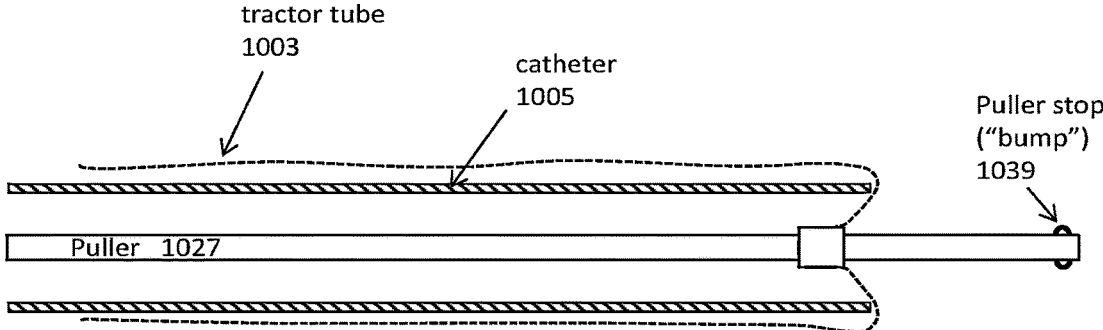

In use, the user may approach the clot within the lumen of the vessel with the nose region of the puller extended from the elongate inversion support catheter or extended within the elongate inversion support catheter. Once near the clot the nose region may be retracted inside the elongate inversion support catheter. Next the user may optionally pull a vacuum through the elongate inversion support catheter to engage the clot into the tip of the elongate inversion support catheter. Then, while slightly advancing the intermediate catheter, the tractor tube may be pulled proximally into the elongate inversion support catheter by pulling proximally on the puller, FIG. 10B illustrates another example of a mechanical thrombectomy apparatus having a puller (elongate puller 1027) which is configured to freely extend distally relative to the tractor tube, but when pulled proximally may engage with the tractor tube 1003 at one end to pull it proximally into the elongate inversion support catheter 1005. A portion (e.g., at or near a distal end region of the puller) may include one or more engagement regions (e.g., bumps, projections, etc.) that may engage with an annular ring or collar to pull the tractor tube proximally so that it may invert into the elongate inversion support catheter and therefore pull clot into the apparatus. In FIG. 10A, the puller can be extended beyond the tip of the elongate inversion support catheter at the user's preference when advancing the system to the clot. The male bump or other grabbing mechanism will engage on the proximal end of the tractor to pull in the clot.

Figure 10C:
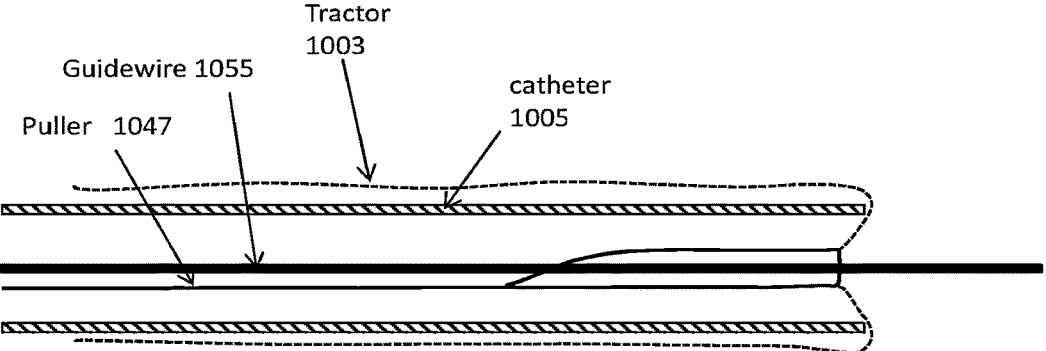

FIG. 10C illustrates another variation, in which the puller 1047 is configured to pass a guidewire and maybe extended or retracted using the guidewire 1055 in FIG. 10C, the construction that allows a guidewire to track through its lumen to aid in tracking within the vessel. For example, in FIG. 10C the puller includes a guidewire channel at the distal end region to which the tractor tube is attached.

In general, any of the mechanical thrombectomy apparatuses may include a modified puller that may enhance trackability, clot grabbing and/or pulling of the tractor tube into the elongate inversion support catheter. In addition to the examples shown and described in FIGS. 10A-10C, FIGS. 11A-11D show puller apparatuses that have a distal region adapted to include one or more projections.

Figures 11A, 11B, 11C, 11D:
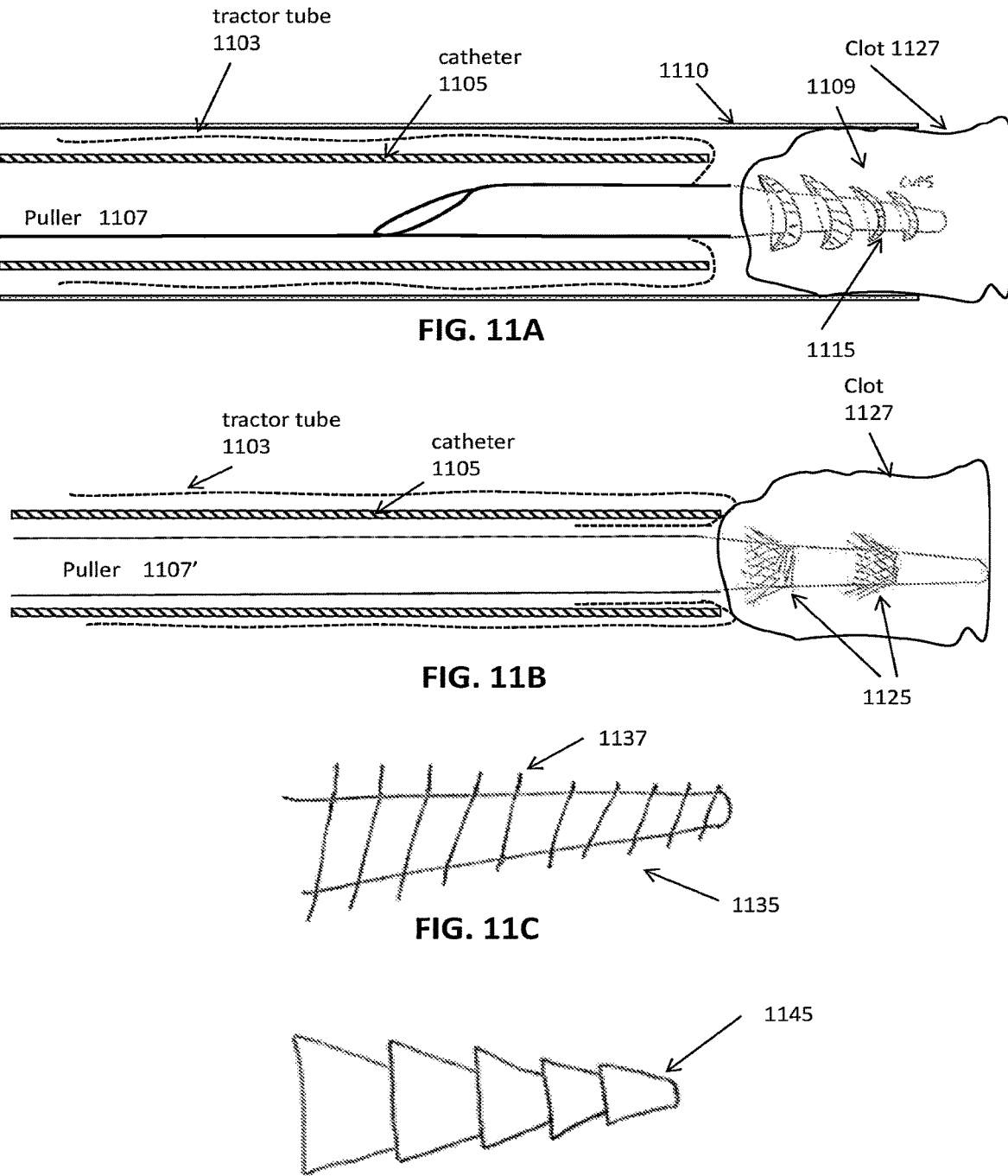
FIGS. 11A-11B illustrate another example of a mechanical thrombectomy that may have improved tracking, pulling of a clot and/or inverting of the tractor tube over the elongate inversion support catheter.
FIG. 11C shows an example of a distal tip of a puller configured to include a helical protrusion spiraling around the distal end.
FIG. 11D is an example of a distal end of a puller configured to have a stepped profile.

The puller tips shown in FIG. 11A-11D may enhance the trackability of the apparatus (e.g., the elongate inversion support catheter and/or tractor tube and/or puller) through tortuous anatomy, including the lumen of the vessel and/or an intermediate catheter. For example, FIG. 11A shows an apparatus including a tractor tube 1103, an elongate inversion support catheter 1105, and a puller 1107. In this example, the apparatus is used within an intermediate catheter 1110. The distal end 1109 of the puller 1107 is tapered and includes a plurality of projections 1115 extending away from the tapered distal end of the outer surface of the puller. In this example, the projections are configured as cups 1115 that have proximal-facing edges. The projections of this distal tip region may be used to grab and/or hook onto a clot when deployed; the puller may be advanced distally as described above and projected either by itself or over a pullwire into a clot 1127, as shown in FIG. 11A. When retracting the puller, the distal tip may pull the clot to the distal opening of the elongate inversion support catheter and/or it may advance the elongate inversion support catheter and tractor towards the clot. Any of these puller embodiments may be used with or without aspiration (e.g., through the elongate inversion support catheter, intermediate catheter and/or puller). Thus, in FIG. 11A, the distal end is configured as a cup-shaped male feature. The puller distal end region may be solid or cannulated and may be tapered (as shown in FIGS. 11A-11D) or non-tapered (e.g., cylindrical). In FIG. 11A, each projection ("cup") extends all or partially around the entire tip and more distal projections may have smaller diameters.

Another example of a puller having a plurality of projections is shown in FIG. 11B. In FIG. 11B, the projections are configured as fibers or fingers extending proud (and may be angled proximally) from the outer surface of the distal tip off the puller 1107'. In any of these examples, the puller (including the distal tip region of the puller 1107') may be solid or cannulated. In FIG. 11B, the distal tip region of the puller includes one or more sets of projections 1125 (e.g., fingers or fibers) directed proximally. The projections may be constructed from an open-end braid feature. The projections may be configured (oriented and/or soft enough) to slide into the clot when extending distally, but when retracting the puller proximally the projections may flare out and help anchor the tip of the puller the clot, as shown in FIGS. 11A and 11B. Optionally the projections may also engage with the tractor tube when pulled proximally and/or distally and may help pull the tractor and clot back through the elongate inversion support catheter.

FIGS. 11C and 11D illustrate alternative variations of puller tips including protrusions. In FIG. 11C, the puller tip 1135 includes one or more helical projections 1137 extending proud of the outer surface of the puller and extending around the puller. In some variations the projections are formed of a wire wrapped around the distal tip of the puller; the wire forms the male projection. FIG. 11D shows another example of a distal tip region 1145 having a stepped profile forming projections from the distal end of the puller in this example, the distal end is formed by a plurality (e.g., two, three, four, five, six, etc.) of cones that are arranged in progressively smaller sizes extending distally (forming a tapered tip region). The cones may be solid or cannulated. The tip may be formed of a plurality of connected elements or may be a unitary (or fused) element.

Inversion Support Catheters

As discussed above, any of the apparatuses disclosed and described herein may include an elongate inversion support catheter having a distal end and a distal end opening, in addition a tractor tube (e.g., a knitted tractor tube). In operation, the tractor tube extends over an outer surface of the elongate inversion support catheter, and inverts into the distal end opening of the elongate inversion support catheter when the end of the tractor tube is pulled into the inversion support catheter, for example, by pulling on the elongate puller coupled to a first end of the tractor tube that is within the inversion support catheter. Thus, as mentioned above, the inversion support catheter must have a sufficient column strength so that it does not buckle or collapse as the tractor tube is pulled into the distal end of the inversion support catheter, even when pulling a hard clot.

The inversion support catheter may be configured so that it does not collapse (e.g., buckle) when 500 g or less of compressive force is applied (e.g., at least about 700 g, 600 g, 500 g, 400 g, 300 g, etc. of compressive force), particularly when the apparatus is configured for neurovascular applications. For peripheral vascular applications, the elongate inversion support catheter may be selected or configured to withstand at least 1500 g of compressive force (e.g., at least about 2000 g, 1900 g, 1800 g, 1700 g, 1600 g, 1500 g, 1400 g. etc. of compressive force). In addition, the inversion support catheters disclosed and described herein may be configured so that they do not foreshorten substantially when the tractor tube is pulled over the distal end (e.g., do not foreshorten by more than 2%, 3%, 4%, 5%, 6%, 7%, 8%, 9%, 10%, etc.).

It may also be desirable that the inversion support catheters maintain sufficient column strength even when tracked or tracking though highly tortious anatomical regions. FIG. 12 is an example of a tortious neuroanatomical region, showing a drawing of a the internal carotid artery, which includes multiple regions (labeled as regions 1, 2, 3, 4 and 5 in FIG. 12). The inversion support catheters disclosed and described herein may have sufficient column strength and may have a structure configured to resist buckling and compression when pulling a tractor tube so that it rolls into the distal end opening of the inversion support catheter (often applying up to 500 g of force or more in compression), yet still be sufficiently flexible to track through such tortious regions of the vasculature including regions 1-5 of an internal carotid artery such as the example shown in FIG. 12.

A number of inversion support catheter designs have been examined by the applicants. Many of the inversion support catheters tested, even those having cut-our regions that enhance flexibility, and those with support structures to enhance column strength (e.g., withstanding up to 500 g or more of compression force), do not have both a sufficient column strength to resist buckling/compression and a sufficient flexibility to navigate a region having a tortuosity equivalent to that in a model internal carotid artery, such as the one shown in FIG. 12. Disclosed and described herein are inversion support catheters configured to meet these criteria. In particular, disclosed and described herein are inversion support catheters having a plurality of slots ("slotted inversion support catheters") in which the slots are configured to provide both column strength and flexibility. Slots are typically formed substantially transverse to the long axis of the catheter, wherein substantially transvers includes e.g., +/–a few degrees off transverse (e.g., +/–2 degrees, +/–3 degrees, +/–4 degrees, +/–5 degrees +/–7 degrees, +1-10 degrees, +/–12 degrees, etc.). The slots may be cuts through the catheter that extend approximately transverse to the length of the inversion support catheter (at a pitch of between +/–a few degrees, e.g., a pitch of between 0.05 to 0, etc.). The slots may extend, for example, between 60 and 180 degrees (e.g., between 90 and 180 degrees, between 100 and 170 degrees, between 110 and 160 degrees, between 120 and 150 degrees, etc.) around the circumference of the inversion support catheter.

In some of the variations disclosed and described herein, the slots are formed, e.g., by laser cutting, rectangular cut-out regions. The slots may be configured as compressed slots, e.g., by heat-setting the catheter or a portion of the catheter into a longitudinally compressed state. In the compressed state, the slots be configured so that the ends of the slots, which are not typically compressible, have a fixed width, and the region between the ends of the slots is compressed so that the width of this region is less than the width of the ends of the slots. See, e.g., FIGS. 13A-13C. For example, In FIG. 13A a "neutral" slot is shown cut through a catheter, and typically curving around the radius of the catheter. The slot shown in FIG. 13A has end regions 1301, 1305 of the slot that each have a width (w) that is approximately the same width as the middle region 1303 between the ends ($w_2$). For example, the width may be between 0.01 and 0.0001 inches (e.g., between 0.005 and 0.0001, between 0.001 and 0.0001, etc.). The neutral slot shown in FIG. 13A may be compressed, e.g., by applying a compressive force on the long axis of the catheter and heat-setting the catheter in the compressed configuration. This may form a compressed slot, also referred to herein as a "closed" slot or "closed cell" slot. In FIG. 13B a closed rectangular slot is shown, having edge regions that have a width ($w_1$) that is substantially the same as in the neutral position, however the middle region 1303 between the ends 1301, 1305 has a width ($w_2$) that is less than the width at the ends of the slot (e.g., $w2 < w_1$, e.g., $w_2 < 95\%$ $w_1$, $w_2 < 90\%$ $w_1$, $w_2 < 85\%$ $w_1$, etc.).

The slot may also be opened, as shown in FIG. 13C. In some variations, the slot is opened by applying a tension (e.g., by pulling) force on all or a portion of the elongate length of the catheter into which the slot is formed, and heat-setting the slot in the resulting expanded configuration. In FIG. 13C the middle region 1303 of the slot has been expanded to have a width ($w_2$) that is greater than the width ($w_2$) of the end regions 1301, 1305. This may be referred to an open or open cell configuration for the slot. For example, in an open configuration of a rectangular slot, $w_2 > w_1$. In some variations, in which $w_2$ is much larger than $w_1$ (e.g., $w_2 >> w_1$, e.g., $w_2$ is greater than about $2 \times w_1$, $w_2$ is greater than about $2.5 \times w_1$, $w_2$ is greater than about $3 \times w_1$, $w_2$ is greater than about $4 \times w_1$, $w_2$ is greater than about $5 \times w_1$, etc.) these slots may be referred to as super-open slots.

Any of the inversion support catheters disclosed and described herein may be configured so that the distribution of slots is non-uniform along the length of the catheter. For example, the distal end region of a slotted inversion support catheters (e.g., the distal most region of the catheter between 1-50 mm from the distal end, e.g., between 2-30 mm, between 2-20 mm, between 2-10 mm, etc.) may include open-cell slots (all or some open-cell slots. The portion of the catheter proximal to this distal end may include closed cell or normal slots. In some variations, the catheter may include both open-cell and closed-cell slots arranged around and along the distal end region. The percentage of open-cell slots may be, e.g., between 0.1%-80% of the total number of slots in the distal end region (e.g., between 0.1% to 70%, between 0.1% to 60%, between 0.1% to 50%, between 0.1% to 40%, between 0.1% to 30%, between 0.1% to 20%, between 0.1% to 10%, between 0.1% to 5%, etc).

As will be described in greater detail herein, in some variations, the catheter, and particularly the distal end region, may include super open-cell slots. In particular, the percentage of super open-cell slots to other open-cell slots and closed-cell slots may be less than 50% (e.g., less than 40%, less than 30%, less than 20%, less than 10%, less than 5%, less than 1%, less than 0.5%, etc.). As mentioned, other slots may be closed-cell slots and/or may have different dimensions. The region of the inversion support catheter proximal to the distal end region may have a slotted configuration of closed-cell slots.

It is hypothesized that closed-cell slots may help provide column strength to an inversion support catheter, since the adjacent walls of the slot are not able to compress much. However, closed-cell slots are less flexible than slots in the neutral configuration or in the open (or super open) configurations described above. Towards this end, variations of catheters having a proximal region that included primarily or exclusively closed-cell slots with a distal end region (e.g., distal 1-50 mm) that was primarily or exclusively open-cell slots were initially examined.

For example, FIG. 14A illustrates three examples of inversion support catheters, 1401, 1402, 1403. These inversion support catheters have a slotted pattern of cuts (formed by laser cutting). The inversion support catheters were laser cutting a length of NiTi tubing. The entire length of the laser-cut catheter was then compressed and heat set to close the cells formed by the laser cutting. The cut-out regions (e.g., cells) were then compressed so that the separation of the opposite sides of the cut-out region transverse to the length of the catheter had a separation of less than 95% of the original cut-out diameter (e.g., if the original cut-out diameters is 0.001", the compressed configuration is 0.0001") over at least a portion of the slot (e.g., a middle region of the slot).

Catheters having compressed cut-out regions such as this may show good column strength (e.g., resisting up to 500 g of compression force without bucking), however, they generally were not capable of tracking a tortious model of the vasculature such as shown in FIG. 12, and typically failed to track further than the first (1) or second (2) regions of the model.

To improve tracking, catheters having compressed cut-our regions such as those shown in FIG. 14A were re-heat set at their distal ends while applying a stretching force. Expanding just the distal end region (e.g., the distal 12 mm, distal 15 mm, distal 20 mm, distal 30 mm, distal 40 mm, distal 50 mm, etc.) to have larger-diameter gaps (open-cell slots) was performed on all three of the catheters shown in FIG. 14A. In FIG. 14A, the middle 1402 and right devices 1403 were each first compressed and heat-set in a compressed configuration and then the distal ends were expanded to have a uniform stretching and separation of the gaps in the slotted cells, forming open-celled slots in this distal end region. The slots shown have a middle width between the ends of the slots that is the same or slightly larger than the width of the end regions (e.g., the width of the middle region of the slot is between about 100.5% and 120% of the width of the end regions of the slot). These devices 1402, 1403 performed better than catheters having just closed-cell slots, and were able to track slightly further (e.g., to the second (2) or third (3) regions in the internal carotid model show in FIG. 13).

Figures 16A, 16B, 16C, 16D, 16E, 16F, 16G:
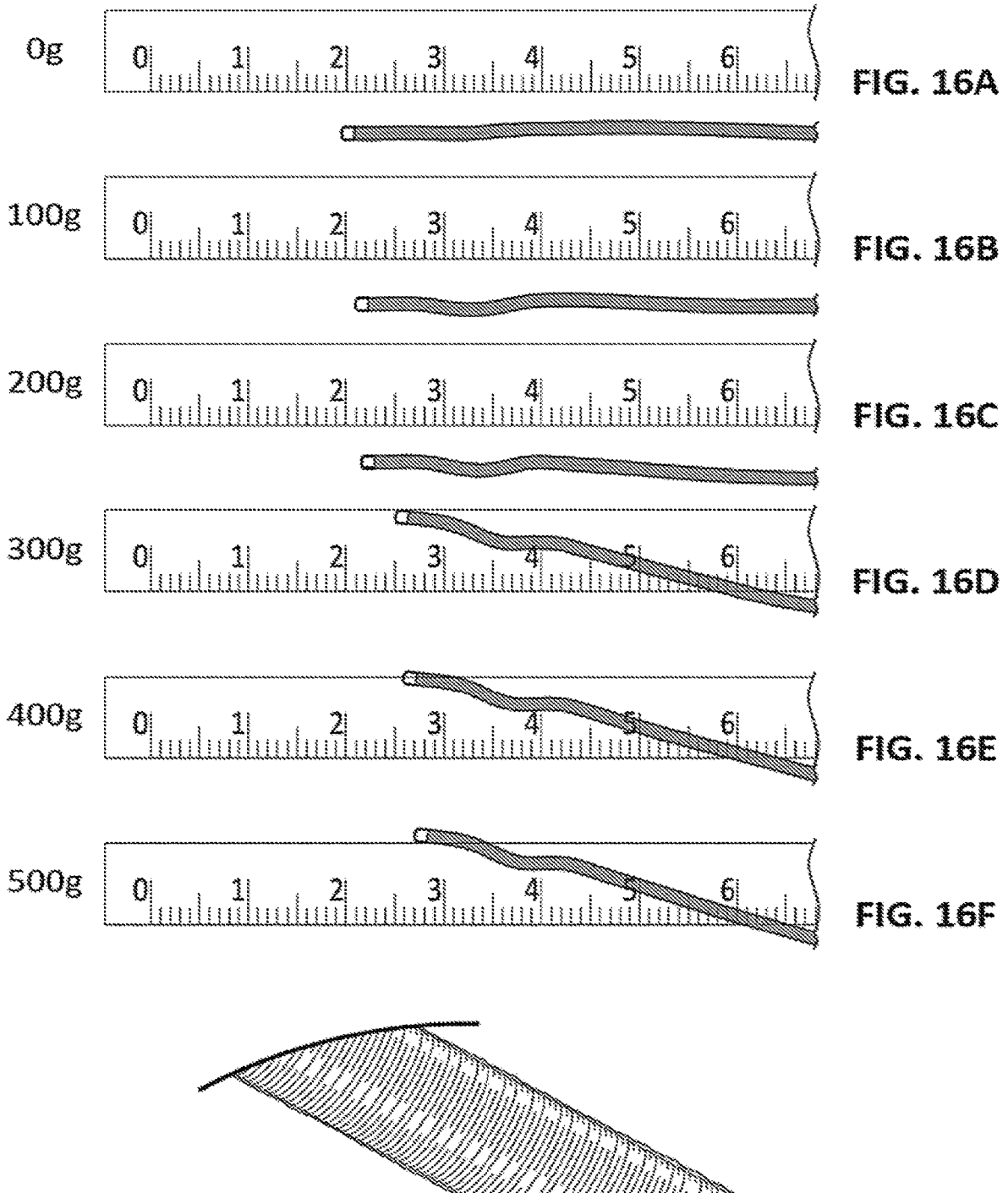
FIGS. 16A-16F illustrate increasing compression force applied to an exemplary slotted catheter, showing minimal compression/kinking.
FIG. 16G shows the distal end of the device shown in FIGS. 16A-16F.

For example, FIGS. 16A-16F illustrate a slotted inversion support catheter first formed to have uniformly closed-cell slots by heat-setting in a longitudinally compressed configuration, and then heat-setting the distal end region in a stretched (e.g., the distal 2 cm) configuration. The apparatus was then jacketed by lamination of a jacket material over the catheter. As shown in FIGS. 16A-16F, such devices had a column strength that was sufficiently high to avoid significant kinking. Although a slight bend occurred beginning at 100 g of compression (FIG. 16B), this bend did not increase significantly even up to 500 g of compression (FIG. 16F). FIG. 16G shows a slightly enlarged view of the distal end region of the catheter.

Figures 17A, 17B, 17C, 17D, 17E:
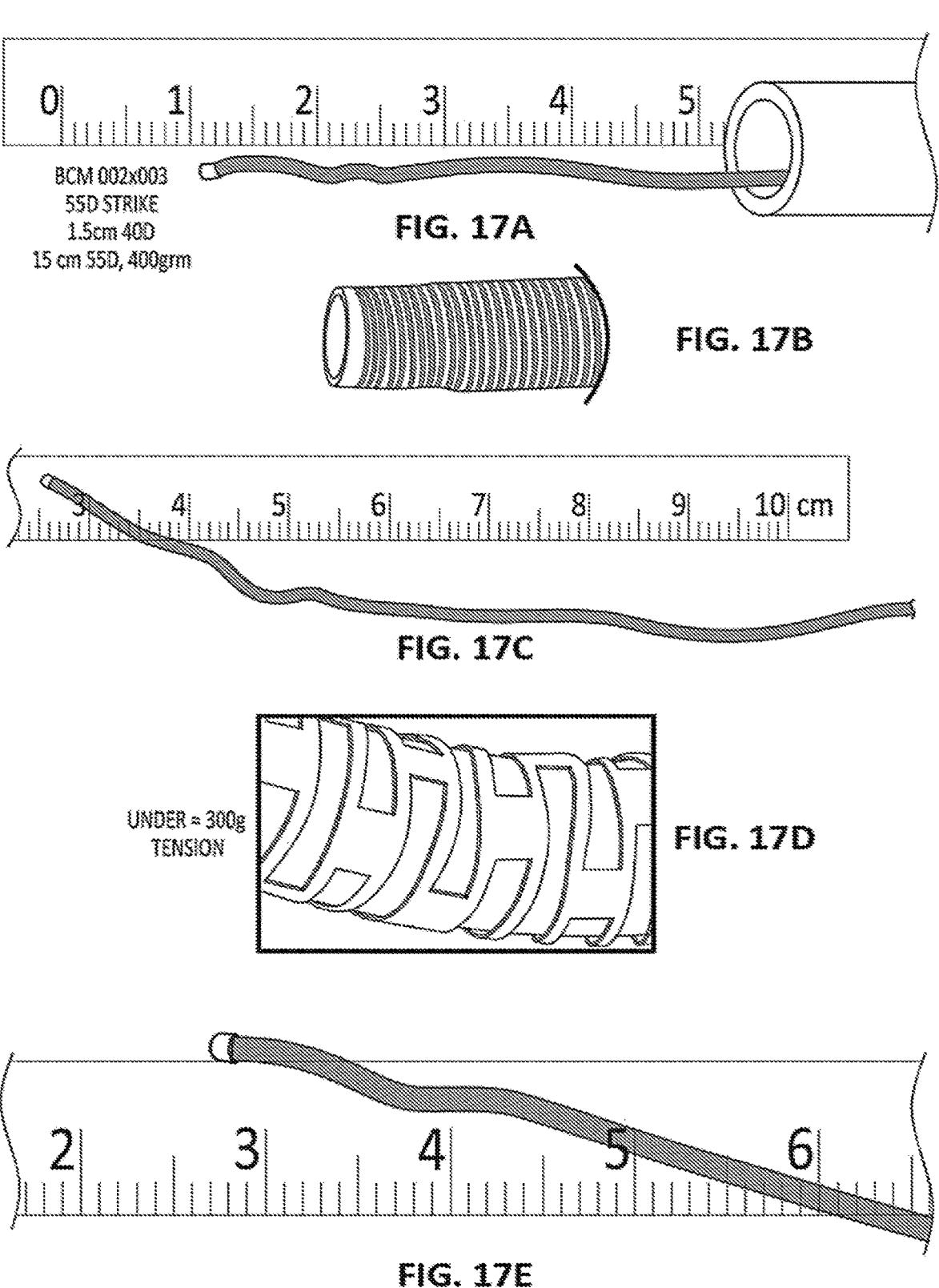
FIGS. 17A-17B illustrate another example of a slotted inversion support catheter undergong 400 g of compression, showing kinking and shortening of the catheter.
FIGS. 17C-17D illustrate a second example of a slotted inversion support catheter undergoing 400 g (FIG. 17C) and 300 g (FIG. 17D) of compression; this example also kinked/shortened.
FIG. 17E illustrates another example of a slotted inversion support catheter similar to that shown in FIG. 16G, above.

FIGS. 17A-17C illustrate, for comparison, other slotted catheters (e.g., catheters having cut-our regions) that kinked in compression. For example, FIG. 17A (shown enlarged in the inset FIG. 17B) is an example of a first catheter having slots cut therein (neutral slot configuration), showing substantial kinking and compression when 400 g of compression was applied. Similarly, FIG. 17C (with an enlarged view of the slots shown in FIG. 17D) shows another example of a catheter having somewhat large, open-cell slots along the length of the catheter; this catheter also showed a great deal of kinking and compression. FIG. 17E is another example of a catheter of FIGS. 16A-16G), repeated here to show a side-by-side comparison.

During the process of stretching the distal end of catheters that had been heat-set in a compressed configuration, some catheters (see, e.g., the catheter 1401 on the left in FIG. 14A, shown in greater detail in FIG. 148), were inadvertently expanded so that apparent "defects" 1409 were formed in a small minority of some of the cells, forming super open-celled slots. These defects resulted in a subset of slots/cells that were opened to a greater degree than other slots, which were either not opened (remained closed cell, having a maximum width of the middle region that is less than the maximum width of the end regions), were neutral (in which the width of the middle region is approximately the same as the width of the end regions), or were only slightly opened by the stretching process, forming open-cell slots (e.g., sots having a maximum width of the inner region that is between $1\times$ and $1.5\times$ the diameter of the end regions, e.g., between $1\times$ and $2\times$, between $1\times$ and $2.5\times$, between $1\times$ and $3\times$). Surprisingly, catheters having these "defect" regions (super open-cell regions having a maximum width of the middle region that is greater than $1.5\times$ the width of the end regions, e.g., greater than $2\times$, greater than $2.5\times$, greater than $3\times$, etc.) had a greater column strength (e.g., less buckling at an applied, e.g., 500 g, compression force) and better tracking. Such devices were able to track through the model of tortious vasculature, such as the internal carotid model shown in FIG. 12, completely, e.g., to region (5) or beyond.

Figures 14C, 15:
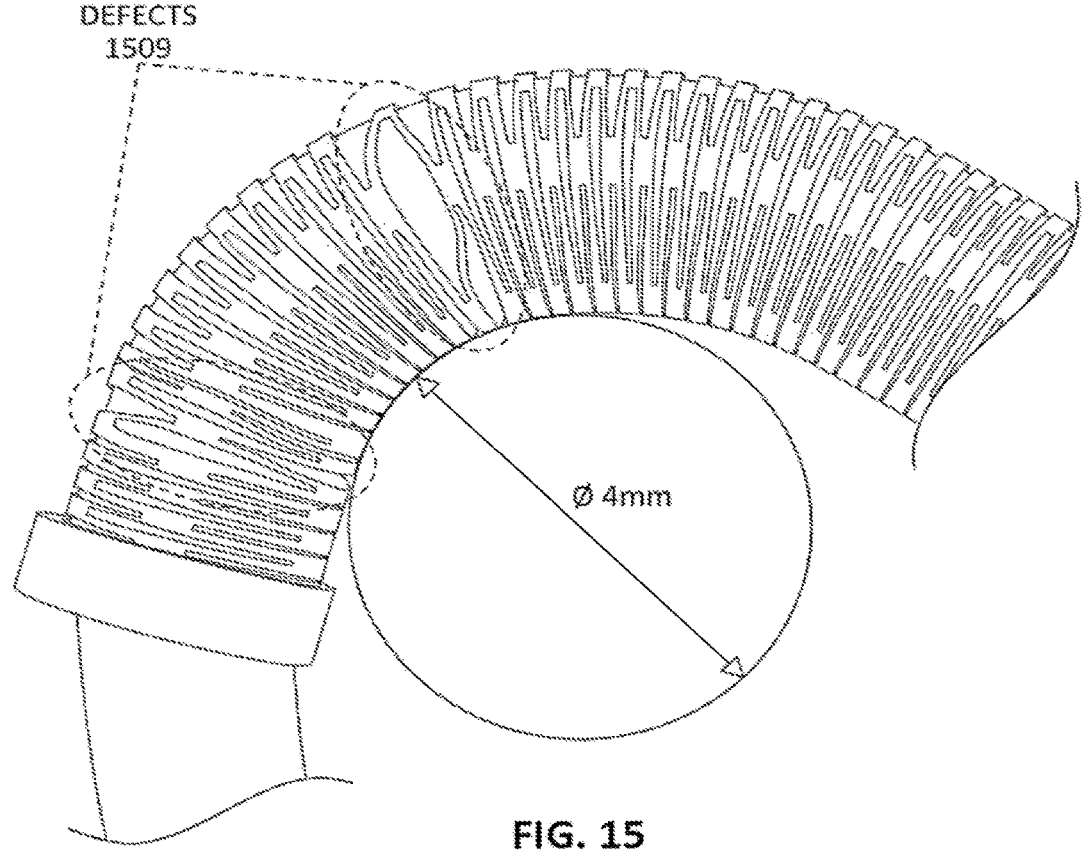
FIG. 14C describes a pattern used to form slotted inversion support catheter such as the ones shown in FIG. 14A.
FIG. 15 illustrates bending of a slotted inversion support catheter having a distal end region with a combination of open-cell and closed-cell slots cut into the distal ends; in this example, only two open-cell regions are included in the distal end region.

FIG. 15 illustrates an example of one such device including these introduced "defects" in the distal end region of the catheter. The defects in this example are formed in a subset of cells formed by cutting the slots in the distal end region of the catheter. These defects may be referred to as super open-cell slots (compared to the other closed cell and/or open-cell slots in the distal end region) in which the separation between long and opposite sides of the slot are separated by greater than $1.5\times$ the separation of the majority of the closed cell slots in the distal end region. For example, the maximum separation between the opposite long side of the open cell configuration may be greater than $1.5\times$, greater than $2\times$, greater than $2.5\times$, greater than $3\times$, greater than $3.5\times$, greater than $4\times$, greater than $4.5\times$, greater than $5\times$, etc. the maximum separation between the opposite long side of the closed-cell slots at the ends of the rectangular slot. The super open-cell (defect) slots may be distributed within the distal end region and may be present or absent from the proximal region (which may also include slots).

For example, the distal end region of the elongate inversion support catheter may include at least two types of slots cut generally transverse to the length of the elongate inversion support catheter through the wall of the elongate inversion support catheter, based on the size of the gap between opposite walls of the slots, including open-cell slots and super open-cell slots (and/or closed-cell slots or neutral slots). The slots may extend around the circumference of the catheter so that there are between 4 and 1 slots per rotation of the catheter (e.g., between 2 and 3, approximately 2.5, etc.). The opposite walls of the slot may be the walls that are transverse or approximately transverse to the long axis of the catheter. The closed cell slots may have a maximum separation between the opposite walls of c inches (e.g., c may be, for example, 0.0001 inches, 0.0002 inches, 0.0005 inches, 0.001 inches, etc.). The open-cell slots and may have a maximum separation between the opposite walls of o inches, where o is between $1\times$ and $1.5\times$ the width of the ends of the slot $w_1$ (e.g., o is between $1\times$ and $1.5\times$ wt, e.g., o is between $1\times$ and $2\times$ $w_1$, o is between $1\times$ and $2.5\times$ $w_1$, o is between $1\times$ and $3\times$ $w_1$, etc.). The super open-cell slots may have a maximum diameter o that is greater than $1.5\times$ $w_1$, greater than $2\times$ $w_1$, greater than $2.5\times$ $w_1$, greater than $3\times$ $w_1$, greater than $4\times$ $w_1$, greater than $5\times$ $w_1$, greater than $6\times$ $w_1$, greater than $7\times$ $w_1$ greater than $8\times$ $w_1$, greater than $10\times$ $w_1$, etc. The distribution of super open cell slots to other slots may be uniform or non-uniform, including random. The majority of the slots in the distal end region may be closed and/or open-cell slots, particularly compared to super open-cell slots. For example, there may be between 0.001% and 20% super open-cell slots in the distal end region (e.g., between 0.001% and 10%, between 0.001% and 5%, between 0.01% and 5%, between 0.1% and 5%, etc., between 0.001% and 1%, etc.). For example, there may be between 0.5 and 20 super open-cell slots for every cm length of catheter (e.g., between 1 and 20, between 0.5 and 15, between 0.5 and 10, between 1 and 10, etc.). The super open-cell slots may be oriented at different radial positions around the catheter.

FIG. 14C illustrates an exemplary laser cut pattern for an inversion support catheter such as the ones shown in FIG. 14A. As mentioned above, a length of NiTi tubing may be cut (e.g., laser cut) to form slots, and these slots may be compression heat set along the entire length of the catheter to form closed-cell slots. The catheter may then be re-heat set with the distal end region stretched, to form open-cell slots. In some variations, a small number of these slots may also be formed as super open-cell slots. In FIG. 14C, a variety of pitches are shown (e.g., between 0 and 0.01) for the slots.

FIG. 15 illustrates an example of an inversion support catheter in which the distal 5 mm of the catheter were treated (by stretching and heat setting) to introduce two "defects" (super open-cell regions) 1509. Although the majority of the slots in the distal end remained simply open-cell slots, these super open-cell slots (which have a maximum width of greater than $1.5\times$ the width of the ends of the rectangular/oval slot) greatly enhanced the flexibility and tracking of the catheter; the exemplary catheter in FIG. 15 also had a column strength sufficient so that little or no kinking resulted even when applying up to 500 g of compressive force, as may be applied when rolling a tractor tube into the catheter to capture a hard and/or large clot.

Figures 18A, 18B, 18C, 18D, 18E:
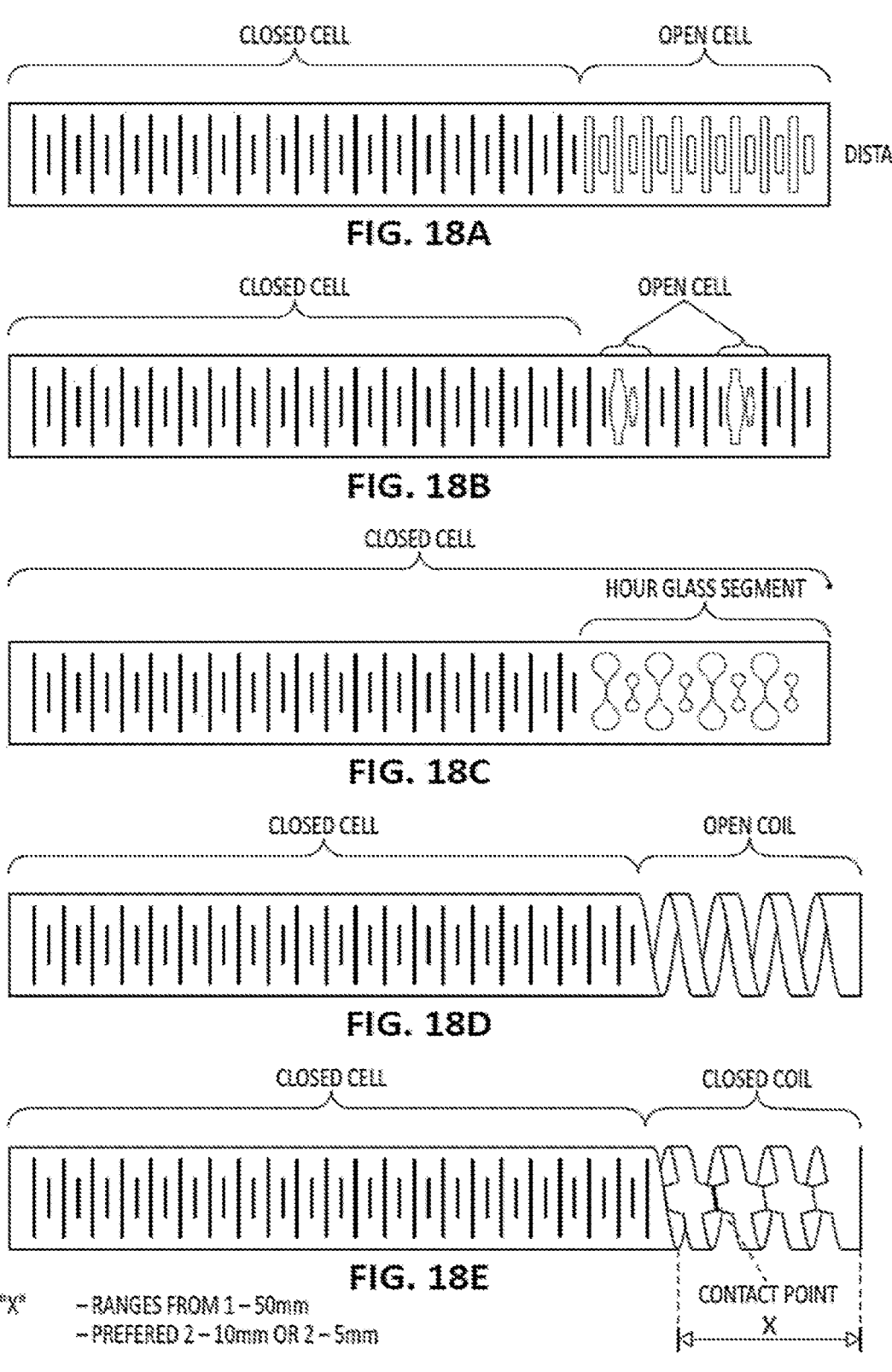
FIGS. 18A-18E illustrates examples of slotted inversion support catheters having proximal regions with close-cell slots and distal regions with open-cell cut out regions (including slots).

In any of the apparatuses disclosed and described herein, distal end region (e.g., the distal 1-50 mm, distal 2-10 mm, etc.) may have open-celled slots (and/or super open-cell slots) compared the more proximal regions, which may be formed of closed cell slots. For example, FIGS. 18A-18E illustrate examples of inversion support catheters having a combination of open cell and closed cell cut-out regions. In FIG. 18A, the distal end region includes open cells, which may be configured as described above. In FIG. 18A, the majority or all of the distal end region include open-celled slots, compared to the proximal region which are closed-cell slots. In FIG. 18B, a percentage of the cut-out slots are open-celled, but not all (e.g., between 0.1% and 80%, etc.) of the slots are open-cell slots. In FIG. 18C, the distal end region includes slots that are tapered in the middle (e.g., "hourglass" slots) so that each slot includes open-celled and closed-cell regions; the proximal region is shown as all closed-cell slots. Such bi-lobed slots (also referred to as hourglass, barbell and/or dog bone slots) may also have improved tracking and compression strength, comparable to the device having super open-cell slots discussed above; these will be described in greater detail below.

In FIG. 18D the distal end region includes an open coil configuration. In FIG. 18E, the distal coil region is referred to as "closed coil" as the adjacent coils are spaced (over at least a portion of their length) very close together. Although FIGS. 18A-18E show catheters having a stark transition from the proximal and distal end regions, in some variations the transition may be more gradual, so that the device transitions gradually from close cell (proximal) to open-cell (distal) cut-out regions.

FIGS. 19A and 19B illustrate open and closed cell configurations of cut-out regions that may be formed by heat-setting the catheter in compression. In FIG. 19A, a rectangular slot is cut from the catheter as described above in an open configuration, having a separation between the opposite long walls of the slot that is $z_1$ wide (shown on left) in the closed configuration (under compression) the slot may be heat-set to have a diameter over the middle ($x_2$) region that is $z_2$ wide. The edge region of the slot (e.g., regions $x_1$ and $x_3$) may be nearly incompressible near their edges and may therefore remain separated. As described in FIG. 19C, the design of FIG. 19A may have dimensions in the closed cell configuration so that $x_2$ is between about 5% of $x_1$ and 95% of $x_1$. For example, in the compressed, close-cell configuration, the compressed region x2 may be the middle 1% to 90% of the total length (x) of the slot. Similarly, the separation $z_2$ between in the long walls of the slot in the compressed configuration may be less than or equal to 95% of the original separation, $z_1$. For example, if the original separation ($z_1$) is 0.001 inches, the compressed separation ($z_2$) may be approximately 0.0001 inches. Generally, the open cell separation may be between, for example, 0.0005 inches and 0.010 inches.

The centrally-tapered slots (hourglass configuration) shown in FIG. 19B in the open-cell and closed-cell configurations may include larger width regions ($y_1$) one either side of the slot, separated by a narrow region $z_1$. The lengths of the wider regions ($x_1$, $x_3$) and the intervening narrower region ($x_2$) may add up to the total length of the slot, x. In the closed cell configuration, the separation of the wider regions ($y_1$) may remain approximately the same, while the middle region, $z_2$ may be much smaller than the original, open-cell width, $z_1$. As exemplified in FIG. 19C, the configuration of FIG. 19B, may have a closed cell configuration in which the closed cell width $z_2$ is less than or equal to 90% of the original open-cell width $z_1$. The narrower regions is typically centered (but may be offset) within the slot, and may include the middle 5%-95% of the slot. For example, an hourglass-cut slot such as the one shown in FIG. 19B may have an open-cell maximum width of between 0.0005 inches and 0.010 inches at the wide regions on either end and a narrower central region that is between about 10% and 50% of the width of the wider ends ($y_1$).

FIGS. 20A-20C illustrate alternative configuration of slots that may be cut into the catheter having a centrally-tapered (e.g., hourglass- or barbell-shape) configuration. These configurations typically include an open cell region even in the compressed configuration.

Figure 21A:
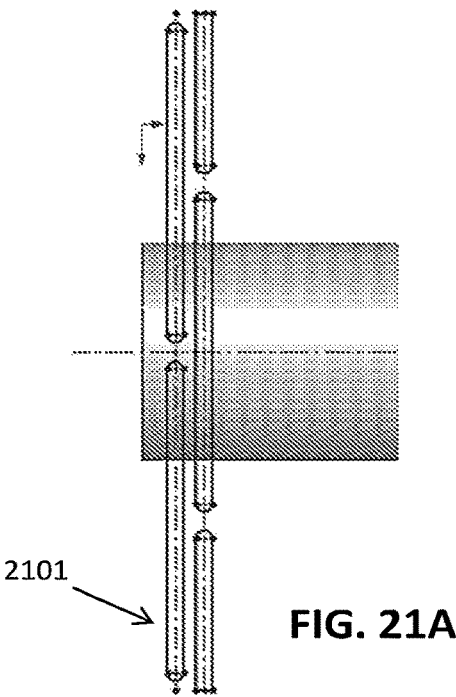
FIGS. 21A-21C illustrate another example of a slotted catheter having a brick-like pattern of aligned slots.
Figure 21B:
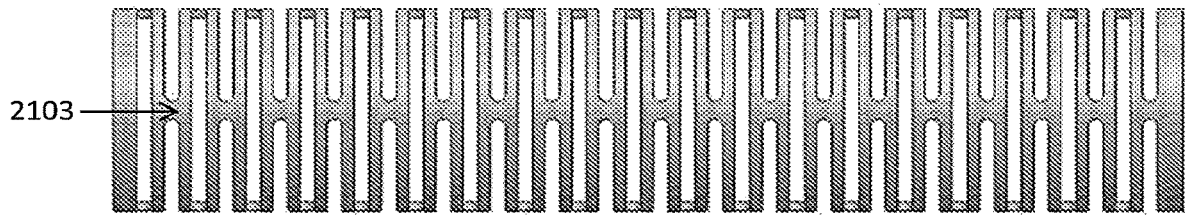
Figure 21C:
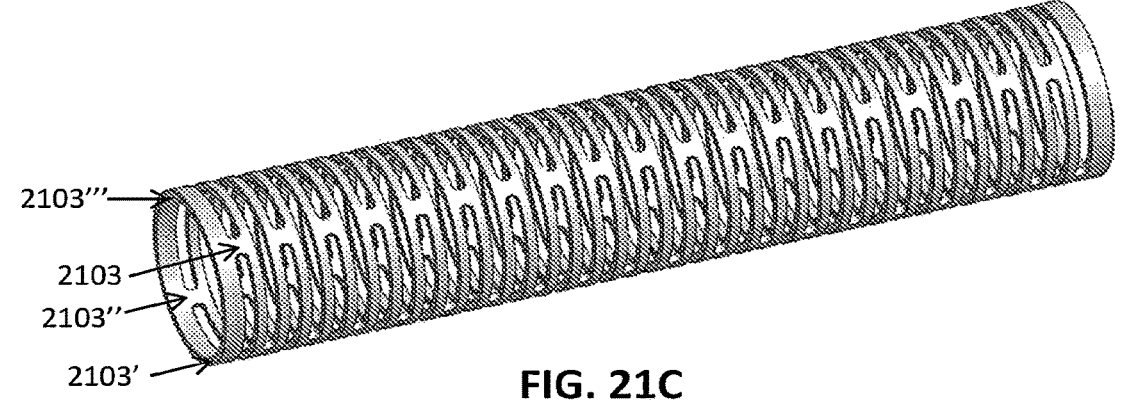

FIGS. 21A-21C illustrate additional slotted catheter designs having regions of closed and open sections that may be formed by cutting or pattering, without requiring heat setting. Alternatively, or additionally, heat setting may be used. In FIG. 21A, the cut pattern 2101 is shown, with slots arranged in an overlapping pattern (a brick stacked pattern). FIG. 211B shows a side view, showing the pattern of alternating slots arranged adjacently along the length of the catheter so that there are columns of high-compression strength in the noon 2103, 3 o'clock 2103', 6 o'clock 2103", and 9 o'clock 2103'" positions radially around the circumference of the slotted catheter (or the slotted portion of the catheter). FIG. 21C shows a side perspective view of the slotted catheter. Other overlapping patterns may be used, including patterns in which high-support regions 2103, 2103', 2103", 2103'" line up along the long length of the catheter in more or fewer than the 4 radial locations shown in FIG. 21A-21C (e.g., in the noon, 4 o'clock, 8 o'clock position, etc.). In some variations the overlapping pattern creates a spiral or helical pattern of high-support regions along the length of the catheter. As mentioned, this pattern may also be compressed and heat-set in a closed-cell configuration. Further cells can be open-cell or closed-cell in different regions along the length of the catheter.

Figure 22A:
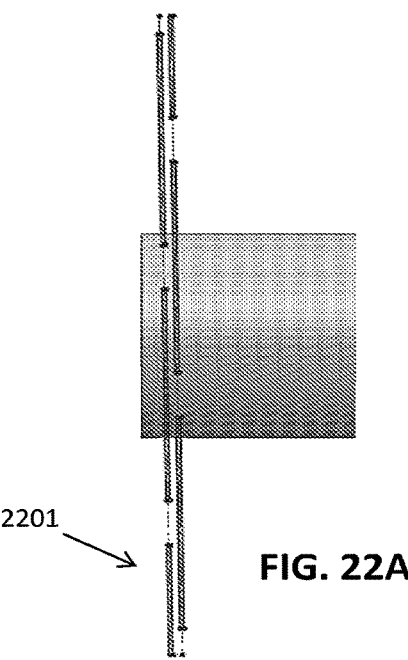
FIGS. 22A-22C illustrate another example of a slotted catheter having a spiral-like pattern of aligned slots.
Figure 22B:
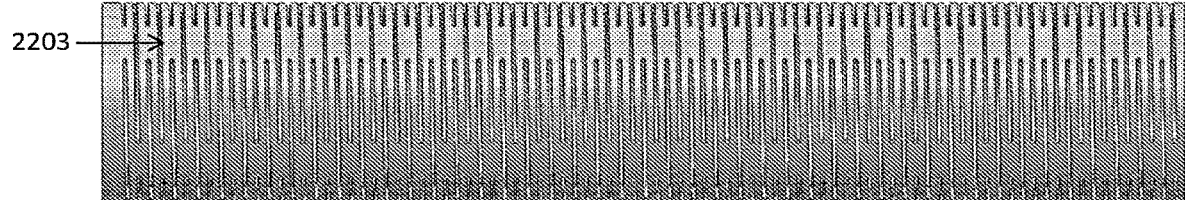
Figure 22C:
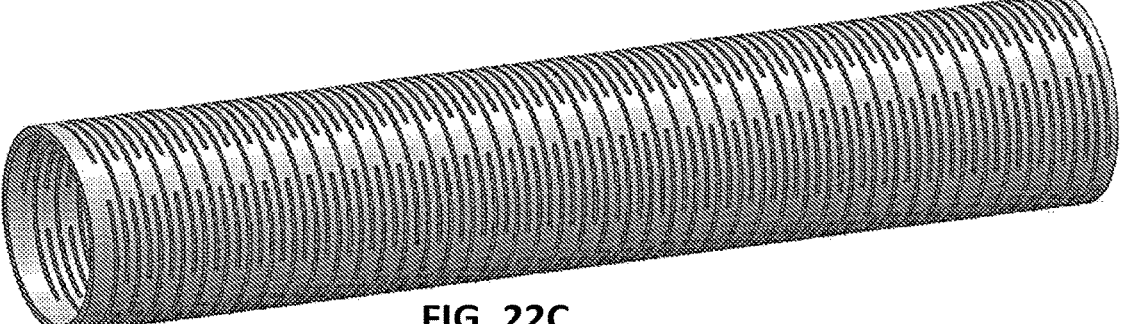

Another example of a slotted catheter design is shown in FIG. 22A-22C. FIG. 22A shows the cut pattern 2201 comprising a narrow spiral cut pattern. The open-cell spiral design pattern may be shaped (e.g., by applying compression and/or pulling longitudinal force and shape-setting) to be open-cell or closed-cell along the entire length of along portions of the length of the catheter. In FIGS. 22A-22C, the spiral pattern includes aligned overlapping/adjacent regions so that there are five columns of higher-support regions down the elongate length of the catheter, FIG. 22B shows a side view, and FIG. 22C shows a side perspective view.

Figure 23A:
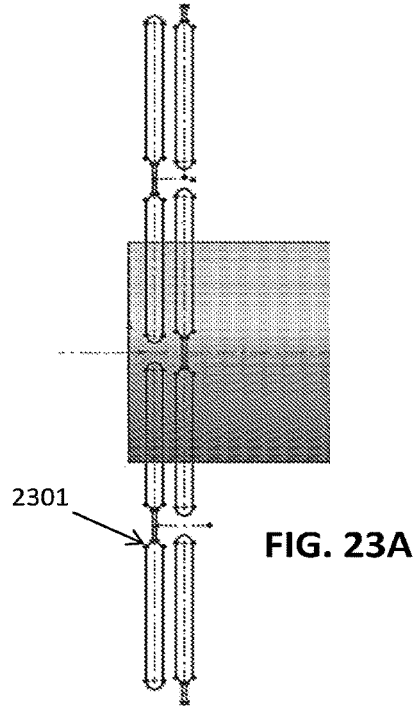
FIGS. 23A-23C illustrate another example of a slotted catheter having a dog bone pattern of aligned slots.
Figure 23B:
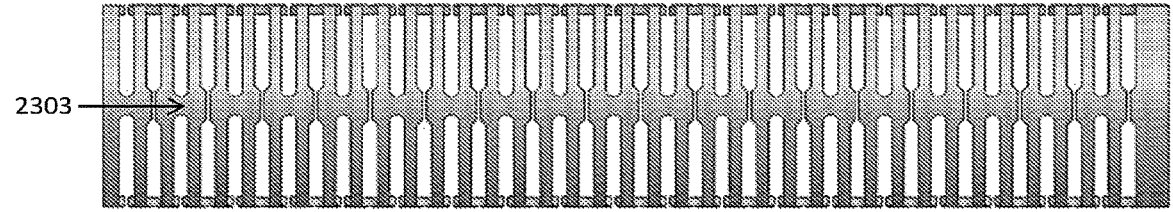
Figure 23C:
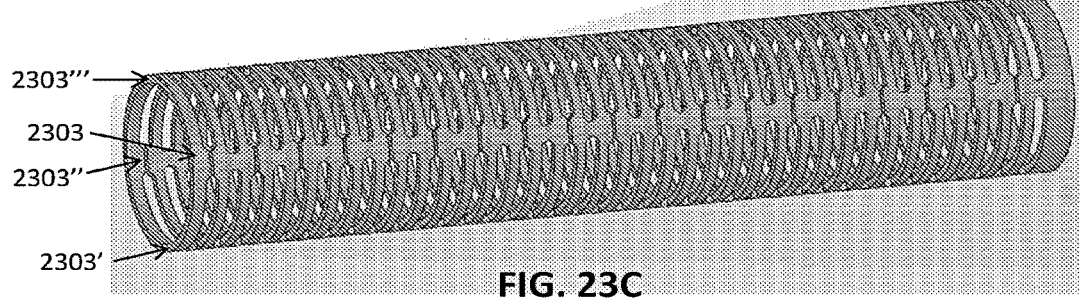

FIGS. 23A-23C illustrate another variation of a slotted catheter pattern design. In this example, the slotted pattern is a dog bone pattern, as shown in FIG. 23A. Each cut-out slot has a distal end region with a large width between the opposite sides, and a narrow connection region, with a much smaller width between the opposite sides. The narrow-width regions may be aligned in adjacent slots along the length of the catheter, as shown in FIGS. 23B and 23C. In this example, this alignment of the narrow regions in the middle of the slot (similar to the "closed-cell rectangular slots described above) result in four columns of high-compression strength in the noon 2303, three o'clock 2303', six o'clock 2303" and nine o'clock 2303'" positions radially around the circumference of the slotted catheter (or the slotted portion of the catheter). In this example, each cell has preferred close contact region. As mentioned above, the cells (or regions of the cells along the length of the catheter) can be compressed or stretched and heat-set in an open-cell or closed-cell configuration.

Figures 24A, 24B:
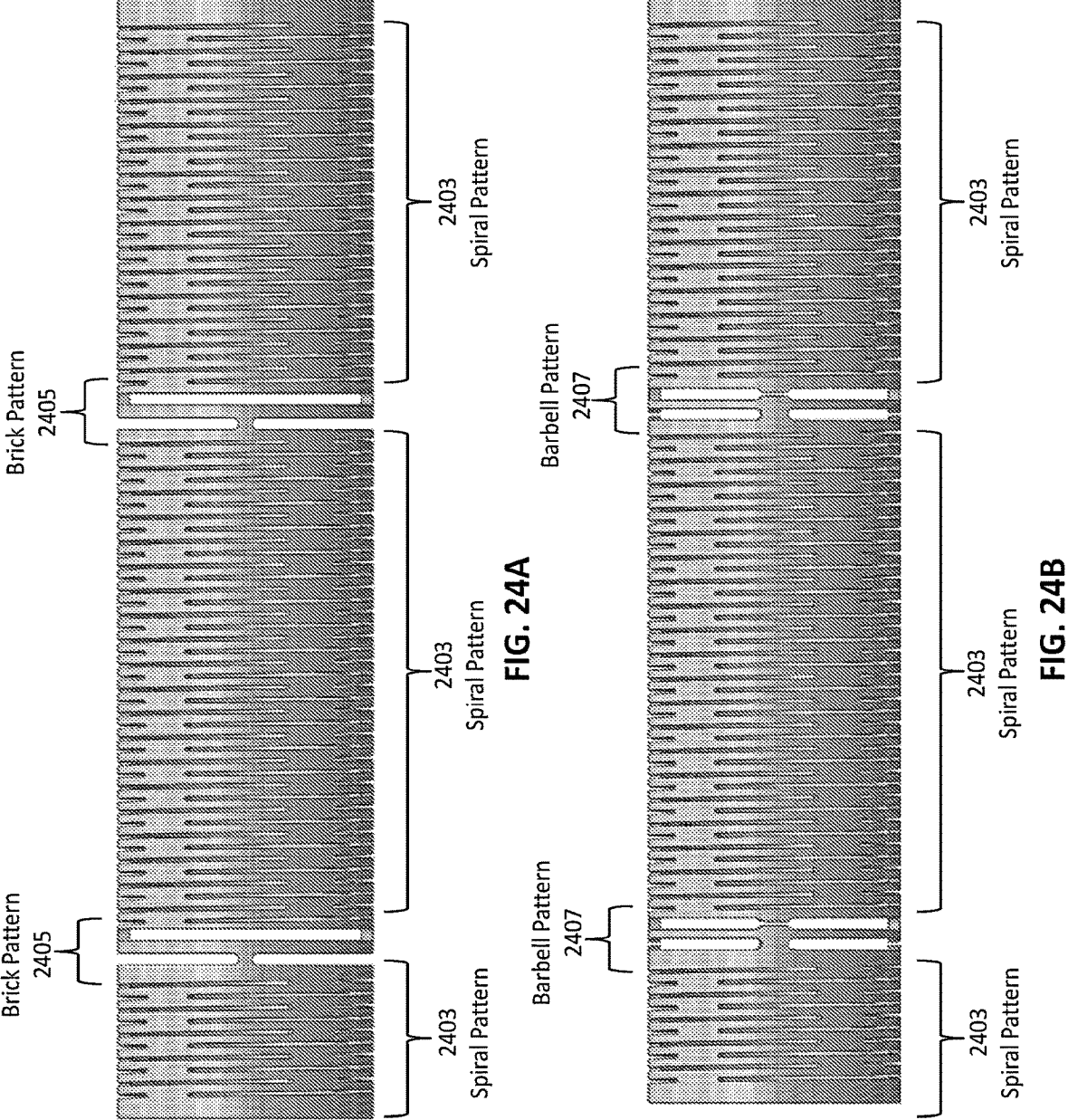
FIGS. 24A-24C illustrate slotted catheters having different slot patterns along their length.
Figure 24C:
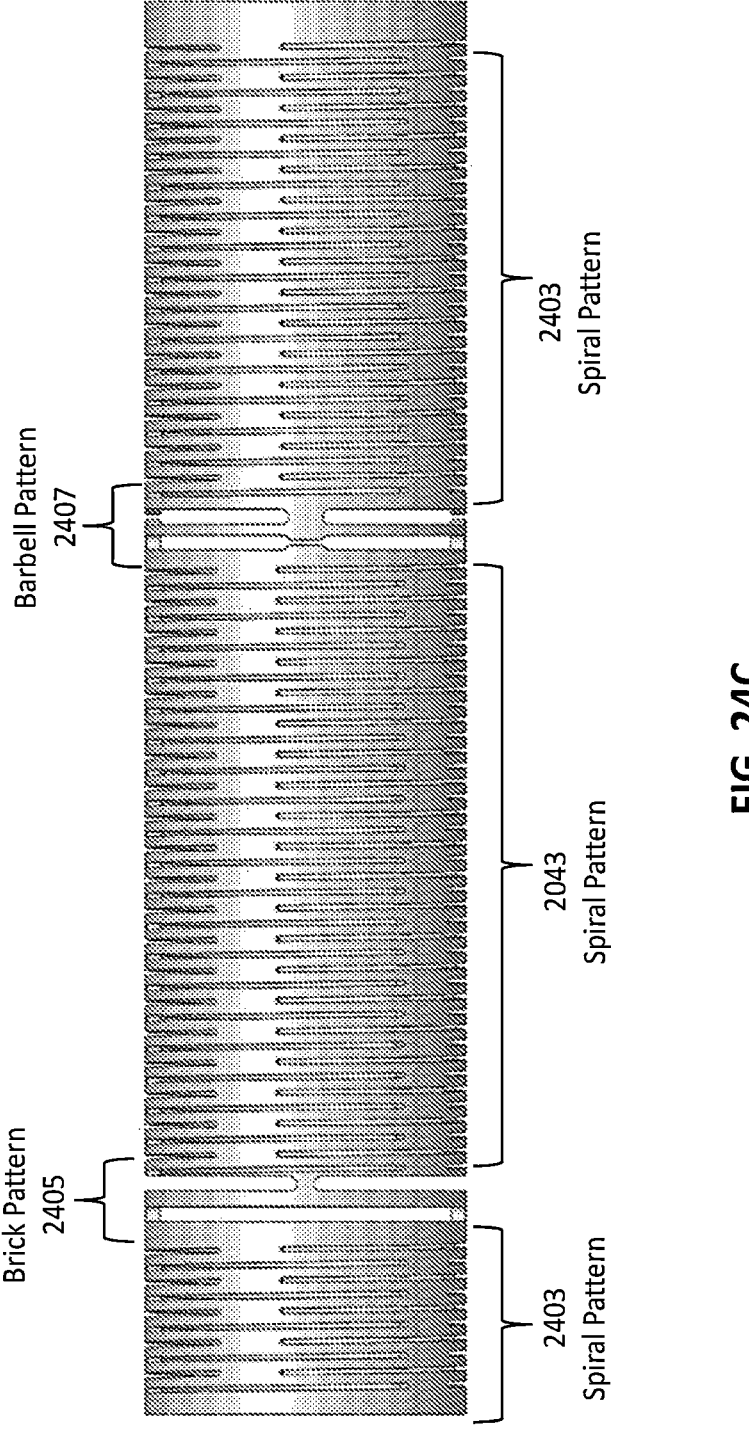

In addition to mixing regions of closed-cell and open-cell slots along the length of the catheter, any of these catheters may also include a mixture of the different patterns disclosed and described herein. For example, FIG. 24A shows an example in which the spiral pattern 2403 of FIGS. 22A-22C is shown adjacent to a region of the brick pattern 2405 of FIG. 21A-21C, which is also adjacent to another region of the spiral pattern. Similarly, FIG. 24B shows alternating spiral patterns 2403 and barbell patterns 2407 such as that shown in FIG. 23A-23C. FIG. 24C shows alternating patterns of spiral 2403, brick 2405, spiral 2403, barbell/dog bone 2407, etc. In any of these catheters, including those of FIGS. 21A-24C, regions along the length may be compressed and/or stretched to form open-cell and closed-cell slots as well.

Figure 25A:
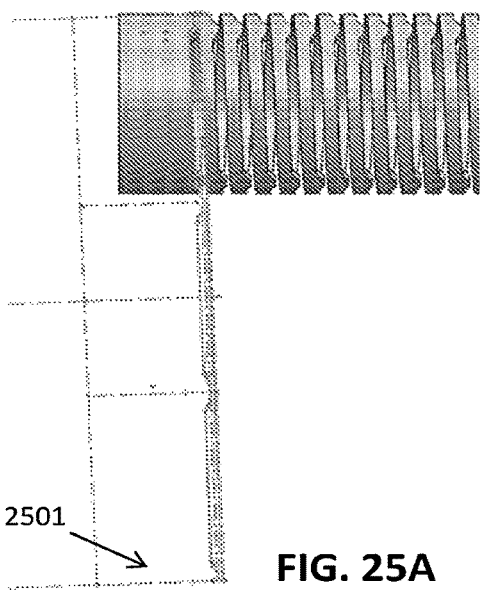
FIGS. 25A-25C illustrate an example of a slotted catheter having a continuous spiral slot cut into the catheter body.
Figure 25B:
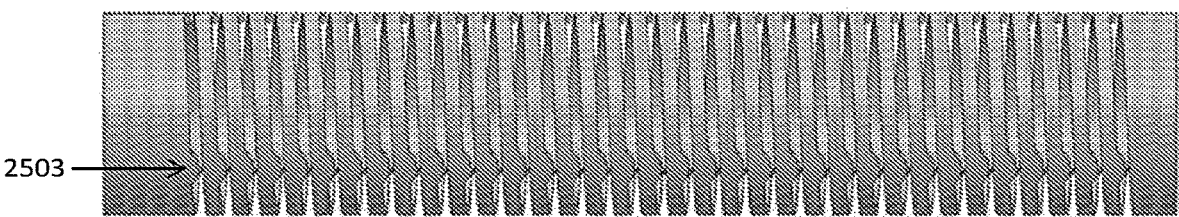
Figure 25C:
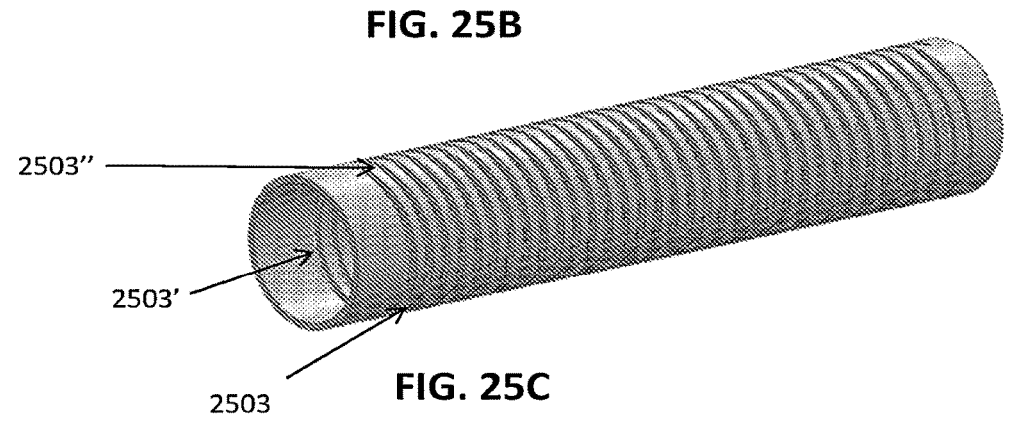

FIGS. 25A-25C illustrate a continuous spiral-cut slotted pattern 2501 in which a slot includes plurality of narrowed regions (bumps, detents, necks, etc.) in the slot and aligned along the longitudinal axis of the catheter to form lines 2503', 2503", 2503'" extending in the long, longitudinal axis of the catheter. As with the embodiments described above, these lines may increase the column strength while the larger-width cut-out regions between them may enhance flexibility. In FIG. 25A, the cut pattern 2501 is shown. As mentioned, the cut pattern may be continuous, and may spiral around and through the catheter (compare to the discrete patterns of FIGS. 21A-24C, which also spiral around the catheter at a very low pitch). FIG. 25B show % s a side view, including the three lines of aligned narrowed regions. Although three lines are shown, a greater or lower number of narrowed regions may be included (e.g., one or more, two or more, three or more, four or more, 2 to 60, 2 to 50, 2 to 40, 2 to 30, 2 to 25, 2 to 20, 2 to 19, etc.), and spaced so that they align to form longitudinally-extending lines. The lines may be parallel with the longitudinal axis of the catheter. In some variations, the lines may spiral around the catheter with a pitch of less than 15 degrees (e.g., less than 14 degrees, less than 12 degrees, less than 10 degrees, less than 8 degrees, less than 6 degrees, less than 5 degrees, etc.). As with the variations shown in any of FIGS. 14A to 24C, the variation shown in FIGS. 25A-25C may be used in order to achieve a high degree of flexibility and column stiffness when pulling a tractor tube into the catheter, as described above, particularly when this pattern is included on the distal end of the catheter (e.g., the distal 30 cm, the distal 25 cm, the distal 20 cm, the distal 15 cm, the distal 20 cm, etc.).

Figure 26:
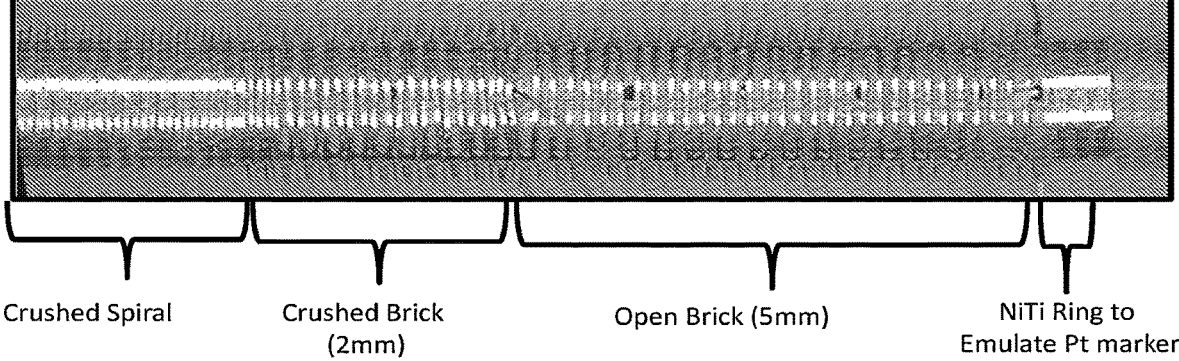
FIG. 26 illustrates one example of an elongate slotted inversion support catheter of a mechanical thrombectomy apparatus for removing a clot from a vessel formed of both a stainless steel (laser cut) and NiTi (nickel titanium) that has been shape-set.
Figure 27:
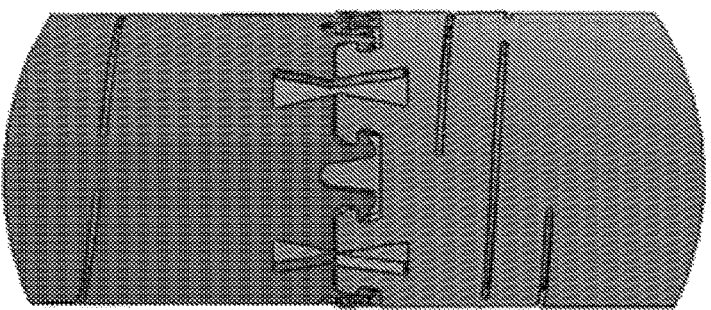
FIG. 27 illustrates a method of joining two regions of an elongate slotted inversion support catheter that are formed of different materials (e.g., stainless steel and nickel titanium).

FIG. 26 illustrates another example of an apparatus including an elongate inversion support catheter comprising a plurality of slots that are arranged approximately transversely to a long axis of the elongate slotted inversion support catheter. In this example, the apparatus includes a first region of the slotted inversion support catheter that has a "crushed spiral" arrangement in which the spiral shape for the slots is formed by cutting (e.g., laser cutting) slots around the circumference, applying a compressive force along the length and heat setting it to hold the compressed format. Adjacent to this first (distal region) is a second region forming a stretch of 'crushed brick' configuration in child wherein the slots have an open diameter of about 0.001 inches or more and wherein there are between 2 and 4 slots per circumferential turn about the long axis, and the region has been compressed (compressively loaded) then heat treated to retain the compressed form. Finally, in FIG. 26, a third slotted region is proximal to the second one is shown. In this third embodiment the third one is an "open brick" configuration in which the slots cut transversely to the long axis of the elongate slotted inversion support catheter, have an open diameter of about 0.001 inches or more and wherein there are between 2 and 4 slots per circumferential turn about the long axis. Any combination of slotted regions (spirals, bricks, open, closed) may be used, in any order of particular interest. Also shown in FIG. 26 is an example of a ring of metal (e.g. shape memory alloy, such as TiNi, or stainless steel, etc. In FIG. 26, the catheter has an ID of 0.048" and an outer diameter (OD) of about 0.062". The catheter is formed of two separate laser-cut hypotubes that have been joined together as shown in FIG. 27 (showing a stainless-steel member interlocking with a nitinol at dovetail joints; a coating or sleeve (e.g., a lamination such as with Tecoflex 80A and Pebax) may be used to secure them together without substantially modifying the flexibility of the catheter. The length of the nitinol catheter cut to form the distal end of the catheter may be approximately 65 cm (e.g., between 40 cm and 100 cm, between 45 cm and 90 cm, between 55 cm and 85, etc.). The length of the stainless steel (SS) catheter cut to form the distal end of the catheter may be approximately 100 cm (e.g., between 50 cm and 150 cm, between 75 cm and 120 cm, between 95 cm and 105 cm, etc.). The regions of the catheter be treated to have a yield compression strength of greater than ~1000 grm.

Figures 28, 29A, 29B:
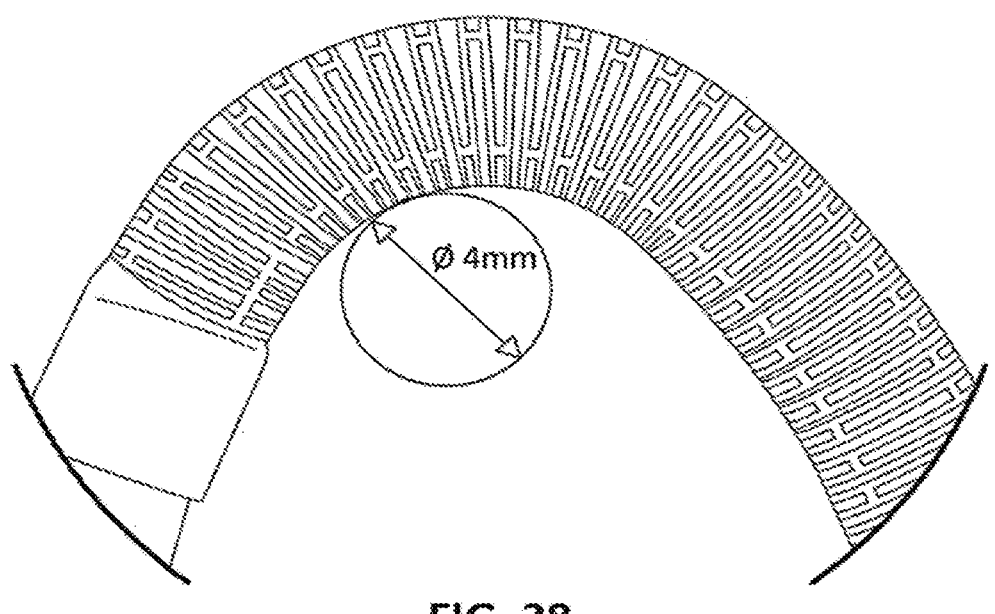
FIG. 28 is an example illustrating the tracking (bending) of a distal end region of an elongate slotted inversion support catheter.
FIG. 29A illustrates an example of a traditional catheter exposed to a high compression force (e.g., when pulling a guidewire through the distal end of the apparatus), showing buckling along the length.
FIG. 29B is another example illustrating an apparatus configured as described herein, e.g., using a specifically configured elongate slotted inversion support catheter having a region of the elongate inversion support catheter comprising a plurality of slots arranged approximately transversely to a long axis of the elongate slotted inversion support catheter, wherein there are between 2 and 4 slots per circumferential turn about the long axis.

FIG. 28 illustrates an example of a catheter, e.g., an elongate inversion support catheter, such as the one shown in FIG. 26, comprising a plurality of slots arranged approximately transversely to a long axis of the elongate slotted inversion support catheter, wherein the slots have an open diameter of about 0.001 inches or less and wherein there are between 2 and 4 slots per circumferential turn about the long axis. FIG. 28, the catheter is shown making a tight turn of 2.8 mm diameter, showing good tracking which may be reflected in the body. Similarly, FIGS. 29A and 29B illustrate an example of a comparison between bending of a traditional support catheter and an elongate inversion support catheter (comprising a plurality of slots arranged approximately transversely to a long axis) as disclosed and described herein. In FIG. 29A, the traditional catheter shows buckling and ultimately fails. In contrast, in FIG. 29B the same applied force (e.g., compressive force) does not cause the device (the elongate inversion support catheter. Thus, the improved elongated inversion support catheter handles high compressive loads without snaking/accordioning/buckling when ingesting hard clot.

Also described herein are tractors having alternating stiffness along their length. For example, a mechanical thrombectomy apparatus for removing a clot from a vessel may include a elongate inversion support including a catheter and having a distal end and a distal end opening and a tractor that is configured as a flexible tube that extends longitudinally within the catheter and doubles back over the distal end of the catheter to extend over the distal end of the catheter. The tractor may be formed of longitudinally alternating regions of higher and lower stiffness, wherein the regions of higher stiffness have a stiffness that is greater than the regions of lower stiffness. In some variations this may allow the lower stiffness regions to act as hinge-regions relative to the stiffer regions, when the tractor is pulled into the catheter. These variations may result in a seesawing motion at the distal end opening of the catheter, as the tractor is inverted and pulled into the catheter. This is illustrated schematically in FIGS. 30A-30D. For example, a portion of a length of tractor may include more stiff regions 3001 and less stiff regions 3003 that are alternating along the long axis of the tractor, as shown schematically in FIG. 30A. As the tractor region is inverted over the distal opening of the catheter (shown in FIG. 30B, in which a portion of the catheter wall is shown 3009), pulling the tractor over the wall 3009 causes the more flexible portions to bend over the wall, while the less flexible regions 3001 bend less or not at all. FIGS. 30B-30D illustrate progression of a tractor portion over the distal end opening, showing the bending of the less stiff/more flexible regions 3003 over the wall, while the more stiff, less flexible regions 3001 do not bend. The result is that, as shown by the arrows on the bottom, the diameter of the distal-facing region changes, and oscillates, as the tractor is pulled into the catheter.

Thus, the tractor may be configured so that it rolls around the catheter tip opening and inverts in a ratcheting fashion, in which parts of the tractor that are stiffer than other sections alternate with more stiff regions. These differently-stiff sections may cause the tractor rolling around the catheter tip to move in a semi-rigid manor and/or a pivoting/seesawing motion around the distal face of the catheter opening and the regions adjacent to the distal opening.

Tractors having alternating stiff/less stiff regions down the length of the catheter (including arranged in a helical manner spiraling down the length) may be formed in a variety of different manners, including constructing braids, laser cut tubes, knits, weaves, and laminates. For example, FIGS. 31A-31D illustrate an example of a knitted tractor region having this configuration. As the variable stiffness tractor rolls around the catheter, sections of the tractor may temporarily dive to towards the center of the catheter ID, which may also aid in grabbing clot or a foreign body to pull into the catheter. The apparatus may be configured so that the tractor includes sections that sea-saw around the catheter tip so the dozer protrudes into the catheter ID by a distal equivalent to 5%, 10,%, 15%, 20%, 25%, 30%, 40%, 50%, 70%, 80%, 90% of the catheter's inner radius length, or any range of the numbers.

The tractor shown in FIG. 31A is a knit construct which has sections that are stiffer alternating with others sections that are less stiff. A first region 2401 of FIG. 31A, is stiffer than the adjacent second region 2403, which is also adjacent to another stiffer region 2401'; the stiffer/less stiff regions alternate and spiral in a helix along the length of the tractor. As the knit tractor shown in FIG. 31A rolls around the catheter, the less stiff section 2403 of the knit shown may temporarily bend, diving the stiffer region 2401 towards the center of the catheter inner diameter in a seesawing motion. FIG. 21B shows a side view or an apparatus including a knit tractor such as shown in FIG. 31A, having alternating stiff/less stiff regions extending down the length of the tractor. FIG. 31C illustrates the distal-facing and inverting tractor that is rolling (in a seesawing manner) over the distal end opening in the catheter. FIGS. 31D and 31E show alternative side and end views, respectively, of a mechanical thrombectomy apparatus including a tractor region such as is shown in FIG. 31A.

Figures 32A, 32B, 32C, 32D:
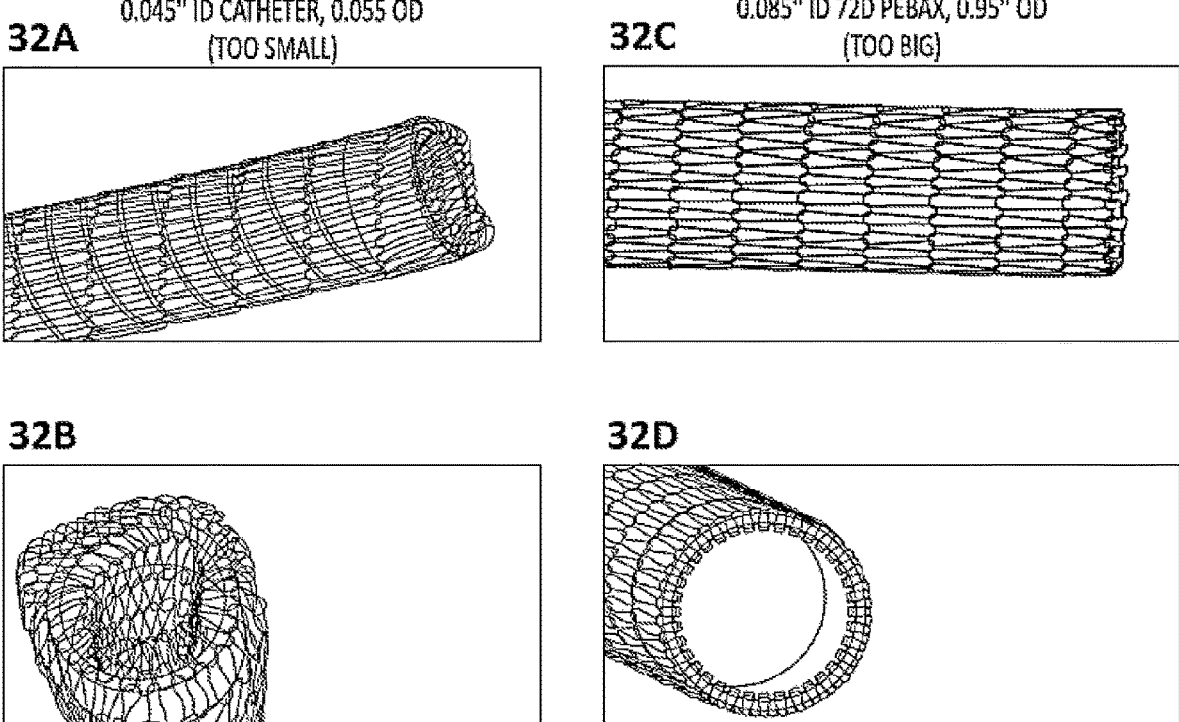
FIGS. 32A-32B illustrate jamming in an apparatus having a seesawing tractor region that has alternating stiff regions that are too long for the diameter of the catheter over which it is inverting.
FIGS. 32C-32D illustrate jamming in an apparatus having a seesawing tractor region that has alternating stiff regions that are too small for the catheter over which it is inverting.

In this example, when the tractor rolls over the distal end opening of the catheter, the alternating stiff/less stiff construction causes the stiffer region to moves towards the center of the catheter, which may aid in grabbing clot or a foreign body to pull into the catheter. The tractor may therefore seesaw around the catheter tip opening so that the tractor protrudes into the catheter ID by a distal equivalent to 5%, 10%, 15%, 20%, 25%, 30%, 40%, 50%, etc. of the catheters inner radius length, before withdrawing, and then repeating the cycle. The alternating stiff and less stiff regions may have a distance (e.g., axial distance, along the long axis of the tractor) that is related to the inner diameter of the catheter. In particular, if the stiff regions are too large relative to the catheter inner diameter, then the tractor may jam in the catheter, as illustrated in FIGS. 32A and 32B. In FIGS. 32A and 32B, for example, the stiff regions are greater than half the diameter of the inner diameter of the catheter.

As shown in FIG. 32B, pulling the tractor into the catheter results in locking or jamming the tractor in the end of the catheter. In some variations the stiff region may be slightly larger than half the diameter without jamming, for example, if the adjacent stiff and less stiff regions wind around the tractor at a sufficiently large angle (e.g., greater than 10 degrees, 15 degrees, 20 degrees, etc.) so that only a subset of the stiff regions moving into the inner diameter of the catheter at the same time. Thus, the length of the stiffer regions may be 0.7 times the diameter of the catheter ID or less (e.g., 0.65 times, 0.6 times, 0.55 times, 0.5 time, 0.45 times, 0.4 times, etc., the diameter of the catheter ID or less). This may also be expressed the length of the stiff region being 1.3 times the radius of the catheter ID or less (e.g., 1.2 times, 1.1 times, 1.0 times, 0.9 times, 0.8 times, etc. the radius of the catheter ID or less). Similarly, if the length of the stiff regions is too small, it will not see-saw in any appreciable amount and may, in some variations, jam onto the end of the catheter, as illustrated in FIGS. 32C and 32D. In FIGS. 32C and 32D, the length of the stiffer alternating regions is not substantially larger than the thickness of the catheter (e.g., the distance between the ID and OD of the catheter), so that no seesawing motion will occur. For example, the length of the stiff region may be 1.1 times or more than the thickness of the catheter (e.g., 1.2 times, 1.3 times, 1.4 times, 1.5 times, 1.6 times, 1.7 times, 1.8 times, 1.9 times, 2 times, etc. or more than the thickness of the catheter). Alternatively, the length of the stiff regions maybe 0.1 times the radius of the catheter or greater (e.g., 0.2 times the radius of the catheter, 0.3 times the radius of the catheter, etc.).

In FIG. 32A-32B, the tractors formed of knit materials having different sizes post-heat treatment (e.g. 0002" knit 26 needle (SN5923) heat treated on a 0.085" mandrel) than those shown in FIGS. 32C and 32D. In FIGS. 32A-32B, the knit material locked on and could not be rolled over the catheter. Relative to the size of the knit, the ID of the catheter (0.045" ID/0.055" OD) was too small. In contrast, in FIGS.

32C and 32D, the catheter dimensions were too large for the knit (e.g., 0.085" ID 72D Pebax, 0.95" OD); the knit material could not pull around and invert on the tubing of this size.

Figure 33A:
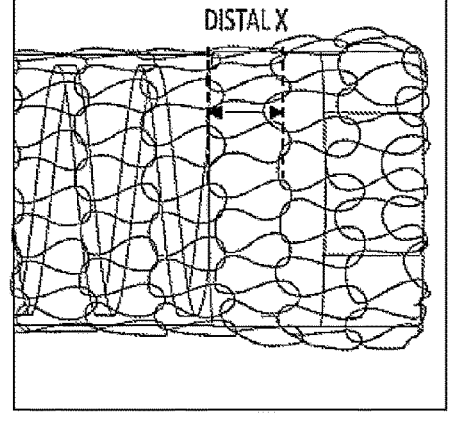
FIGS. 33A and 33B illustrate another example of an apparatus having a knitted tractor.
Figure 33B:
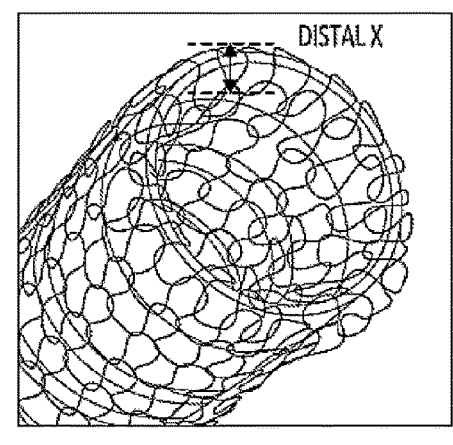

FIGS. 33A and 33B illustrate another example of a seesawing tractor formed form a knitted material FIG. 34 shows an enlarged view of a portion of knitted material forming a tractor. The knitted tractor is formed from a filament (a monofilament or group of fibers collected into a filament) that is knitted to itself. The knit may be a tubular knitted material formed from a filament (monofilament or group of filaments) forming interlocking loops as shown in FIG. 34. In this example, the regions of overlap 3401 between the loops form the stiffer region, while the non-overlapping regions form the less stiff regions 3403. In any of the variations described herein, the loops formed by the knit may also act as protrusions as discussed above, and may aid in drawing the clot into the catheter and/or macerating the clot. For example, the sequence of illustrations in FIGS. 35A-35C show a portion of a knitted tractor having loops of nickel titanium forming alternating stiff/less stiff regions (arranged down the long axis of the tractor) as they roll in a seesawing manner over the distal end opening of the catheter. In this example, a single loop 3501 has been indicated showing it's progression from flush against the wall of the outer diameter of the catheter as the tractor is pulled into the catheter, until, as it approaches the distal opening of the catheter, it inverts by swinging the loop portion 3501 out of the plane of the tractor and up, where it may help grab clot material as shown in FIGS. 3513-35C. The seesawing motion of a limited tractor may also be seen in FIGS. 36A-36B and 37A-37C.

Figures 37A, 37B, 37C:
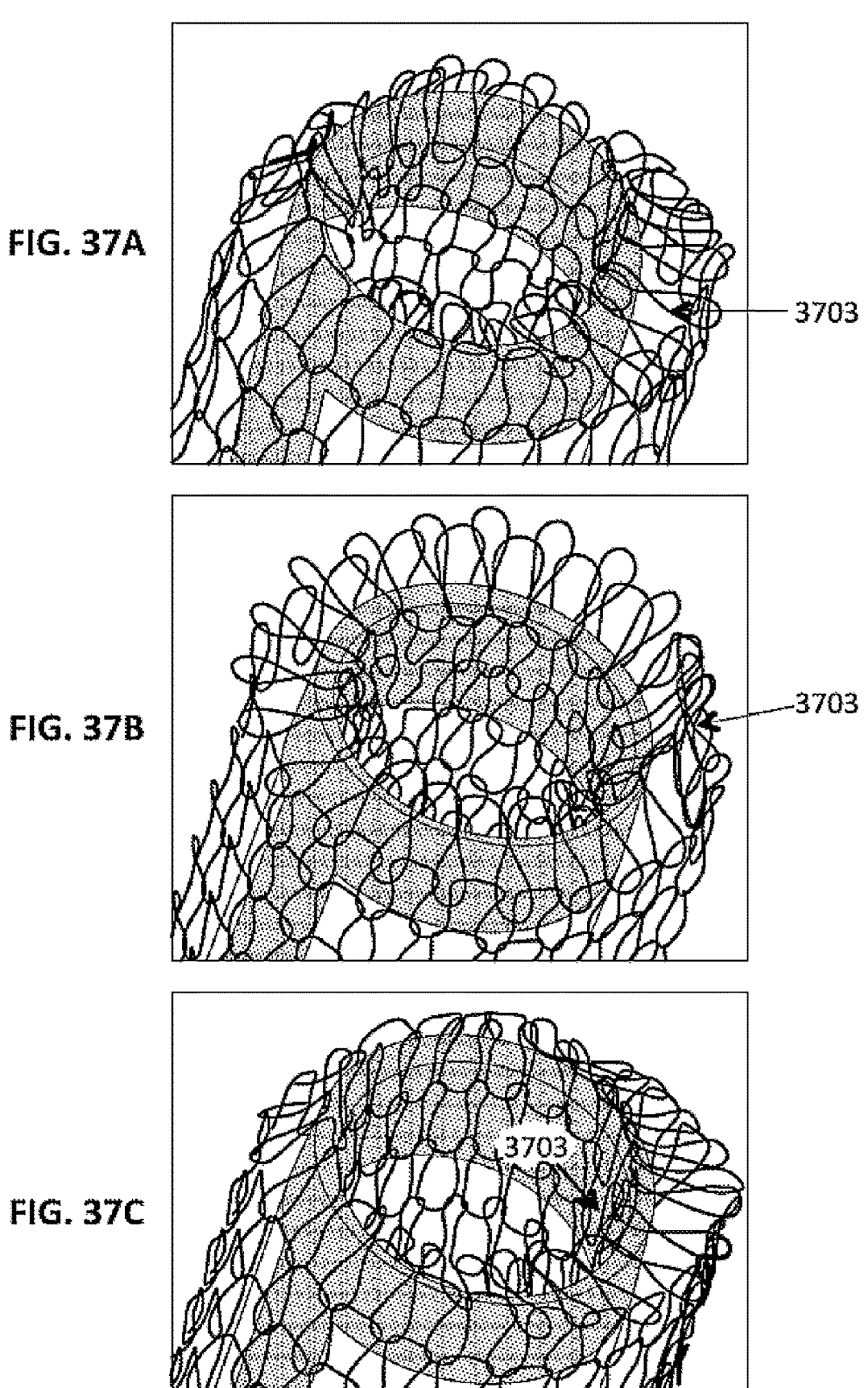
FIGS. 37A-37C illustrate seesawing operation of the apparatus of FIGS. 36A-36B.

An example of a mechanical thrombectomy apparatus is shown in FIGS. 36A-36B from end and side perspective views. FIGS. 37A-37C illustrate a method (e.g., that may be used for grabbing and removing a clot from a vessel) including pulling the distal end of the tractor (in this example, a knitted, seesawing tractor) proximally into the catheter. As shown in FIG. 37A the tractor may initially pull a stiff region 3703 towards the catheter opening. Because it is sufficiently stiff that it does not bend over the edge of the catheter, but is 'hinged to an adjacent stiff region, as the tractor is pulled proximally, the stiff region eventually tilts over the edge (in a seesawing motion), so that one end flips up away from the opening, as shown in FIG. 37B (stiff segment 3703 is indicated); finally it slides forward into the inner diameter of the catheter, as shown in FIG. 37C.

As discussed above, it may be desirable to have a tractor region that is sufficiently and/or selectively coarse so that it may grab a clot. In some variations a rougher tractor may grab clot despite the lubriciousness of the tractor. Knits may be generally more course than braids due to their macro structure (e.g., cells, wire cross overs, shape of cells). Knits may also have the desired porosity discussed above (e.g., having a porosity that permits the tractor to grab and store clot/clot carrying capacity). The size of the pores may be, e.g., between 5-20, 5-10, 10-15 or 15-20 pores on the tractor per circumference. The knit may be formed of any appropriate material, including, e.g., Nickle titanium (Niti) wire. For example, a knit may be formed of a PET monofilament, a PTFE monofilament, etc. A knitted tractor may also have a surface lubricity based on either material properties (e.g., metal, polymer, etc.) or added lubricant (inside, outside, both), and may be radiopaque (e.g., including an inter weave in Pt., DFT, over braid wires with Pt., etc.).

The methods and apparatuses disclosed and described herein may be used with all or some portions of the mechanical clot removal devices shown in each of: U.S.

patent application Ser. No. 15/291,015, filed Oct. 11, 2016; Ser. No. 15/496,570, filed Apr. 25, 2017; Ser. No. 15/496, 668, filed Apr. 25, 2017; Ser. No. 15/496,786, filed Apr. 25, 2017; Ser. No. 15/497,092, filed Apr. 25, 2017; and Ser. No. 15/611,546, filed Jun. 1, 2017.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no inter- vening features or elements present. Although described or shown with respect to one embodiment, the features and elements so described or shown can apply to other embodi- ments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the various inventions disclosed and described herein. For example, as used herein, the singular forms "an" and "the" are intended to include the plural forms as well, unless the context clearly indicates otherwise. It will be further understood that the term "comprises" and/or "com- prising," when used in this specification, specify the pres- ence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower" "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizon- tal" and the like are used herein for the purpose of expla- nation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element dis- cussed herein could be termed a second feature/element, and similarly, a second feature/element discussed herein could be termed a first feature/element without departing from the teachings of the disclosed and described embodiments.

Throughout this specification and the claims which fol- low, unless the context requires otherwise, the word "com- prise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods disclosed and described herein should be understood to be inclusive, but all or a sub-set of the components and/or steps may alternatively be exclusive and may be expressed as "con- sisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be under- stood to include about or approximately that value unless the context indicates otherwise. For example, if the value "10" is disclosed, then "about 10" is also disclosed. Any numeri- cal range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are dis- closed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the dis- closed inventions, which are defined by the claims. For example, the order in which various described method steps are performed may often be changed in alternative embodi- ments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the inventions as they are set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, as many are, in fact, disclosed. Thus, although specific embodiments have been illustrated and disclosed and described herein, any arrangement calculated to achieve the same purpose may be substituted for the specific embodiments shown. This disclosure is intended to cover any and all adaptations or variations of the various embodiments disclosed and described herein, as well as further embodiments not specifically disclosed and/or described herein, will be apparent to those of skill in the art upon reviewing the above description in conjunction with the accompanying drawings.

What is claimed is:

1. A thrombectomy device, comprising:
an inversion support catheter having an outer surface, a distal end, and a distal end opening;
a puller positioned within the inversion support catheter;
a tractor tube having a first portion extending over the outer surface of the inversion support catheter and terminating at an unattached first end of the tractor tube, the tractor tube configured to invert over and into the distal end opening of the inversion support catheter;
wherein a second end of the tractor tube is attached to the puller; and
wherein the first portion of the tractor tube extending over the outer surface of the inversion support catheter comprises a plurality of interlocking links that are configured to flare outwardly from the outer surface of the inversion support catheter.

2. The thrombectomy device of claim 1, wherein a subset of the plurality of interlocking links are configured to flare outwardly from the outer surface of the inversion support catheter as the puller is pulled proximally within the inversion support catheter.

3. The thrombectomy device of claim 1, wherein a subset of the plurality of interlocking links are configured to flare outwardly from the outer surface of the inversion support catheter in a seesawing motion as the puller is pulled proximally within the inversion support catheter.

4. The thrombectomy device of claim 1, wherein the plurality of interlocking links are configured to flare outwardly from the outer surface of the inversion support catheter in a seesawing motion as the puller is pulled proximally within the inversion support catheter.

5. The thrombectomy device of claim 1, wherein the plurality of interlocking links are arranged in axially-spaced rings of interlocking rings.

6. The thrombectomy device of claim 5, wherein the axially-spaced rings of interlocking rings include a first ring and a second ring, and wherein the first ring is coupled to the second ring at a joint.

7. The thrombectomy device of claim 6, wherein the joint has a joint stiffness that is less than a first ring stiffness of the first ring, a second ring stiffness of the second ring, or both.

8. The thrombectomy device of claim 1, wherein the plurality of interlocking links form alternating stiff regions and less stiff regions.

9. The thrombectomy device of claim 8, wherein the alternating stiff regions and less stiff regions helically spiral around the inversion support catheter.

10. The thrombectomy device of claim 1, wherein the plurality of interlocking links are arranged along a length of the tractor tube such that longitudinally-adjacent interlocking links are joined together at a joint.

11. The thrombectomy device of claim 10, wherein the joint has a stiffness that is less than a stiffness of the longitudinally-adjacent interlocking links.

12. The thrombectomy device of claim 1, wherein the tractor tube is knitted.

13. A thrombectomy device, comprising:
an inversion support catheter having an outer surface, a distal end, and a distal end opening;
a puller positioned within the inversion support catheter;
a tractor tube having a first portion extending over the outer surface of the inversion support catheter and terminating at an unattached first end of the tractor tube, the tractor tube configured to invert over and into the distal end opening of the inversion support catheter;
wherein a second end of the tractor tube is attached to the puller;
wherein the tractor tube comprises a plurality of interlocking links;
wherein the plurality of interlocking links are arranged along a length of the tractor tube such that longitudinally-adjacent interlocking links are joined together at a hinge region; and
wherein the hinge region has a stiffness that is less than a stiffness of the longitudinally-adjacent interlocking links.

14. The thrombectomy device of claim 13, wherein a subset of the plurality of interlocking links are configured to flare outwardly from the outer surface of the inversion support catheter as the puller is pulled proximally within the inversion support catheter.

15. The thrombectomy device of claim 13, wherein a subset of the plurality of interlocking links are configured to flare outwardly from the outer surface of the inversion support catheter in a seesawing motion as the puller is pulled proximally within the inversion support catheter.

16. The thrombectomy device of claim 13, wherein the plurality of interlocking links are configured to flare outwardly from the outer surface of the inversion support catheter in a seesawing motion as the puller is pulled proximally within the inversion support catheter.

17. A thrombectomy device, comprising:
an inversion support catheter having an outer surface, a distal end, and a distal end opening;
a puller positioned within the inversion support catheter;
a tractor tube having a first end, a second end coupled to the puller, and a first portion extending over the outer surface of the inversion support catheter;
wherein the tractor tube is configured to invert over and into the distal end opening of the inversion support catheter;
wherein the tractor tube comprises a plurality of interlocking links with a plurality of hinge regions joining longitudinally-adjacent interlocking links; and
wherein at least one of the plurality of hinge regions has a stiffness that is less than a stiffness of at least one of the longitudinally-adjacent interlocking links.

18. The thrombectomy device of claim 17, wherein a subset of the plurality of interlocking links are configured to flare outwardly from the outer surface of the inversion support catheter as the puller is pulled proximally within the inversion support catheter.

19. The thrombectomy device of claim 17, wherein a subset of the plurality of interlocking links are configured to flare outwardly from the outer surface of the inversion support catheter in a seesawing motion as the puller is pulled proximally within the inversion support catheter.

20. The thrombectomy device of claim 17, wherein the plurality of interlocking links are configured to flare outwardly from the outer surface of the inversion support catheter in a seesawing motion as the puller is pulled proximally within the inversion support catheter.

\* \* \* \* \*